(12) United States Patent
Handique

(10) Patent No.: US 8,088,616 B2
(45) Date of Patent: Jan. 3, 2012

(54) HEATER UNIT FOR MICROFLUIDIC DIAGNOSTIC SYSTEM

(75) Inventor: Kalyan Handique, Ypsilanti, MI (US)

(73) Assignee: HandyLab, Inc., Ann Arbor, MI (US)

(*) Notice: Subject to any disclaimer, the term of this patent is extended or adjusted under 35 U.S.C. 154(b) by 1075 days.

(21) Appl. No.: 11/940,315

(22) Filed: Nov. 14, 2007

(65) Prior Publication Data

US 2008/0160601 A1 Jul. 3, 2008

Related U.S. Application Data

(63) Continuation-in-part of application No. 11/728,964, filed on Mar. 26, 2007.

(60) Provisional application No. 60/859,284, filed on Nov. 14, 2006, provisional application No. 60/959,437, filed on Jul. 13, 2007, provisional application No. 60/786,007, filed on Mar. 24, 2006.

(51) Int. Cl.
*C12M 1/34* (2006.01)
*C12M 3/00* (2006.01)

(52) U.S. Cl. ............... 435/287.2; 435/287.1; 435/287.3

(58) Field of Classification Search .......... 435/6, 287.1–287.3, 288.5
See application file for complete search history.

(56) References Cited

U.S. PATENT DOCUMENTS

| | | | |
|---|---|---|---|
| 1,434,314 A | 10/1922 | Raich | |
| 1,616,419 A | 2/1927 | Wilson | |
| 1,733,401 A | 8/1930 | Lovekin | |
| 3,528,449 A | 9/1970 | Witte et al. | |
| 3,985,649 A | 10/1976 | Eddelman | |
| 4,018,089 A | 4/1977 | Dzula et al. | |
| 4,018,652 A | 4/1977 | Lanham et al. | |
| 4,038,192 A | 7/1977 | Serur | |
| 4,055,395 A | 10/1977 | Honkawa et al. | |
| D249,706 S | 9/1978 | Adamski | |

(Continued)

FOREIGN PATENT DOCUMENTS

CA 2294819 1/1999

(Continued)

OTHER PUBLICATIONS

Brahmasandra et al., On-chip DNA detection in microfabricated separation systems, SPIE Conference on Microfuidic Devices and Systems, 1998, vol. 3515, pp. 242-251, Santa Clara, CA.

(Continued)

*Primary Examiner* — Michael Marcheschi
*Assistant Examiner* — Shanta G Doe
(74) *Attorney, Agent, or Firm* — Knobbe Martens Olson & Bear LLP

(57) ABSTRACT

The present technology provides for a heater substrate that contains networks of heater elements configured to controllably and selectively deliver heat to one or more PCR reaction chambers in a microfluidic substrate with which the heater substrate makes contact. In exemplary embodiments, the heater substrate can deliver heat to 12, 24, 48, or 96 chambers independently of one another, or simultaneously. The heater substrate is located in a heater unit that may be introduced into a diagnostic apparatus that can receive and position a microfluidic substrate, such as in a cartridge, in contact with the heater unit, receive one or more polynucleotide containing samples into one or more lanes in the microfluidic substrate, and cause amplification of the polynucleotides to occur, and detect presence of absence of specified polynucleotides in the amplified samples.

19 Claims, 43 Drawing Sheets

U.S. PATENT DOCUMENTS

| | | |
|---|---|---|
| 4,139,005 A | 2/1979 | Dickey |
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,504,582 A | 3/1985 | Swann |
| 4,522,786 A | 6/1985 | Ebersole |
| D279,817 S | 7/1985 | Chen et al. |
| 4,599,315 A | 7/1986 | Terasaki et al. |
| 4,612,873 A | 9/1986 | Eberle |
| 4,612,959 A | 9/1986 | Costello |
| D288,478 S | 2/1987 | Carlson et al. |
| 4,654,127 A | 3/1987 | Baker et al. |
| 4,673,657 A | 6/1987 | Christian |
| 4,683,195 A | 7/1987 | Mullis et al. |
| 4,683,202 A | 7/1987 | Mullis |
| D292,735 S | 11/1987 | Lovborg |
| 4,720,374 A | 1/1988 | Ramachandran |
| 4,798,693 A | 1/1989 | Mase et al. |
| 4,800,022 A | 1/1989 | Leonard |
| D302,294 S | 7/1989 | Hillman |
| 4,895,650 A | 1/1990 | Wang |
| 4,919,829 A | 4/1990 | Gates et al. |
| 4,921,809 A | 5/1990 | Shiff et al. |
| 4,946,562 A | 8/1990 | Guruswamy |
| 4,949,742 A | 8/1990 | Rando et al. |
| D310,413 S | 9/1990 | Bigler et al. |
| 4,963,498 A | 10/1990 | Hillman |
| 4,967,950 A | 11/1990 | Legg et al. |
| 4,978,502 A | 12/1990 | Dole et al. |
| 4,978,622 A | 12/1990 | Mishell et al. |
| 4,989,626 A | 2/1991 | Takagi et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,064,618 A | 11/1991 | Baker et al. |
| 5,071,531 A | 12/1991 | Soane |
| 5,091,328 A | 2/1992 | Miller |
| D324,426 S | 3/1992 | Fan et al. |
| 5,096,669 A | 3/1992 | Lauks et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,169,512 A | 12/1992 | Wiedenmann et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |
| 5,223,226 A | 6/1993 | Whittmer et al. |
| D338,275 S | 8/1993 | Fischer et al. |
| 5,250,263 A | 10/1993 | Manz |
| 5,252,743 A | 10/1993 | Barrett et al. |
| 5,256,376 A | 10/1993 | Callan et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen et al. |
| 5,311,996 A | 5/1994 | Duffy et al. |
| 5,316,727 A | 5/1994 | Suzuki et al. |
| 5,327,038 A | 7/1994 | Culp |
| 5,339,486 A | 8/1994 | Persic, Jr. |
| D351,913 S | 10/1994 | Hieb et al. |
| 5,364,591 A | 11/1994 | Green et al. |
| 5,372,946 A | 12/1994 | Cusak et al. |
| 5,374,395 A | 12/1994 | Robinson |
| 5,389,339 A | 2/1995 | Petschek et al. |
| 5,401,465 A | 3/1995 | Smethers et al. |
| 5,411,708 A | 5/1995 | Moscetta et al. |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |
| 5,474,796 A | 12/1995 | Brennan |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |
| 5,578,818 A | 11/1996 | Kain et al. |
| 5,580,523 A | 12/1996 | Bard |
| 5,582,884 A | 12/1996 | Ball et al. |
| 5,585,069 A | 12/1996 | Zanucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,643,738 A | 7/1997 | Zanzucchi et al. |
| 5,646,039 A | 7/1997 | Northrup et al. |
| 5,647,994 A | 7/1997 | Tuunanen et al. |
| 5,651,839 A | 7/1997 | Rauf |
| 5,652,149 A | 7/1997 | Mileaf et al. |
| D382,346 S | 8/1997 | Buhler et al. |
| D382,647 S | 8/1997 | Staples et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,699,157 A | 12/1997 | Parce |
| 5,700,637 A | 12/1997 | Southern |
| 5,705,813 A | 1/1998 | Apffel et al. |
| 5,726,026 A | 3/1998 | Wilding et al. |
| 5,726,404 A | 3/1998 | Brody |
| 5,726,944 A | 3/1998 | Taft et al. |
| 5,731,212 A | 3/1998 | Gavin et al. |
| 5,744,366 A | 4/1998 | Kricka et al. |
| 5,747,666 A | 5/1998 | Willis |
| 5,750,015 A | 5/1998 | Soane et al. |
| 5,755,942 A | 5/1998 | Zanzucchi et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,787,032 A | 7/1998 | Heller et al. |
| 5,788,814 A | 8/1998 | Sun et al. |

| Patent | Date | Inventor |
|---|---|---|
| 5,800,690 A | 9/1998 | Chow et al. |
| D399,959 S | 10/1998 | Prokop et al. |
| 5,827,481 A | 10/1998 | Bente et al. |
| 5,872,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,872,010 A | 2/1999 | Karger et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benregnu et al. |
| 5,912,124 A | 6/1999 | Kumar |
| 5,912,134 A | 6/1999 | Shartle |
| 5,916,522 A | 6/1999 | Boyd et al. |
| 5,916,776 A | 6/1999 | Kumar |
| 5,919,711 A | 7/1999 | Boyd et al. |
| 5,922,591 A | 7/1999 | Anderson et al. |
| 5,927,547 A | 7/1999 | Papen et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |
| 5,935,401 A | 8/1999 | Amigo |
| 5,939,291 A | 8/1999 | Loewy et al. |
| 5,942,443 A | 8/1999 | Parce et al. |
| D413,677 S | 9/1999 | Dumitrescu et al. |
| 5,948,227 A | 9/1999 | Dubrow |
| 5,955,028 A | 9/1999 | Chow |
| 5,955,029 A | 9/1999 | Wilding et al. |
| 5,957,579 A | 9/1999 | Kopf-Sill et al. |
| 5,958,203 A | 9/1999 | Parce et al. |
| 5,958,694 A | 9/1999 | Nikiforov |
| 5,959,221 A | 9/1999 | Boyd et al. |
| 5,959,291 A | 9/1999 | Jensen |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,972,187 A | 10/1999 | Parce et al. |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,989,402 A | 11/1999 | Chow et al. |
| 5,992,820 A | 11/1999 | Fare et al. |
| 5,993,611 A | 11/1999 | Moroney, III et al. |
| 5,993,750 A | 11/1999 | Ghosh et al. |
| 5,997,708 A | 12/1999 | Craig |
| 6,001,231 A | 12/1999 | Kopf-Sill |
| 6,001,307 A | 12/1999 | Naka et al. |
| 6,004,515 A | 12/1999 | Parce et al. |
| 6,007,690 A | 12/1999 | Nelson et al. |
| 6,010,627 A | 1/2000 | Hood, III |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,043,080 A | 3/2000 | Lipshutz et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,063,341 A | 5/2000 | Fassbind et al. |
| 6,063,589 A | 5/2000 | Kellogg et al. |
| 6,071,478 A | 6/2000 | Chow |
| D428,497 S | 7/2000 | Lapeus et al. |
| 6,086,740 A | 7/2000 | Kennedy |
| 6,102,897 A | 8/2000 | Lang |
| 6,106,685 A | 8/2000 | McBride et al. |
| 6,123,205 A | 9/2000 | Dumitrescu et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,156,199 A | 12/2000 | Zuk, Jr. |
| 6,168,948 B1 | 1/2001 | Anderson et al. |
| 6,171,850 B1 | 1/2001 | Nagle et al. |
| 6,174,675 B1 | 1/2001 | Chow et al. |
| D438,311 S | 2/2001 | Yamanishi et al. |
| D438,632 S | 3/2001 | Miller |
| D438,633 S | 3/2001 | Miller |
| 6,197,595 B1 | 3/2001 | Anderson et al. |
| 6,211,989 B1 | 4/2001 | Wulf et al. |
| 6,221,600 B1 | 4/2001 | MacLeod et al. |
| 6,235,175 B1 | 5/2001 | Dubrow et al. |
| 6,235,313 B1 | 5/2001 | Mathiowitz et al. |
| 6,236,581 B1 | 5/2001 | Lines et al. |
| 6,251,343 B1 | 6/2001 | Dubrow et al. |
| 6,254,826 B1 | 7/2001 | Acosta et al. |
| 6,259,635 B1 | 7/2001 | Torelli et al. |
| 6,261,431 B1 | 7/2001 | Mathies et al. |
| D446,306 S | 8/2001 | Ochi et al. |
| 6,271,021 B1 | 8/2001 | Burns et al. |
| 6,274,089 B1 | 8/2001 | Chow et al. |
| 6,281,008 B1 | 8/2001 | Komai et al. |
| 6,287,254 B1 | 9/2001 | Dodds |
| 6,291,248 B1 | 9/2001 | Haj-Ahmad |
| 6,294,063 B1 | 9/2001 | Becker et al. |
| 6,302,134 B1 | 10/2001 | Kellogg et al. |
| 6,302,304 B1 | 10/2001 | Spencer |
| 6,306,273 B1 | 10/2001 | Wainright et al. |
| 6,319,469 B1 | 11/2001 | Mian et al. |
| 6,326,211 B1 | 12/2001 | Anderson et al. |
| 6,337,435 B1 | 1/2002 | Chu et al. |
| 6,368,871 B1 | 4/2002 | Christel et al. |
| 6,370,206 B1 | 4/2002 | Schenk |
| 6,375,901 B1 | 4/2002 | Robotti et al. |
| 6,379,929 B1 | 4/2002 | Burns et al. |
| 6,379,974 B1 | 4/2002 | Parce et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,403,338 B1 | 6/2002 | Knapp et al. |
| 6,408,878 B2 | 6/2002 | Unger et al. |
| D461,906 S | 8/2002 | Pham |
| 6,428,987 B2 | 8/2002 | Franzen |
| 6,432,366 B2 | 8/2002 | Ruediger et al. |
| 6,440,725 B1 | 8/2002 | Pourahmadi et al. |
| 6,444,461 B1 | 9/2002 | Knapp et al. |
| 6,448,064 B1 | 9/2002 | Vo-Dinh et al. |
| 6,453,928 B1 | 9/2002 | Kaplan et al. |
| D467,348 S | 12/2002 | McMichael et al. |
| D467,349 S | 12/2002 | Niedbala et al. |
| 6,498,497 B1 | 12/2002 | Chow et al. |
| 6,500,390 B1 | 12/2002 | Boulton et al. |
| D468,437 S | 1/2003 | McMenamy et al. |
| 6,509,193 B1 | 1/2003 | Tajima |
| D470,595 S | 2/2003 | Crisanti et al. |
| 6,517,783 B2 | 2/2003 | Horner et al. |

| | | |
|---|---|---|
| 6,520,197 B2 | 2/2003 | Deshmukh et al. |
| 6,521,188 B1 | 2/2003 | Webster |
| D472,324 S | 3/2003 | Rumore et al. |
| 6,534,295 B2 | 3/2003 | Tai et al. |
| 6,544,734 B1 | 4/2003 | Briscoe et al. |
| D474,279 S | 5/2003 | Mayer et al. |
| D474,280 S | 5/2003 | Niedbala et al. |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,597,450 B1 | 7/2003 | Andrews et al. |
| 6,602,474 B1 | 8/2003 | Tajima |
| D480,814 S | 10/2003 | Lafferty et al. |
| D482,796 S | 11/2003 | Oyama et al. |
| 6,664,104 B2 | 12/2003 | Pourahmadi et al. |
| 6,670,153 B2 | 12/2003 | Stern |
| D484,989 S | 1/2004 | Gebrian |
| 6,692,700 B2 | 2/2004 | Handique |
| 6,706,519 B1 | 3/2004 | Kellogg et al. |
| 6,734,401 B2 | 5/2004 | Bedingham et al. |
| D491,272 S | 6/2004 | Alden et al. |
| D491,273 S | 6/2004 | Biegler et al. |
| D491,276 S | 6/2004 | Langille |
| 6,766,817 B2 | 7/2004 | da Silva |
| 6,783,962 B1 | 8/2004 | Olander et al. |
| D495,805 S | 9/2004 | Lea et al. |
| 6,790,330 B2 | 9/2004 | Gascoyne et al. |
| 6,819,027 B2 | 11/2004 | Saraf |
| D499,813 S | 12/2004 | Wu |
| D500,142 S | 12/2004 | Crisanti et al. |
| 6,852,287 B2 | 2/2005 | Ganesan |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,905,612 B2 | 6/2005 | Dorian et al. |
| 6,911,183 B1 | 6/2005 | Handique et al. |
| 6,914,137 B2 | 7/2005 | Baker |
| 6,918,404 B2 | 7/2005 | da Silva |
| D508,999 S | 8/2005 | Fanning et al. |
| 6,942,771 B1 | 9/2005 | Kayyem |
| 6,958,392 B2 | 10/2005 | Fomovskaia et al. |
| D512,155 S | 11/2005 | Matsumoto |
| 6,964,747 B2 | 11/2005 | Banerjee et al. |
| 6,984,516 B2 | 1/2006 | Briscoe et al. |
| D515,707 S | 2/2006 | Sinohara et al. |
| D516,221 S | 2/2006 | Wohlstadter et al. |
| 7,004,184 B2 | 2/2006 | Handique et al. |
| D517,554 S | 3/2006 | Yanagisawa et al. |
| 7,010,391 B2 | 3/2006 | Handique et al. |
| D523,153 S | 6/2006 | Akashi et al. |
| 7,066,586 B2 | 6/2006 | da Silva |
| D528,215 S | 9/2006 | Malmsater |
| D531,321 S | 10/2006 | Godfrey et al. |
| 7,118,910 B2 | 10/2006 | Unger et al. |
| D534,280 S | 12/2006 | Gomm et al. |
| 7,148,043 B2 | 12/2006 | Kordunsky et al. |
| D535,403 S | 1/2007 | Isozaki et al. |
| 7,169,618 B2 | 1/2007 | Skould |
| D537,951 S | 3/2007 | Okamoto et al. |
| D538,436 S | 3/2007 | Patadia et al. |
| 7,192,557 B2 | 3/2007 | Wu et al. |
| 7,235,406 B1 | 6/2007 | Woudenberg et al. |
| D548,841 S | 8/2007 | Brownell et al. |
| D549,827 S | 8/2007 | Maeno et al. |
| 7,270,786 B2 | 9/2007 | Parunak et al. |
| D554,069 S | 10/2007 | Bolotin et al. |
| D554,070 S | 10/2007 | Bolotin et al. |
| D556,914 S | 12/2007 | Okamoto et al. |
| D559,995 S | 1/2008 | Handique et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| D569,526 S | 5/2008 | Duffy et al. |
| 7,374,949 B2 | 5/2008 | Kuriger |
| 7,390,460 B2 | 6/2008 | Osawa et al. |
| 7,476,313 B2 | 1/2009 | Siddiqi |
| 7,494,770 B2 | 2/2009 | Wilding et al. |
| 7,553,671 B2 | 6/2009 | Sinclair et al. |
| 7,604,938 B2 | 10/2009 | Takahashi et al. |
| 7,704,735 B2 | 4/2010 | Facer et al. |
| D621,060 S | 8/2010 | Handique |
| 2001/0023848 A1 | 9/2001 | Gjerde et al. |
| 2001/0038450 A1 | 11/2001 | McCaffrey et al. |
| 2001/0046702 A1 | 11/2001 | Schmebri |
| 2001/0055765 A1 | 12/2001 | O'Keefe et al. |
| 2002/0001848 A1 | 1/2002 | Bedingham et al. |
| 2002/0009015 A1 | 1/2002 | Laugharn, Jr. et al. |
| 2002/0015667 A1 | 2/2002 | Chow |
| 2002/0021983 A1 | 2/2002 | Comte et al. |
| 2002/0037499 A1 | 3/2002 | Quake et al. |
| 2002/0039783 A1 | 4/2002 | McMillan et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0060156 A1 | 5/2002 | Mathies et al. |
| 2002/0068357 A1 | 6/2002 | Mathies et al. |
| 2002/0141903 A1 | 10/2002 | Parunak et al. |
| 2002/0142471 A1 | 10/2002 | Handique et al. |
| 2002/0143297 A1 | 10/2002 | Francavilla et al. |
| 2002/0143437 A1 | 10/2002 | Handique et al. |
| 2002/0169518 A1 | 11/2002 | Luoma et al. |
| 2002/0187557 A1 | 12/2002 | Hobbs et al. |
| 2003/0019522 A1 | 1/2003 | Parunak |
| 2003/0049833 A1 | 3/2003 | Chen et al. |
| 2003/0070677 A1 | 4/2003 | Handique et al. |
| 2003/0073106 A1 | 4/2003 | Johansen et al. |
| 2003/0083686 A1 | 5/2003 | Freeman et al. |
| 2003/0087300 A1 | 5/2003 | Knapp et al. |
| 2003/0127327 A1 | 7/2003 | Kurnik |
| 2003/0136679 A1 | 7/2003 | Bohn et al. |
| 2003/0186295 A1 | 10/2003 | Colin et al. |
| 2003/0199081 A1 | 10/2003 | Wilding et al. |
| 2003/0211517 A1 | 11/2003 | Carulli et al. |
| 2004/0014238 A1 | 1/2004 | Krug et al. |
| 2004/0053290 A1* | 3/2004 | Terbrueggen et al. ............ 435/6 |
| 2004/0063217 A1 | 4/2004 | Webster et al. |
| 2004/0072278 A1 | 4/2004 | Chou et al. |
| 2004/0072375 A1 | 4/2004 | Gjerde et al. |
| 2004/0151629 A1* | 8/2004 | Pease et al. .................. 422/68.1 |
| 2004/0157220 A1 | 8/2004 | Kurnool et al. |
| 2004/0161788 A1 | 8/2004 | Chen et al. |
| 2004/0189311 A1 | 9/2004 | Glezer et al. |
| 2004/0209354 A1 | 10/2004 | Mathies et al. |
| 2004/0219070 A1* | 11/2004 | Handique ....................... 422/99 |
| 2004/0240097 A1 | 12/2004 | Evans |
| 2005/0048540 A1 | 3/2005 | Inami et al. |
| 2005/0084424 A1* | 4/2005 | Ganesan et al. .............. 422/100 |
| 2005/0106066 A1 | 5/2005 | Saltsman et al. |
| 2005/0152808 A1 | 7/2005 | Ganesan |
| 2005/0202504 A1 | 9/2005 | Anderson et al. |
| 2005/0208676 A1 | 9/2005 | Kahatt |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0272079 A1 | 12/2005 | Burns et al. |
| 2006/0041058 A1 | 2/2006 | Yin et al. |
| 2006/0057039 A1* | 3/2006 | Morse et al. .................. 422/198 |
| 2006/0057629 A1 | 3/2006 | Kim |
| 2006/0094108 A1 | 5/2006 | Yoder et al. |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |
| 2006/0165558 A1 | 7/2006 | Witty et al. |
| 2006/0166233 A1 | 7/2006 | Wu et al. |
| 2006/0177376 A1 | 8/2006 | Tomalia et al. |
| 2006/0183216 A1 | 8/2006 | Handique |
| 2006/0207944 A1 | 9/2006 | Siddiqi |
| 2007/0004028 A1 | 1/2007 | Lair et al. |
| 2007/0009386 A1 | 1/2007 | Padmanabhan et al. |
| 2007/0020699 A1 | 1/2007 | Carpenter et al. |
| 2007/0026421 A1 | 2/2007 | Sundberg et al. |
| 2007/0042441 A1 | 2/2007 | Masters et al. |

| | | | |
|---|---|---|---|
| 2007/0092901 A1 | 4/2007 | Ligler et al. | |
| 2007/0098600 A1 | 5/2007 | Kayyem et al. | |
| 2007/0104617 A1 | 5/2007 | Coulling et al. | |
| 2007/0178607 A1 | 8/2007 | Prober et al. | |
| 2007/0184547 A1 | 8/2007 | Handique et al. | |
| 2007/0215554 A1 | 9/2007 | Kreuwel et al. | |
| 2007/0218459 A1 | 9/2007 | Miller et al. | |
| 2007/0231213 A1 | 10/2007 | Prabhu et al. | |
| 2007/0269861 A1 | 11/2007 | Williams et al. | |
| 2007/0292941 A1 | 12/2007 | Handique et al. | |
| 2008/0050804 A1 | 2/2008 | Handique et al. | |
| 2008/0075634 A1 | 3/2008 | Herchenbach et al. | |
| 2008/0095673 A1 | 4/2008 | Xu | |
| 2008/0118987 A1 | 5/2008 | Eastwood et al. | |
| 2008/0124723 A1 | 5/2008 | Dale et al. | |
| 2008/0149840 A1 | 6/2008 | Handique et al. | |
| 2008/0160601 A1 | 7/2008 | Handique | |
| 2008/0182301 A1 | 7/2008 | Handique et al. | |
| 2008/0192254 A1 | 8/2008 | Kim et al. | |
| 2008/0247914 A1 | 10/2008 | Edens et al. | |
| 2008/0262213 A1 | 10/2008 | Wu et al. | |
| 2009/0047713 A1 | 2/2009 | Handique | |
| 2009/0129978 A1 | 5/2009 | Wilson et al. | |
| 2009/0130719 A1 | 5/2009 | Handique | |
| 2009/0130745 A1 | 5/2009 | Williams et al. | |
| 2009/0131650 A1 | 5/2009 | Brahmasandra et al. | |
| 2009/0134069 A1 | 5/2009 | Handique | |
| 2009/0136385 A1 | 5/2009 | Handique et al. | |
| 2009/0136386 A1 | 5/2009 | Duffy et al. | |
| 2009/0155123 A1 | 6/2009 | Williams et al. | |
| 2009/0221059 A1 | 9/2009 | Handique et al. | |
| 2009/0223925 A1 | 9/2009 | Morse et al. | |
| 2010/0009351 A1 | 1/2010 | Brahmasandra et al. | |

FOREIGN PATENT DOCUMENTS

| | | |
|---|---|---|
| DE | 19929734 | 12/1999 |
| EP | 0766256 | 4/1997 |
| FR | 2672301 | 8/1992 |
| FR | 2795426 | 12/2000 |
| JP | 58212921 A | 12/1983 |
| WO | WO 88/06633 | 9/1988 |
| WO | WO 92/05443 | 4/1992 |
| WO | WO 98/00231 | 1/1998 |
| WO | WO 98/22625 | 5/1998 |
| WO | WO 98/53311 | 11/1998 |
| WO | WO 99/09042 | 2/1999 |
| WO | WO 99/12016 | 3/1999 |
| WO | WO 99/33559 | 7/1999 |
| WO | WO 01/05510 | 1/2001 |
| WO | WO 01/14931 | 3/2001 |
| WO | WO 01/27614 | 4/2001 |
| WO | WO 01/28684 | 4/2001 |
| WO | WO 01/41931 | 6/2001 |
| WO | WO 01/54813 | 8/2001 |
| WO | WO 01/89681 | 11/2001 |
| WO | WO 02/078845 | 10/2002 |
| WO | WO 03/012325 | 2/2003 |
| WO | WO 03/012406 | 2/2003 |
| WO | WO 03/055605 | 7/2003 |
| WO | WO 2004/007081 | 1/2004 |
| WO | WO 2004/074848 | 9/2004 |
| WO | WO 2005/011867 | 2/2005 |
| WO | WO 2005/108620 | 11/2005 |
| WO | WO 2006/079082 | 7/2006 |
| WO | WO 2008/060604 | 5/2008 |
| WO | WO 2009/012185 | 1/2009 |

OTHER PUBLICATIONS

Handique et al., 2001, Mathematical modeling of drop mixing in a split-type microchannel, J. Micromech Microeng, 11:548-554.

International Search Report and Written Opinion dated Apr. 4, 2008 for PCT/US07/07513.

International Search Report and Written Opinion for PCT/US07/024022 dated Jan. 5, 2009.

Bollet, C. et al., "A simple method for the isolation of chromosomal DNA from Gram positive or acid-fast bacteria", Nucleic Acids Research, vol. 19, No. 8 (1991), p. 1955.

Breadmore, M.C. et al., "Microchip-Based Purification of DNA from Biological Samples", Anal. Chem., vol. 75 (2003), pp. 1880-1886.

Brody, et al., Diffusion-Based Extraction in a Microfabricated Device, Sensors and Actuators Elsevier, 1997, vol. A58, No. 1, pp. 13-18.

Broyles, et al., "Sample Filtration, Concentration, and Separation Integrated on Microfluidic Devices" Analytical Chemistry (American Chemical Society), vol. 75 No. 11: pp. 2761-2767, (2003).

Burns et al., "An Integrated Nanoliter DNA Analysis Device", Science 282:484-487 (1998).

Carlen et al., "Paraffin Actuated Surface Micromachined Valve," in IEEE MEMS 2000 Conference, p. 381-385, Miyazaki, Japan, Jan. 2000.

Chung, Y. et al., "Microfluidic chip for high efficiency DNA extraction", Miniaturisation for Chemistry, Biology & Bioengineering, vol. 4, No. 2 (Apr. 2004), pp. 141-147.

Handique K., et al., On-Chip Thermopneumatic Pressure for Discrete Drop Pumping, Analytical Chemistry, American Chemical Society, Apr. 15, 2001, vol. 73, No. 8, 1831-1838.

Handique, K. et al, "Microflidic flow control using selective hydrophobic patterning", SPIE, vol. 3224, pp. 185-194 (1997).

Handique, K. et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.

Handique, K. et al., "Mathematical Modeling of Drop Mixing in a Slit-Type Micochannel", J. Micromech. Microeng., 11:548-554 (2001).

Handique, K. et al., "Nanoliter Liquid Metering in Microchannels Using Hydrophobic Patterns", Anal. Chem., 72:4100-4109 (2000).

He, et al., Microfabricated Filters for Microfludic Analytical Systems, Analytical Chemistry, American Chemical Society, 1999, vol. 71, No. 7, pp. 1464-1468.

Ibrahim, et al., Real-Time Microchip PCR for Detecting Single-Base Differences in Viral and Human DNA, Analytical Chemistry, American Chemical Society, 1998, vol. 70, No. 9, pp. 2013-2017.

Khandurina, et al., Microfabricated Porous Membrane Structure for Sample Concentraction and Electrophoretic Analysis, Analytical Chemistry American Chemical Society, 1999, vol. 71, No. 9, pp. 1815-1819.

Kopp, et al., Chemical Amplification: Continuous-Flow PCR on a Chip, www.sciencemag.org, 1998, vol. 280, pp. 1046-1048.

Kutter, et al., Solid Phase Extraction on Microfludic Devices, J. Microcolumn Separations, John Wiley & Sons, Inc., 2000, vol. 12, No. 2, pp. 93-97.

Lagally, et al., Single-Molecule DNA Amplification and Analysis in an Integrated Microfluidic Device, Analytical Chemistry, American Chemical Society, 2001, vol. 73, No. 3 pp. 565-570.

Livache, T. et al., "Polypyrrole DNA chip on a Silicon Device: Example of Hepatitis C Virus Genotyping", Analytical Biochemistry, vol. 255 (1998), pp. 188-194.

Northrup, et al., A Miniature Analytical Instrument for Nucleic Acids Based on Micromachined Silicon Reaction Chambers, Analytical Chemistry, American Chemical Society, 1998, vol. 70, No. 5, pp. 918-922.

Oleschuk, et al., Trapping of Bead-Based Reagents within Microfluidic Systems,: On-Chip Solid-Phase Extraction and Electrochromatography, Analytical Chemistry, American Chemical Society, 2000, vol. 72, No. 3, pp. 585-590.

Orchid BioSciences, Inc., www.orchid.com, Jul. 6, 2001.

Roche, et al. "Ectodermal commitment of insulin-producing cells derived from mouse embryonic stem cells" Faseb J (2005) 19: 1341-1343.

Ross, et al., Analysis of DNA Fragnients from Conventional and Microfabricated PCR Devices Using Delayed Extraction MALDI-TOF Mass Spectrometry, Analytical Chemistry, American Chemical Society, 1998, vol. 70, No. 10, pp. 2067-2073.

Shoffner, M. A. et al., Chip PCR.I. Surface Passivation of Microfabricated Silicon-Glass Chips for PCR, Nucleic Acids Research, Oxford University Press, 1996, vol. 24, No. 2, 375-379.

Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.

Waters, et al., Microchip Device for Cell Lysis, Multiplex PCR Amplification, and Electrophoretic Sizing, Analytical Chemistry, American Chemical Society, 1998, vol. 70, No. 1, pp. 158-162.

Weigl, et al., Microfluidic Diffusion-Based Separation and Detection, www.sciencemag.org, 1999, vol. 283, pp. 346-347.

Yoza, Brandon et al., DNA extraction using bacterial magnetic particles modified with hyperbranched polyamidoamine dendrimer, Mar. 20, 2003, vol. 101, No. 3, 219-228.

Yoza, et al., "Fully Automated DNA Extraction fro Blood Using Magnetic Particles Modified with a Hyperbranched Polyamidomine Dendrimer", Journal of Bioscience and Bioengineering, 95(1):21-26, 2003.

* cited by examiner

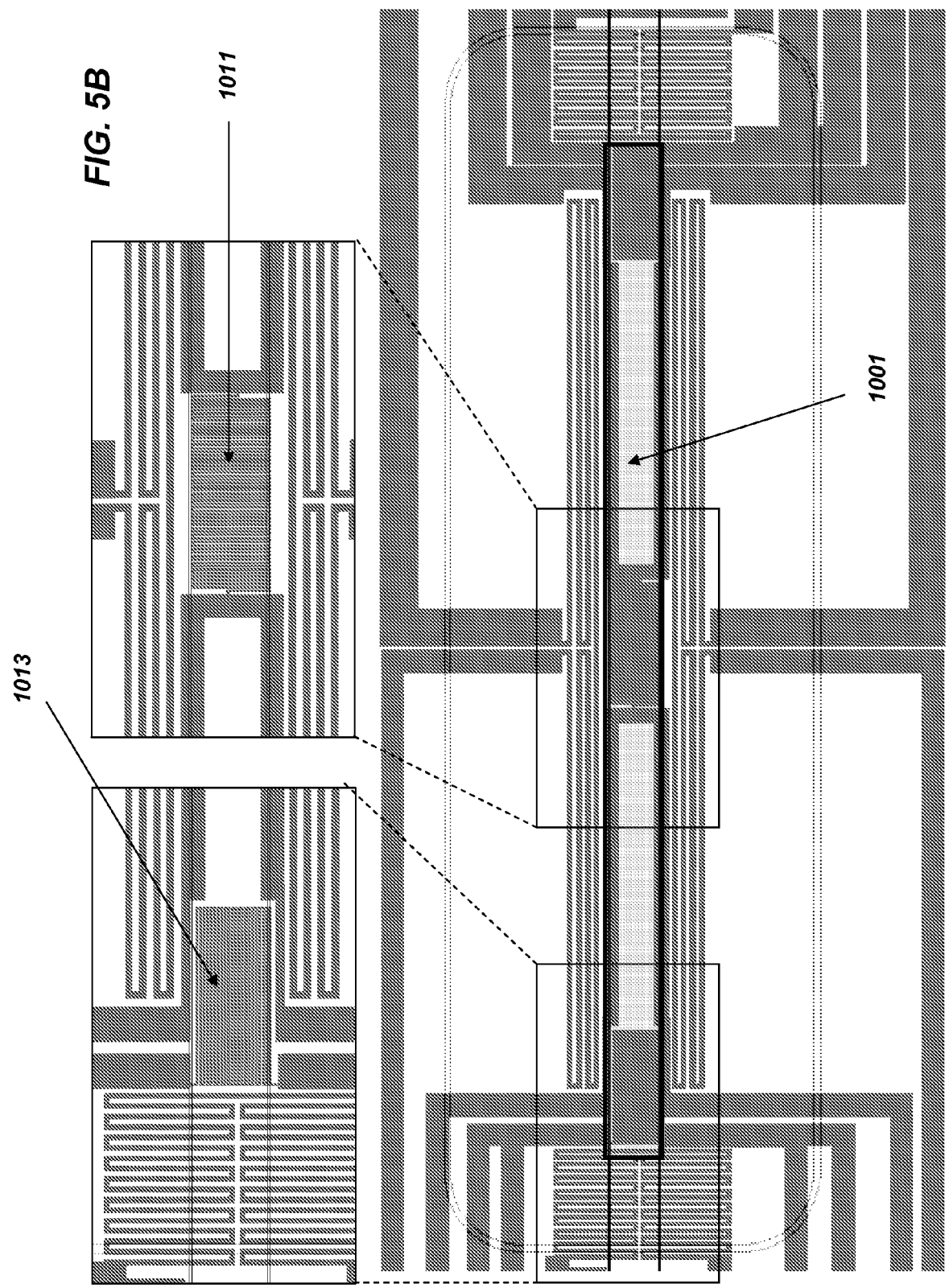

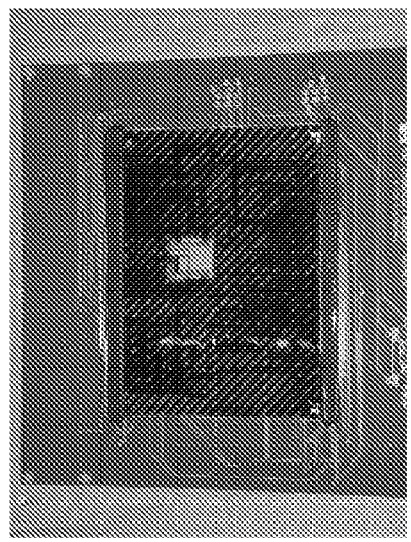
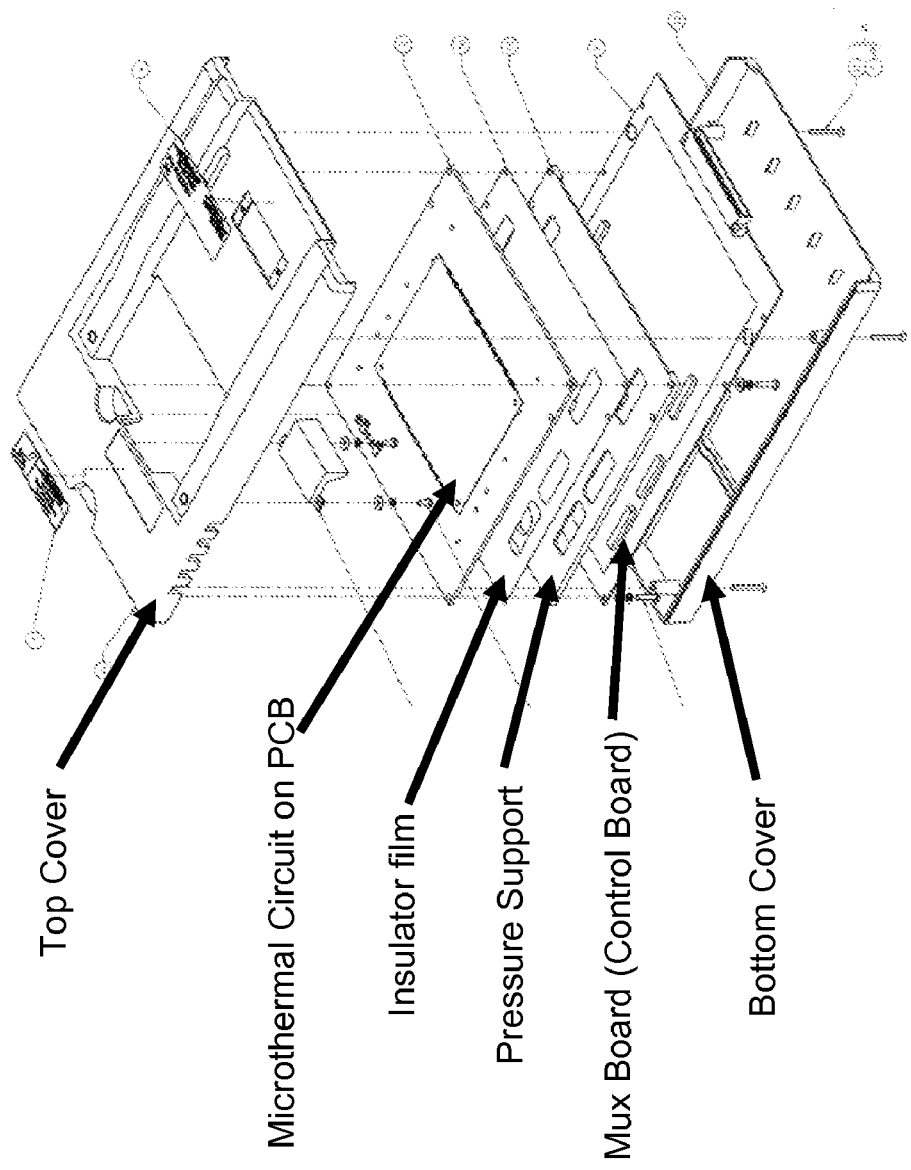
FIG. 26B
FIG. 26A
Top Cover
Microthermal Circuit on PCB
Insulator film
Pressure Support
Mux Board (Control Board)
Bottom Cover

S4/S5

S6/S7

HEATER UNIT FOR MICROFLUIDIC DIAGNOSTIC SYSTEM

CLAIM OF PRIORITY

The instant application claims the benefit of priority to U.S. provisional applications having Ser. Nos. 60/859,284, filed Nov. 14, 2006, and 60/959,437, filed Jul. 13, 2007, the specifications of both of which are incorporated herein by reference in their entireties. The instant application is also a continuation-in-part of U.S. patent application Ser. No. 11/728,964, filed Mar. 26, 2007, which claims the benefit of U.S. provisional application Ser. No. 60/786,007, filed Mar. 24, 2006, and U.S. provisional application Ser. No. 60/859,284, filed Nov. 14, 2006. The specification of U.S. patent application Ser. No. 11/728,964 is incorporated herein by reference in its entirety.

TECHNICAL FIELD

The technology described herein generally relates to systems for detecting polynucleotides in samples, particularly from biological samples. The technology more particularly relates to microfluidic systems that carry out PCR on nucleotides of interest within microfluidic channels, and detect those nucleotides.

BACKGROUND

The medical diagnostics industry is a critical element of today's healthcare infrastructure. At present, however, diagnostic analyses no matter how routine have become a bottleneck in patient care. There are several reasons for this. First, many diagnostic analyses can only be done with highly specialist equipment that is both expensive and only operable by trained clinicians. Such equipment is found in only a few locations—often just one in any given urban area. This means that most hospitals are required to send out samples for analyses to these locations, thereby incurring shipping costs and transportation delays, and possibly even sample loss. Second, the equipment in question is typically not available 'on-demand' but instead runs in batches, thereby delaying the processing time for many samples because they must wait for a machine to fill up before they can be run.

Understanding that sample flow breaks down into several key steps, it would be desirable to consider ways to automate as many of these as possible. For example, a biological sample, once extracted from a patient, must be put in a form suitable for a processing regime that typically involves using PCR to amplify a vector of interest. Once amplified, the presence of a nucleotide of interest from the sample needs to be determined unambiguously. Sample preparation is a process that is susceptible to automation but is also relatively routinely carried out in almost any location, and may still be carried out manually by technicians who require little training. By contrast, steps such as PCR and nucleotide detection have customarily only been within the compass of specially trained individuals having access to specialist equipment.

There is therefore a need for a method and apparatus of carrying out PCR on prepared biological samples and detecting amplified nucleotides, preferably with high throughput. In particular there is a need for an easy-to-use device that can deliver a diagnostic result on several samples in a short time.

The discussion of the background to the technology herein is included to explain the context of the technology. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

The present technology includes methods and devices for detecting polynucleotides in samples, particularly from biological samples. In particular, the technology relates to microfluidic devices that carry out PCR on nucleotides of interest within microfluidic channels, and permit detection of those nucleotides.

The technology comprises a heater substrate. In some embodiments, the heater substrate includes a plurality of groups of resistive heaters. In some embodiments, the heater substrate includes at least one temperature sensor per group of heaters. In some embodiments, the resistive heaters of each of the groups can be configured to mutually control the temperature of a single PCR reaction chamber. In some embodiments, the heater substrate includes control circuitry for supplying electric current to the plurality of groups of resistive heaters at selected intervals. In some embodiments, the heater substrate can include a surface configured to make thermal contact with a microfluidic cartridge that can have a plurality of PCR reaction chambers, and to deliver heat from the plurality of groups of resistive heaters to regions of the cartridge, such that each of the groups of resistive heaters delivers heat to a select PCR reaction chamber to perform a reaction, wherein the heat delivery from each group of resistive heaters is controlled by sensing temperature using the at least one temperature sensor of the group.

The technology further comprises a diagnostic apparatus configured to carry out PCR on a number of samples in parallel, wherein the apparatus utilizes a heater substrate as described above to apply thermal cycling to each of the samples.

The technology still further comprises a heater substrate, the substrate comprising: a plurality of groups of resistive heaters, and at least one temperature sensor per group of heaters, wherein the substrate has a surface configured to make thermal contact with a microfluidic substrate having a plurality of PCR reaction chambers, and to deliver heat from one or more of the plurality of groups of resistive heaters to one or more of the PCR reaction chambers so that a PCR reaction takes place therein, and wherein the heat delivery from each group of resistive heaters is controlled by sensing temperature using the at least one temperature sensor of the group.

The details of one or more embodiments of the technology are set forth in the accompanying drawings and further description herein. Other features, objects, and advantages of the technology will be apparent from the description and drawings, and from the claims.

BRIEF DESCRIPTION OF THE DRAWINGS

FIGS. 5A and 5B show a plan view of heater circuitry adjacent to a PCR reaction chamber;

FIGS. 26A and 26B show an exemplary heater unit and heater substrate;

DETAILED DESCRIPTION

Figure 1:
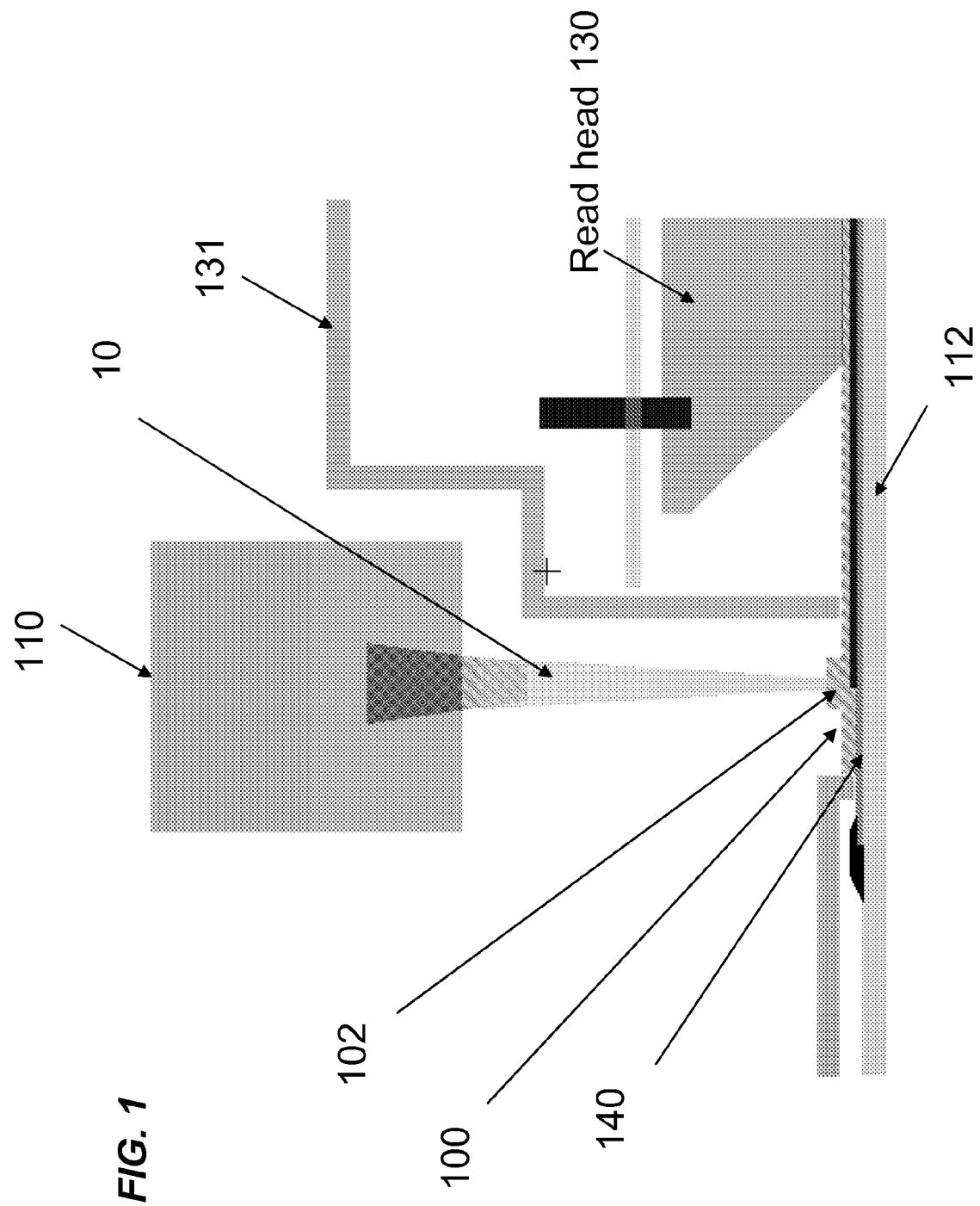
FIG. 1 shows a cross-section of a pipetting head and a cartridge in position in a microfluidic apparatus.

The present technology comprises a heater unit that is configured to apply heat selectively to a microfluidic substrate for the purpose of carrying out an amplification, such as by PCR, of one or more polynucleotides from one or more samples present in the substrate. It is to be understood that, unless specifically made clear to the contrary, where the term PCR is used herein, any other form of polynucleotide amplification is intended to be understood. By apply heat selectively is meant that the heat may be applied to one or more specific locations on the cartridge and at controlled times. Thus certain locations may be heated contemporaneously, such as simultaneously, and other locations may receive heat at different times from one another.

The microfluidic substrate is designed so that it receives thermal energy from one or more heating elements present in the heater unit described herein when it is in thermal communication therewith. A substrate may be part of a cartridge.

By cartridge is meant a unit that may be disposable, or reusable in whole or in part, and that is configured to be used in conjunction with some other apparatus that has been suitably and complementarily configured to receive and operate on (such as deliver energy to via a heater module as described herein) the cartridge.

An exemplary such cartridge is further described herein; additional embodiments of such a cartridge are found in U.S. patent application Ser. No. 11/940,310, entitled "Microfluidic Cartridge and Method of Making Same", and filed on even date herewith, the specification of which is incorporated herein by reference. The heater unit may be part of an apparatus, configured to receive the cartridge, and comprising other features such as control circuitry, user interface, and detector, as well as still other features. An exemplary such apparatus is further described herein; additional embodiments of such an apparatus are found in U.S. patent application Ser. No. 11/985,577, entitled "Microfluidic System for Amplifying and Detecting Polynucleotides in Parallel", and filed on even date herewith, the specification of which is incorporated herein by reference.

By microfluidic, as used herein, is meant that volumes of sample, and/or reagent, and/or amplified polynucleotide are from about 0.1 µl to about 999 µl, such as from 1-100 µl, or from 2-25 µl. Similarly, as applied to a cartridge or a substrate, the term microfluidic means that various components and channels of the cartridge, as further described herein, are configured to accept, and/or retain, and/or facilitate passage of microfluidic volumes of sample, reagent, or amplified polynucleotide.

One aspect of the present technology relates to a heater unit that is configured to apply heat selectively to a microfluidic substrate having two or more sample lanes arranged so that analyses can be carried out in two or more of the lanes in parallel, for example simultaneously, and wherein each lane is independently associated with a given sample.

A sample lane, as found in a microfluidic substrate that is heated by a heater unit herein, is an independently controllable set of elements by which a sample can be analyzed, for example by carrying out PCR on a sample in which the presence or absence of one or more polynucleotides is to be determined, according to methods described in, e.g., U.S. patent application Ser. No. 11/940,310, entitled "Microfluidic Cartridge and Method of Making Same", and filed on even date herewith. A sample lane comprises at least a sample inlet, and a microfluidic network having one or more micro fluidic components, as further described herein.

In various embodiments, a sample lane of a microfluidic substrate can include a sample inlet port or valve, and a microfluidic network that comprises, in fluidic communication one or more components selected from the group consisting of: at least one thermally actuated valve, a bubble removal vent, at least one gate, at least one thermally actuated pump, a downstream thermally actuated valve, mixing channels, one or more positioning elements, and a PCR reaction chamber. The various components of the microfluidic network of each sample lane can be independently and selectively heated by the heater unit described herein.

Channels of a microfluidic network in a lane of a substrate typically have at least one sub-millimeter cross-sectional dimension. For example, channels of such a network may have a width and/or a depth of about 1 mm or less (e.g., about 750 microns or less, about 500 microns, or less, about 250 microns or less).

Particular components of exemplary microfluidic networks are further described in U.S. patent application Ser. No. 11/940,310, entitled "Microfluidic Cartridge and Method of Making Same" and filed on even date herewith.

In various embodiments, the microfluidic network can be configured to couple heat from an external heat source provided by the heater unit described herein to a sample mixture comprising PCR reagent and neutralized polynucleotide sample under thermal cycling conditions suitable for creating PCR amplicons from the neutralized polynucleotide sample.

A multi-lane substrate that is heated by a heater unit described herein is configured to accept a number of samples in series or in parallel, in particular embodiments 12 samples, wherein the samples include at least a first sample and a second sample, wherein the first sample and the second sample each contain one or more polynucleotides in a form suitable for amplification. The polynucleotides in question may be the same as, or different from one another, in different samples and hence in different lanes of the substrate. The substrate typically processes each sample by increasing the concentration of a polynucleotide to be determined and/or by reducing the concentration of inhibitors relative to the concentration of polynucleotide to be determined.

FIG. 1 shows a schematic cross-sectional view of a part of an apparatus as described herein, showing input of sample into a microfluidic cartridge 100 via a pipette 10 (such as a disposable pipette that may be integrated into an automated dispensing hear 110) and an inlet 102. Inlet 102 is preferably configured to receive a pipette or the bottom end of a PCR tube and thereby accept sample for analysis with minimum waste, and with minimum introduction of air. Cartridge 100 is disposed on top of and in contact with a heater substrate 140. Read head 130 is positioned above cartridge 100 and a cover for optics 131 restricts the amount of ambient light that can be detected by the read head. Heater substrate 140 is part of a heater unit (not shown in its entirety in FIG. 1) that is disposed within an apparatus, as further described herein. Cartridge 120 is situated in a suitably configured receiving bay 112.

The contact heat source typically includes a plurality of contact heat sources, each configured at the receiving bay to be independently thermally coupled to a different distinct location in a micro fluidic cartridge received therein, whereby the distinct locations are independently heated. The contact heat sources can be configured to be in direct physical contact with one or more distinct locations of a micro fluidic cartridge received in the bay. In various embodiments, each contact source heater can be configured to heat a distinct location having an average diameter in 2 dimensions from about 1 millimeter (mm) to about 15 mm (typically about 1 mm to about 10 mm), or a distinct location having a surface area of between about 1 $mm^2$ about 225 $mm^2$ (typically between about 1 $mm^2$ and about 100 $mm^2$, or in some embodiments between about 5 $mm^2$ and about 50 $mm^2$).

Heater Unit

Figure 2:
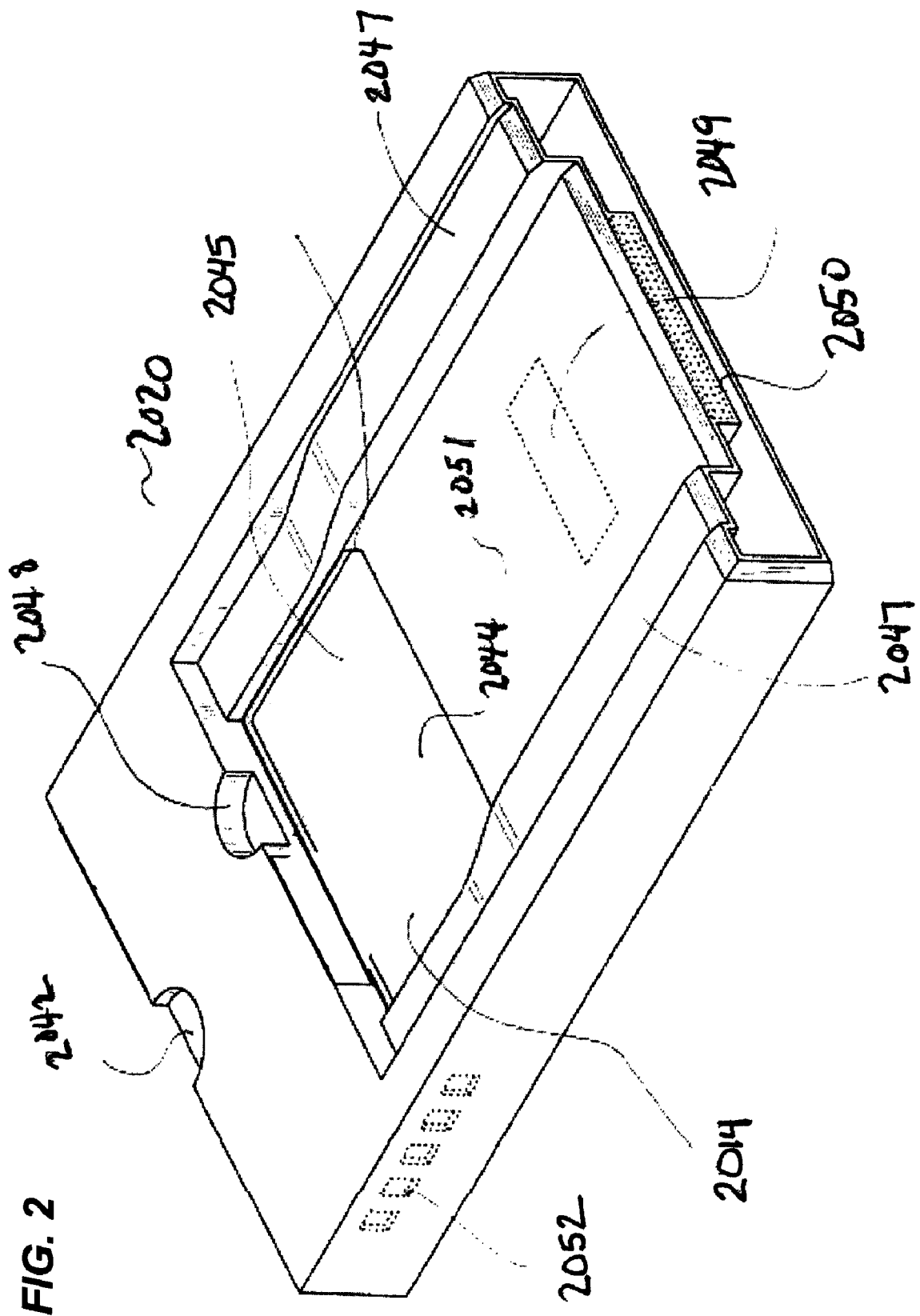
FIG. 2 shows an exemplary heater unit.

An exemplary heater unit 2020 is shown in FIG. 2. The unit is configured to deliver localized heat to various selected regions of a cartridge received in a receiving bay 2014. Heater unit 2020 is configured to be disposed within a diagnostic apparatus during operation, as further described herein, and in certain embodiments is removable from that apparatus, for example to facilitate cleaning, or to permit reconfiguration of the heater circuitry. In various embodiments, heater unit 2020 can be specific to particular designs of microfluidic networks and microfluidic substrate layouts.

Figure 3:
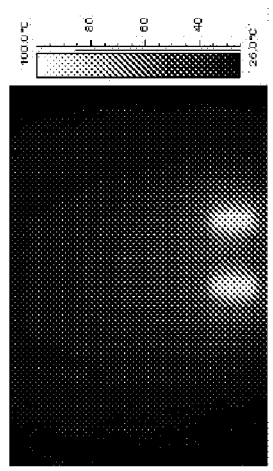
FIG. 3 shows an exemplary heater chip.
Figure 3:
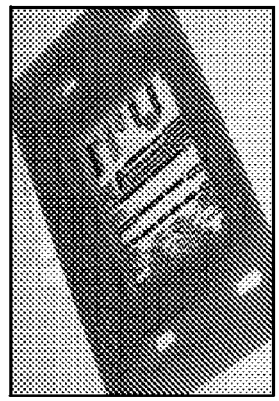
Figure 3:
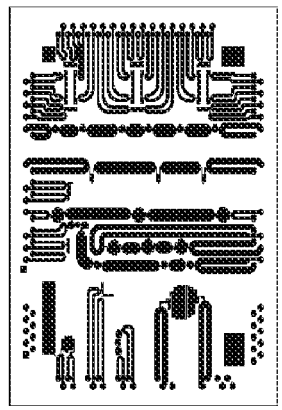

FIG. 3 illustrates heating operation of a heater substrate as further described herein. A schematic of a heater/sensor chip is shown at left. An actual heater/sensor chip bonded to a PCB is in the center of the FIG., A thermal image of the same chip in operation showing highly localized heating (95° C.) in the PCR regions (yellow) is shown at right.

Shown in FIG. 2 is a heater unit having a recessed surface 2044 that provides a platform for supporting a microfluidic cartridge when in receiving bay 2014. In one embodiment, the cartridge rests directly on surface 2044. Surface 2044 is shown as recessed, in FIG. 2, but need not be so and, for example, may be raised or may be flush with the surrounding area of the heater unit. Surface 2044 is typically a layer of material that overlies a heater chip or board, or a heater substrate, that contains heater micro-circuitry configured to selectively and specifically heat regions of a microfluidic substrate, such as in a cartridge, in the receiving bay 2014.

Area 2044 is configured to accept a microfluidic cartridge in a single orientation. Therefore area 2044 can be equipped with a registration member such as a mechanical key that prevents a user from placing a cartridge into receiving bay 2014 in the wrong configuration. Shown in FIG. 2 as an exemplary mechanical key 2045 is a diagonally cutout corner of area 2044 into which a complementarily cutoff corner of a microfluidic cartridge fits. Other registration members are consistent with the heater unit described herein, for example, a feature engineered on one or more edges of a cartridge including but not limited to: several, such as two or more, cut-out corners, one or more notches cut into one or more edges of the cartridge; or one or more protrusions fabricated into one or more edges of the cartridge. Alternative registration members include one or more lugs or bumps engineered into an underside of a cartridge, complementary to one or more recessed sockets or holes in surface 2044 (not shown in the embodiment of FIG. 2). Alternative registration members include one or more recessed sockets or holes engineered into an underside of a cartridge, complementary to one or more lugs or bumps on surface 2044. In general, the pattern of features is such that the cartridge possesses at least one element of asymmetry so that it can only be inserted in a single orientation into the receiving bay.

Also shown in FIG. 2 is a hand-grasp 2042 that facilitates removal and insertion of the heater unit into an apparatus by a user. Cutaway 2048 permits a user to easily remove a cartridge from receiving bay 2014 after a processing run where, e.g., a user's thumb or finger when grabbing the top of the cartridge, is afforded comfort space by cutaway 2048. Both cutaways 2042 and 2048 are shown as semicircular recesses in the embodiment of FIG. 2, but it would be understood that they are not so limited in shape. Thus, rectangular, square, triangular, half-oval, contoured, and other shaped recesses are also consistent with a heater unit as described herein.

In the embodiment of FIG. 2, which is designed to be compatible with an exemplary apparatus as further described herein, the front of the heater unit is at the left of the figure. At the rear of heater unit 2020 is an electrical connection 2050, such as an RS-232 connection, that permits electrical signals to be directed to heaters located at specific regions of area 2044 during sample processing and analysis, as further described herein. Thus, underneath area 2044 and not shown in FIG. 2 can be an array of heat sources, such as resistive heaters, that are configured to align with specified locations of a microfluidic cartridge properly inserted into the receiving bay. Surface 2044 is able to be cleaned periodically, for example with common cleaning agents (e.g., a 10% bleach solution), to ensure that any liquid spills that may occur during sample handling do not cause any short circuiting. Such cleaning can be carried out frequently when the heater unit is disposed in a diagnostic apparatus, and less frequently but more thoroughly when the unit is removed.

Other non-essential features of heater unit 2020 are as follows. One or more air vents 2052 can be situated on one or more sides (such as front, rear, or flanking) or faces (such as top or bottom) of heater unit 2020, to permit excess heat to escape, when heaters underneath receiving bay 2014, are in operation. The configuration of air vents in FIG. 2, as a linear array of square vents, is exemplary and it would be understood that other numbers and shapes thereof are consistent with routine fabrication and use of a heater unit. For example, although 5 square air vents are shown, other numbers such as 1, 2, 3, 4, 6, 8, or 10 air vents are possible, arranged on one side, or spread over two or more sides and/or faces of the heater unit. In further embodiments, air vents may be circular, rectangular, oval, triangular, polygonal, and having curved or squared vertices, or still other shapes, including irregular shapes. In further embodiments two or more vents need not be disposed in a line, parallel with one another and with an edge of the heater unit but may be disposed offset from one another.

Heater unit 2020 may further comprise one or more guiding members 2047 that facilitate inserting the heater unit into an apparatus as further described herein, for an embodiment in which heater unit 2020 is removable by a user. Heater unit is advantageously removable because it permits system 2000 to be easily reconfigured for a different type of analysis, such as employing a different cartridge with a different registration member and/or microfluidic network, in conjunction with the same or a different sequence of processing operations. In other embodiments, heater unit 2020 is designed to be fixed and only removable, e.g., for cleaning, replacement, or maintenance, by the manufacturer or an authorized maintenance agent, and not routinely by the user. Guiding members 2047 may perform one or more roles of ensuring that the heater unit is aligned correctly in the apparatus, and ensuring that the heater unit makes a tight fit and does not significantly move during processing and analysis of a sample, or during transport of the apparatus.

Guiding members shown in the embodiment of FIG. 2 are on either side of receiving bay 2044 and stretch along a substantial fraction of the length of unit 2020, but such an arrangement of guiding members is exemplary. Other guiding members are consistent with use herein, and include but are not limited to other numbers of guiding members such as 1, 3, 4, 5, 6, or 8, and other positions thereof, including positioned in area 2051 of unit 2020, and need not stretch along as much of the length of unit 2020 as shown in FIG. 2, or may stretch along its entire length. Guiding members 2047 are shown having a non-constant thickness along their lengths. It is consistent herein that other guiding members may have essentially constant thickness along their lengths. At the end of the heater unit that is inserted into an apparatus, in the embodiment shown, the edges are beveled to facilitate proper placement.

Also shown in FIG. 2 is an optional region of fluorescent material, such as optically fluorescent material 2049, on area 2051 of heater unit 2020. The region of fluorescent material is configured to be detected by a detection system further described herein. The region 2049 is used for verifying the state of optics in the detection system prior to sample processing and analysis and therefore acts as a control, or a standard. For example, in one embodiment a lid of the apparatus in which the heater unit is disposed, when in an open position, permits ambient light to reach region 2049 and thereby cause the fluorescent material to emit a characteristic frequency or spectrum of light that can be measured by the detector for, e.g., standardization or calibration purposes. In another embodiment, instead of relying on ambient light to cause the fluorescent material to fluoresce, light source from the detection system itself, such as one or more LED's, is used to shine on region 2049. The region 2049 is therefore positioned to align with a position of a detector. Region 2049 is shown as rectangular, but may be configured in other shapes such as square, circular, elliptical, triangular, polygonal, and having curved or squared vertices. It is also to be understood that the region 2049 may be situated at other places on the heater unit 2020, according to convenience and in order to be complementary to the detection system deployed.

In particular and not shown in FIG. 2, heater/sensor unit 2020 can include, for example, a multiplexing function in a discrete multiplexing circuit board (MUX board), one or more heaters (e.g., a microheater), one or more temperature sensors (optionally combined together as a single heater/sensor unit with one or more respective microheaters, e.g., as photolithographically fabricated on fused silica substrates). The micro-heaters can provide thermal energy that can actuate various microfluidic components on a suitably positioned microfluidic cartridge. A sensor (e.g., as a resistive temperature detector (RTD)) can enable real time monitoring of the micro-heaters, for example through a feedback based mechanism to allow for rapid and accurate control of the temperature. One or more microheaters can be aligned with corresponding microfluidic components (e.g., valves, pumps, gates, reaction chambers) to be heated on a suitably positioned microfluidic cartridge. A microheater can be designed to be slightly bigger than the corresponding microfluidic component(s) on the microfluidic cartridge so that even though the cartridge may be slightly misaligned, such as off-centered, from the heater, the individual components can be heated effectively.

Heater Configurations to Ensure Uniform Heating of a Region

The microfluidic substrates described herein are configured to accept heat from a contact heat source, such as found in a heater unit described herein. The heater unit typically comprises a heater board or heater chip that is configured to deliver heat to specific regions of the microfluidic substrate, including but not limited to one or more microfluidic components, at specific times. For example, the heat source is configured so that particular heating elements are situated adjacent to specific components of the microfluidic network on the substrate. In certain embodiments, the apparatus uniformly controls the heating of a region of a microfluidic network. In an exemplary embodiment, multiple heaters can be configured to simultaneously and uniformly heat a region, such as the PCR reaction chamber, of the microfluidic substrate. The term heater unit, as used herein, may be used interchangeably to describe either the heater board or an item such as shown in FIG. 2.

Figure 4:
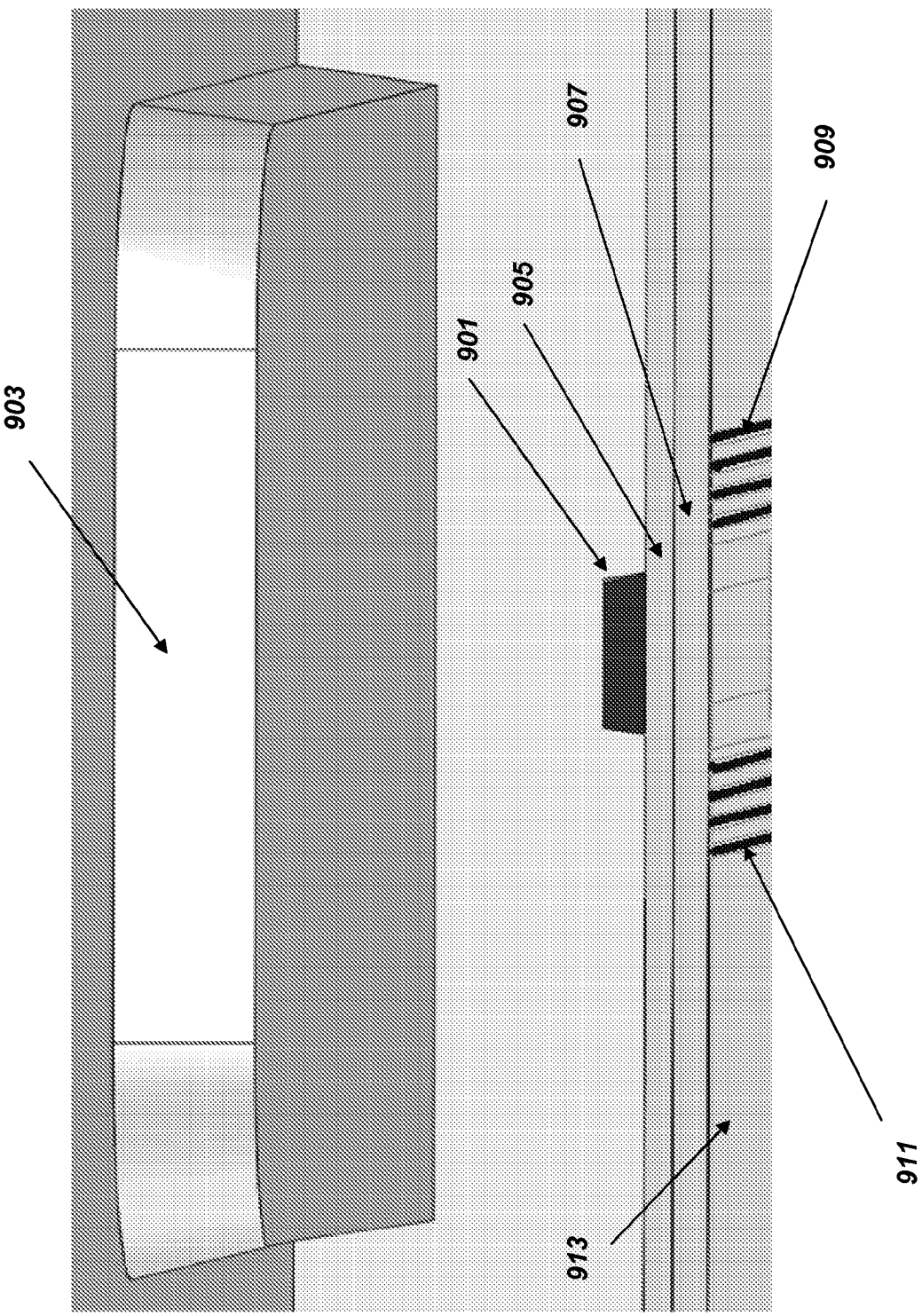
FIG. 4 shows a cross-section of a microfluidic cartridge, when in contact with a heater substrate.

FIG. 4 shows a cross-sectional view of an exemplary microfluidic cartridge to show relative location of PCR channel in relation to various heaters when the cartridge is placed in the instrument. The view in FIG. 4 is also referred to as a sectional-isometric view of the cartridge lying over the heater wafer. A window 903 above the PCR channel in the cartridge is shown in perspective view. PCR channel 901 (for example, 150μ deep×700μ wide), is shown in an upper layer of the cartridge. A laminate layer 905 of the cartridge (for example, 125μ thick) is directly under the PCR channel 901. As depicted, an optional further layer of thermal interface laminate 907 on the cartridge (for example, 125μ thick) lies directly under the laminate layer 905. Heaters 909, 911 are situated in a heater substrate layer 913 directly under the thermal interface laminate. The heaters are photolithographically defined and etched metal layers of gold (typically about 3,000 Å thick). Layers of 400 Å of TiW are deposited on top and bottom of the gold layer to serve as an adhesion layer. The substrate used is glass, fused silica or quartz wafer having a thickness of 0.4 mm, 0.5 mm, 0.7 mm, or 1 mm. A thin electrically-insulative layer of 2 μm silicon oxide serves as an insulative layer on top of the metal layer. Additional thin electrically insulative layers such as 2-4 g/m of Parylene may also be deposited on top of the silicon oxide surface. Two long heaters 909 and 911, as further described herein, run alongside the PCR channel.

Figure 5A:
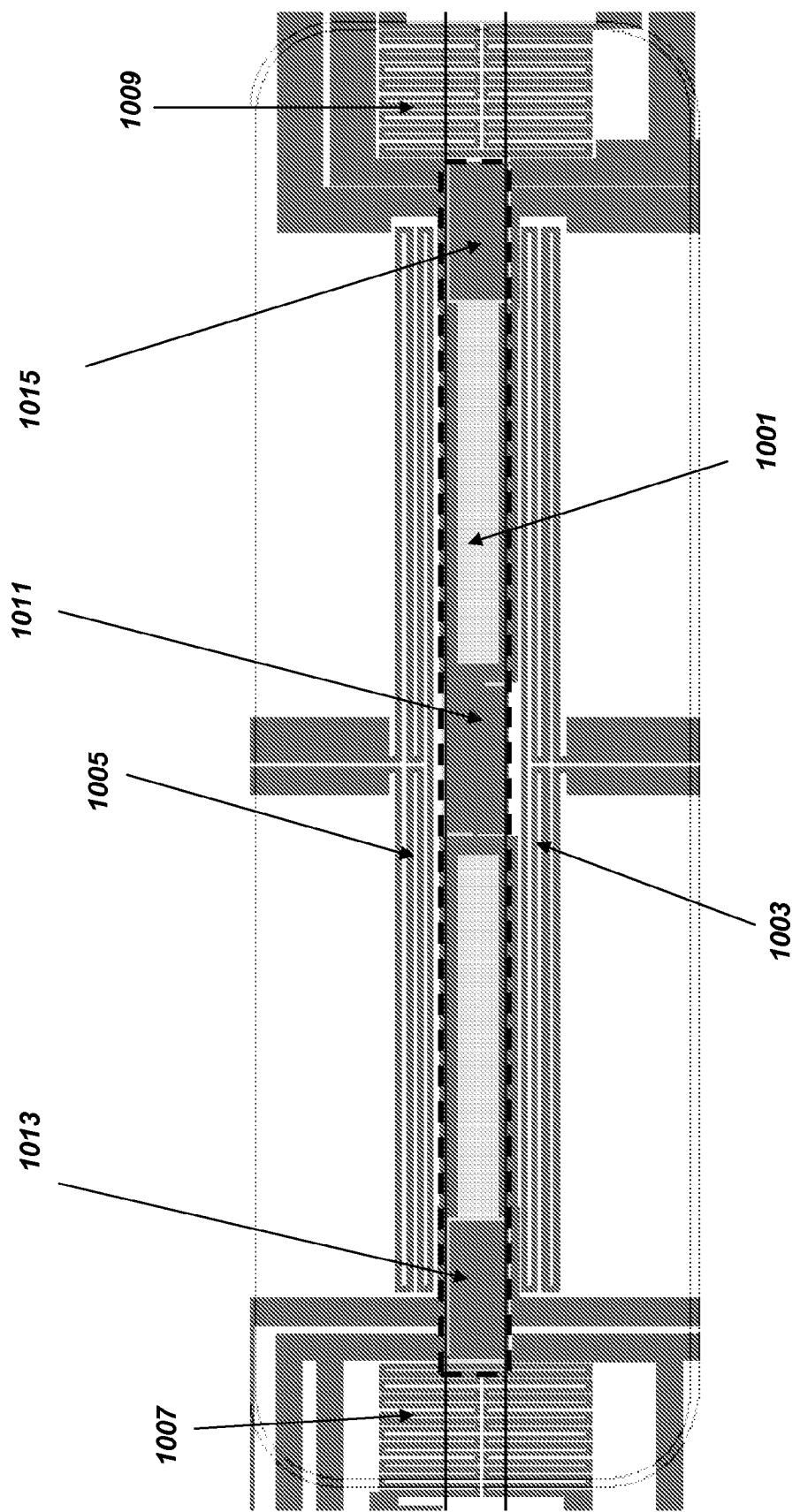

Referring to FIGS. 5A and 5B, an exemplary set of heaters configured to heat, cyclically, PCR reaction chamber 1001 is shown. It is to be understood that heater configurations to actuate other regions of a microfluidic cartridge such as other gates, valves, and actuators, may be designed and deployed according to similar principles to those governing the heaters shown in FIGS. 5A and 5B.

An exemplary PCR reaction chamber 1001 in a microfluidic substrate, typically a chamber or channel having a volume ~1.6 µl, is configured with a long side and a short side, each with an associated heating element. A PCR reaction chamber may also be referred to as a PCR reactor, herein, and the region of a cartridge in which the reaction chamber is situated may be called a zone. The heater substrate therefore preferably includes four heaters disposed along the sides of, and configured to heat, a given PCR reaction chamber, as shown in the exemplary embodiment of FIG. 5A: long top heater 1005, long bottom heater 1003, short left heater 1007, and short right heater 1009. The small gap between long top heater 1005 and long bottom heater 1003 results in a negligible temperature gradient (less than 1° C. difference across the width of the PCR channel at any point along the length of the PCR reaction chamber) and therefore an effectively uniform temperature throughout the PCR reaction chamber. The heaters on the short edges of the PCR reactor provide heat to counteract the gradient created by the two long heaters from the center of the reactor to the edge of the reactor.

It would be understood by one of ordinary skill in the art that still other configurations of one or more heater(s) situated about a PCR reaction chamber are consistent with the methods and apparatus described herein. For example, a 'long' side of the reaction zone can be configured to be heated by two or more heaters. Specific orientations and configurations of heaters are used to create uniform zones of heating even on substrates having poor thermal conductivity because the poor thermal conductivity of glass, or quartz, polyimide, FR4, ceramic, or fused silica substrates is utilized to help in the independent operation of various microfluidic components such as valves and independent operation of the various PCR lanes. It would be further understood by one of ordinary skill in the art, that the principles underlying the configuration of heaters around a PCR reaction zone are similarly applicable to the arrangement of heaters adjacent to other components of the microfluidic cartridge, such as actuators, valves, and gates.

In certain embodiments, each heater has an associated temperature sensor. In the embodiment of FIG. 5A, a single temperature sensor 1011 is used for both long heaters. A temperature sensor 1013 for short left heater, and a temperature sensor 1015 for short right heater are also shown. The temperature sensor in the middle of the reactor is used to provide feedback and control the amount of power supplied to the two long heaters, whereas each of the short heaters has a dedicated temperature sensor placed adjacent to it in order to control it. As further described herein, temperature sensors are preferably configured to transmit information about temperature in their vicinity to a processor in the apparatus at such times as the heaters are not receiving current that causes them to heat. This can be achieved with appropriate control of current cycles.

In order to reduce the number of sensor or heater elements required to control a PCR heater, the heaters may be used to sense as well as heat, and thereby obviate the need to have a separate dedicated sensor for each heater. In another embodiment, each of the four heaters may be designed to have an appropriate wattage, and connect the four heaters in series or in parallel to reduce the number of electronically-controllable elements from four to just one, thereby reducing the burden on the associated electronic circuitry.

FIG. 5B shows expanded views of heaters and temperature sensors used in conjunction with a PCR reaction chamber of FIG. 5A. Temperature sensors 1001 and 1013 are designed to have a room temperature resistance of approximately 200-300 ohms. This value of resistance is determined by controlling the thickness of the metal layer deposited (e.g., a sandwich of 400 Å TiW/3,000 Å Au/400 Å TiW), and etching the winding metal line to have a width of approximately 10-25 µm and 20-40 mm length. The use of metal in this layer gives it a temperature coefficient of resistivity of the order of 0.5-20° C./ohms, preferably in the range of 1.5-3° C./ohms. Measuring the resistance at higher temperatures enables determination of the exact temperature of the location of these sensors.

The configuration for uniform heating, shown in FIG. 5A for a single PCR reaction chamber, can also be applied to a multi-lane PCR cartridge in which multiple independent PCR reactions occur.

Figure 5C:
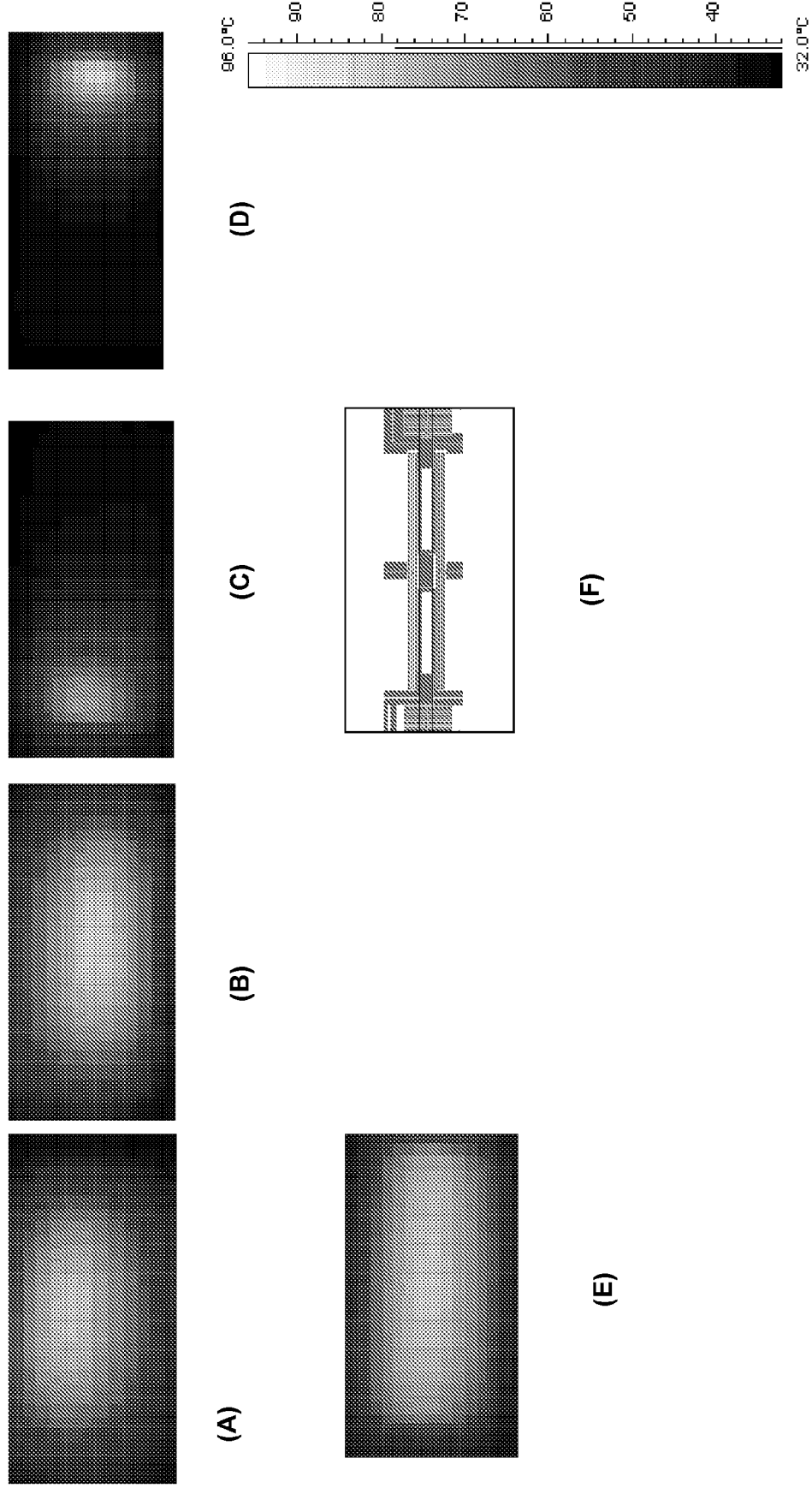
FIG. 5C shows thermal images of heater circuitry in operation.

Each heater can be independently controlled by a processor and/or control circuitry used in conjunction with the apparatus described herein. FIG. 5C shows thermal images, from the top surface of a microfluidic cartridge when heated by heaters configured as in FIGS. 5A and 5B, when each heater in turn is activated, as follows: (A): Long Top only; (B) Long Bottom only; (C) Short Left only; (D) Short Right only; and (E) All Four Heaters on. Panel (F) shows a view of the reaction chamber and heaters on the same scale as the other image panels in FIG. 5C. Also shown in the figure is a temperature bar.

Exemplary Microfluidic Cartridges

The multi-sample cartridge comprises at least a first microfluidic network and a second microfluidic network, adjacent to one another, wherein each of the first microfluidic network and the second microfluidic network is as elsewhere described herein, and wherein the first microfluidic network accepts the first sample, and wherein the second microfluidic network accepts the second sample.

Figure 6A:
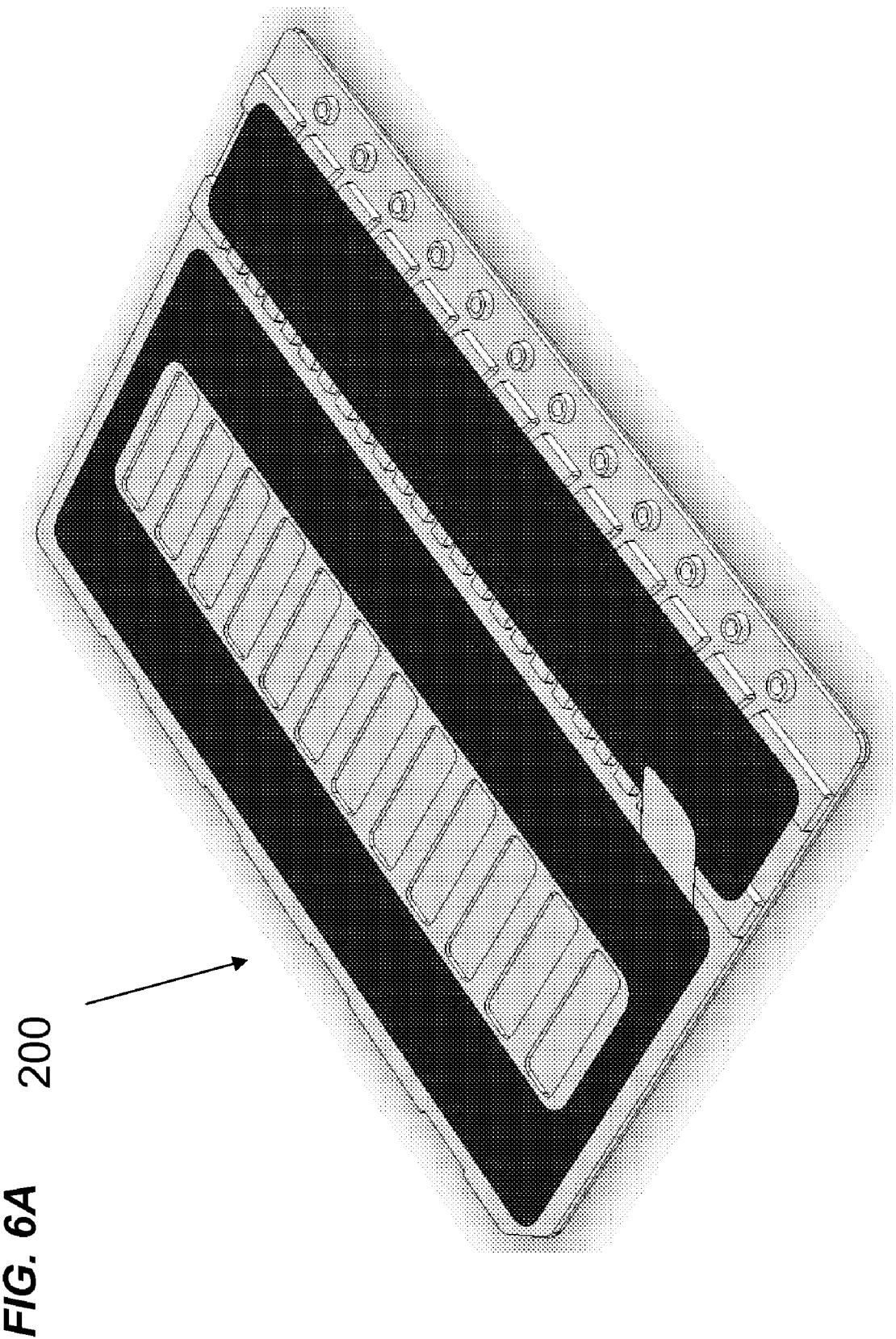
FIG. 6A shows an exemplary multi-lane cartridge.
Figure 6B:
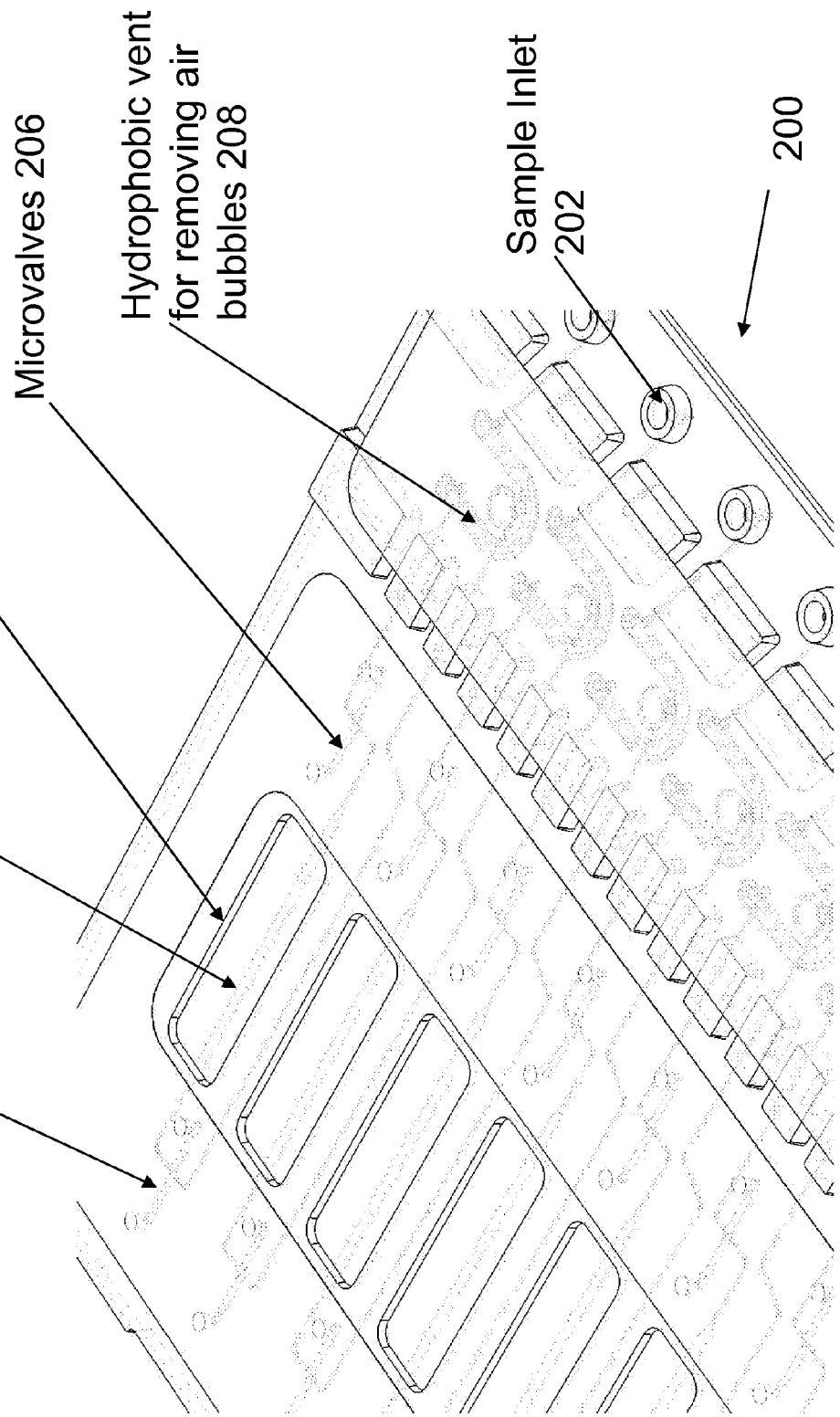
FIG. 6B shows a portion of an exemplary multi-lane cartridge.

FIG. 6A shows a perspective view of a portion of an exemplary microfluidic cartridge 200 for use with a heater unit described herein. FIG. 6B shows a close-up view of a portion of the cartridge 200 of FIG. 6A illustrating various representative components. The cartridge 200 may be referred to as a multi-lane PCR cartridge with dedicated sample inlets 202. For example sample inlet 202 is configured to accept a liquid transfer member (not shown) such as a syringe, a pipette, or a PCR tube containing a PCR ready sample. More than one inlet 202 is shown in FIGS. 6A, 6B, wherein one inlet operates in conjunction with a single sample lane. Various components of microfluidic circuitry in each lane are also visible. For example, microvalves 204, and 206, and vents 208, are parts of microfluidic circuitry in a given lane. Also shown is an ultrafast PCR reactor 210, which, as further described herein, is a microfluidic channel in a given sample lane that is long enough to permit PCR to amplify polynucleotides present in a sample. Above each PCR reactor 210 is a window 212 that permits detection of fluorescence from a fluorescent substance in PCR reactor 210 when a detector is situated above window 212. It is to be understood that other configurations of windows are possible including, but not limited to, a single window that straddles each PCR reactor across the width of cartridge 200.

In preferred embodiments, the multi-sample cartridge has a size substantially the same as that of a 96-well plate as is customarily used in the art. Advantageously, then, the cartridge may be used with plate handlers used elsewhere in the art.

The sample inlets of adjacent lanes are reasonably spaced apart from one another to prevent any contamination of one sample inlet from another sample when a user introduces a sample into any one cartridge. In an embodiment, the sample inlets are configured so as to prevent subsequent inadvertent introduction of sample into a given lane after a sample has already been introduced into that lane.

In certain embodiments, the multi-sample cartridge is designed so that a spacing between the centroids of sample inlets is 9 mm, which is an industry-recognized standard. This means that, in certain embodiments the center-to-center distance between inlet holes in the cartridge that accept samples from PCR tubes, as further described herein, is 9 mm. The inlet holes are manufactured conical in shape with an appropriate conical angle so that industry-standard pipette tips (2 µl, 20 µl, 200 µl, volumes, etc.) fit snugly. The apparatus herein may be adapted to suit other, later-arising, industry standards not otherwise described herein.

Figure 7:
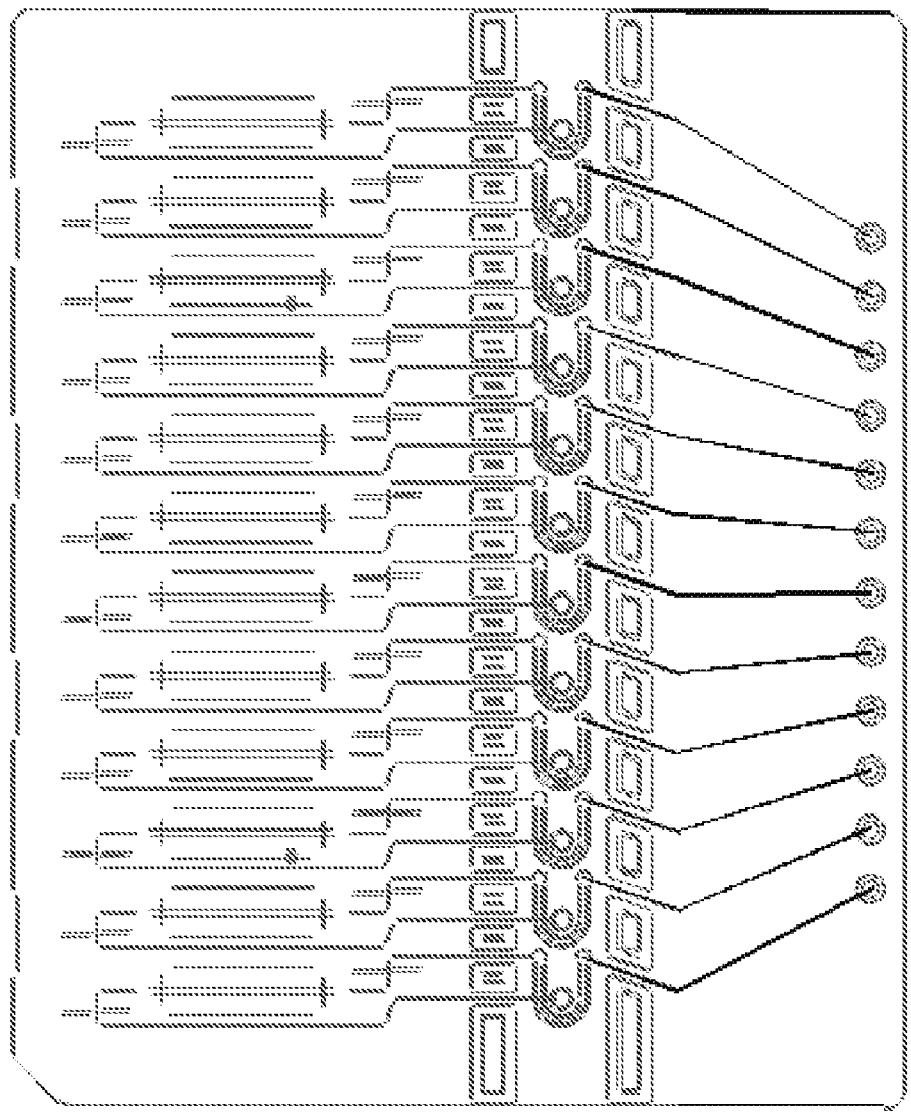
FIG. 7 shows a plan view of an exemplary multi-lane microfluidic cartridge.

FIG. 7 shows a plan view of an exemplary microfluidic cartridge 700 having 12 lanes. The inlet ports 702 have a 6 mm spacing, so that, when used in conjunction with an automated sample loader having 4 heads, spaced equidistantly at 18 mm apart, the inlets can be loaded in three batches of 4 inlets: e.g., inlets 1, 4, 7, and 10 together, followed by 2, 5, 8, and 11, then finally 3, 6, 9, and 12, wherein the 12 inlets are numbered consecutively from one side of the cartridge to the other.

Figure 8:
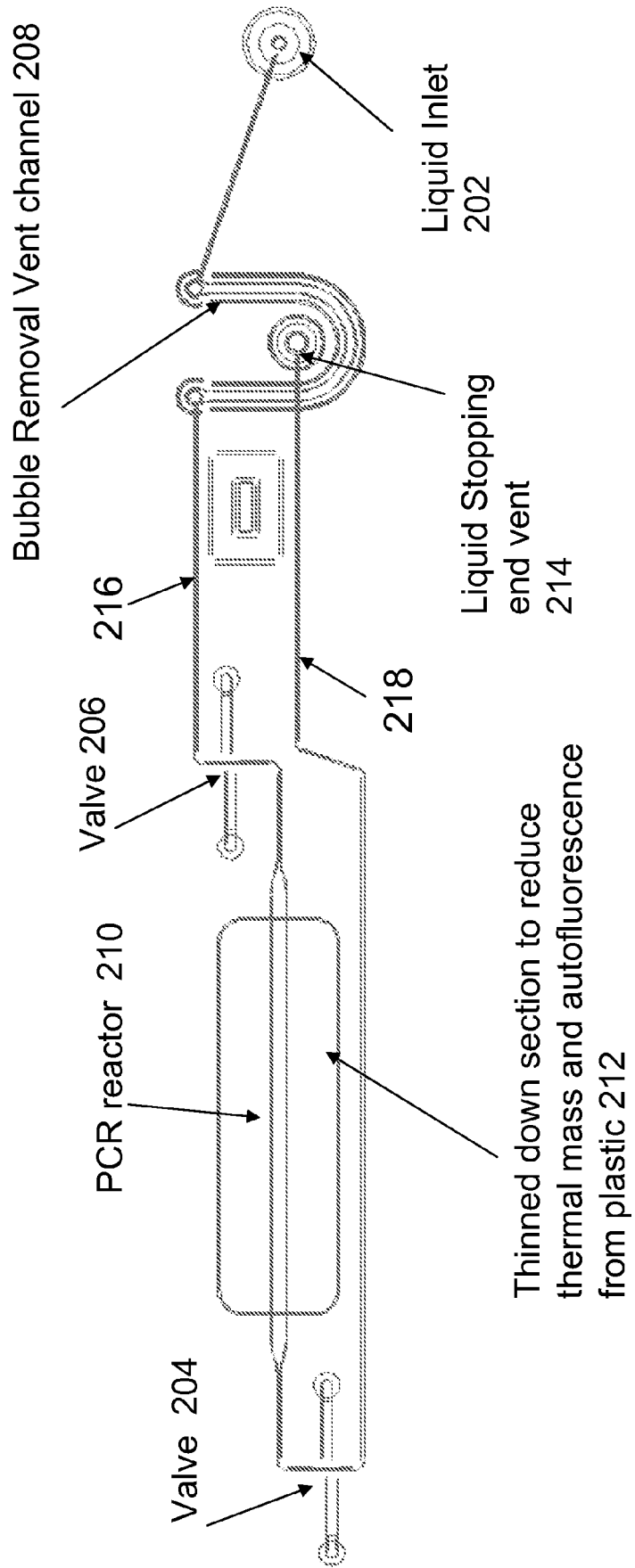
FIG. 8 shows an exemplary microfluidic network in a lane of a multi-lane cartridge.

FIG. 8 shows a plan view of a representative microfluidic circuit found in one lane of a multi-lane cartridge such as shown in FIGS. 6A, 6B and 7. Other configurations of microfluidic network would be consistent with the function of the cartridges and apparatus described herein. In sequence, sample is introduced through liquid inlet 202, flows into a bubble removal vent channel 208 (which permits adventitious air bubbles introduced into the sample during entry, to escape), and continues along a channel 216. Throughout the operation of cartridge 200 the fluid is manipulated as a microdroplet (not shown in FIG. 5), and the various microfluidic components are actuated or controlled by application of heat from the heater unit further described herein. Valves 204 and 206 are initially open, so that a microdroplet of sample-containing fluid can be pumped into PCR reactor channel 210 from inlet hole 202 under influence of force from the sample injection operation. Upon initiating of processing, the detector present on top of the PCR reactor checks for the presence of liquid in the PCR channel, and then closes valves 204 and 206 to isolate the PCR reaction mix from the outside.

The reactor 210 is a microfluidic channel that is heated through a series of cycles to carry out amplification of nucleotides in the sample, as further described herein. Both valves 204 and 206 are closed prior to thermocycling to prevent any evaporation of liquid, bubble generation, or movement of fluid from the PCR reactor. End vent 214 prevents a user from introducing any excess amount of liquid into the microfluidic cartridge, as well as playing a role of containing any sample from spilling over to unintended parts of the cartridge. A user may input sample volumes as small as an amount to fill from the bubble removal vent to the middle of the microreactor, or up to valve 204 or beyond valve 204. The use of microvalves prevents both loss of liquid or vapor thereby enabling even a partially filled reactor to successfully complete a PCR thermocycling reaction. The application of pressure to contact the cartridge to the heater unit assists in achieving better thermal contact between the heater and the heat-receivable parts of the cartridge, and also prevents the bottom laminate structure from expanding, as would happen if the PCR channel was partially filled with liquid and the entrapped air would be thermally expanded during thermocycling.

Further aspects of a microfluidic cartridge that adapt it to carrying out PCR efficiently are described in U.S. patent application Ser. No. 11/940,310, entitled "Microfluidic Cartridge and Method of Making Same" and filed on even date herewith.

Figure 9A:
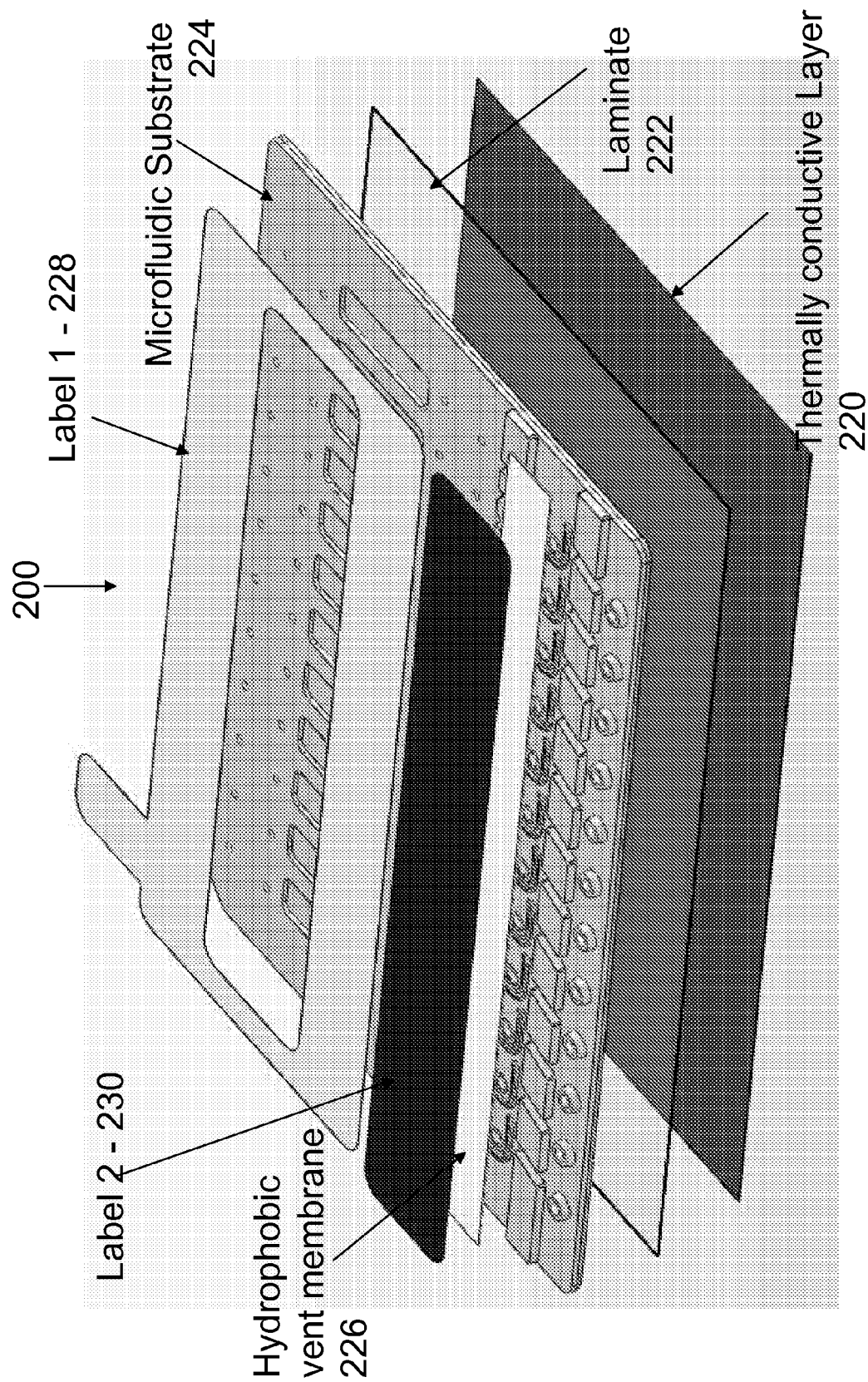
FIGS. 9A-C show a layer structure of an exemplary microfluidic cartridge.
Figure 9B:
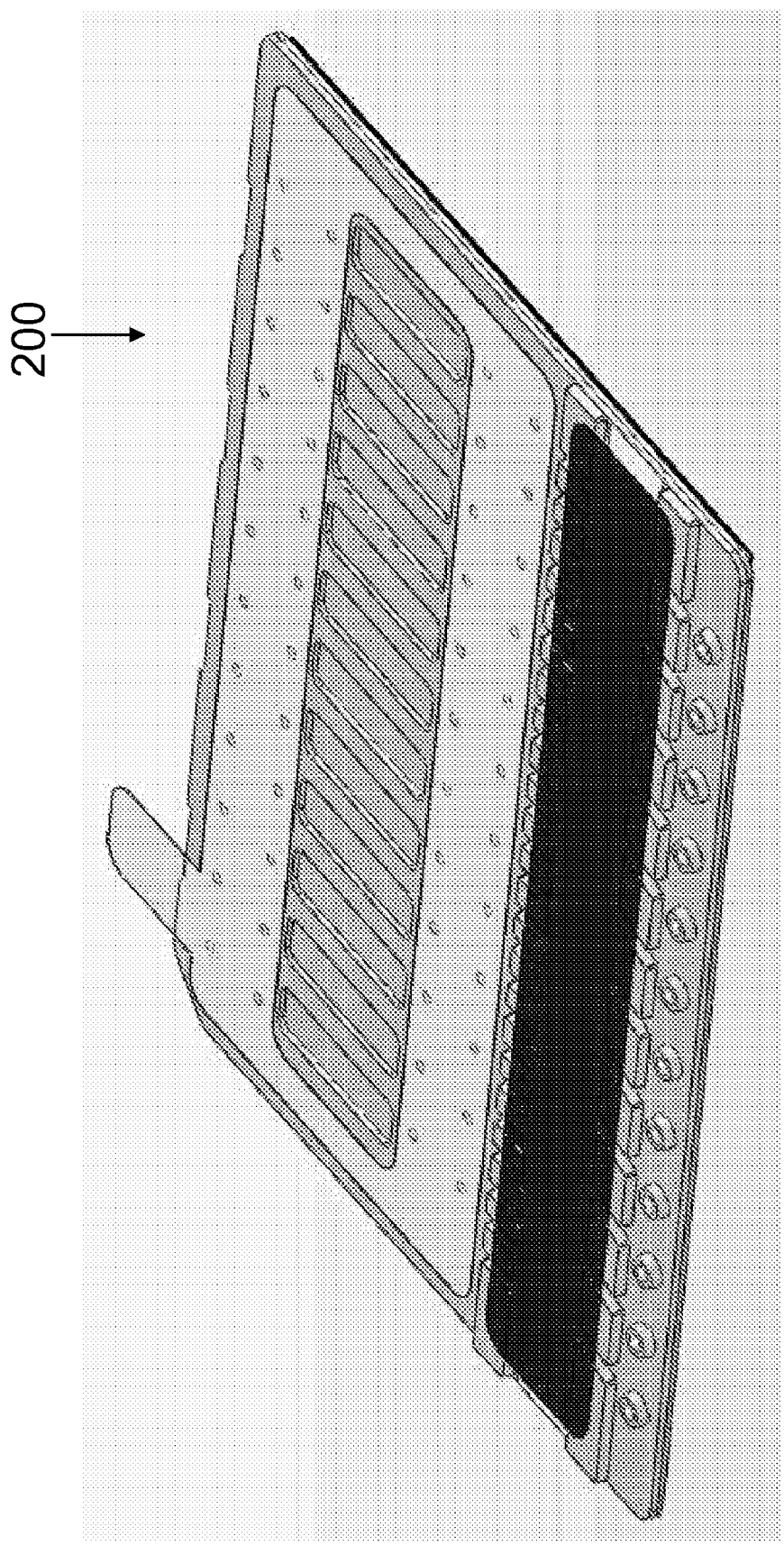
Figure 9C:
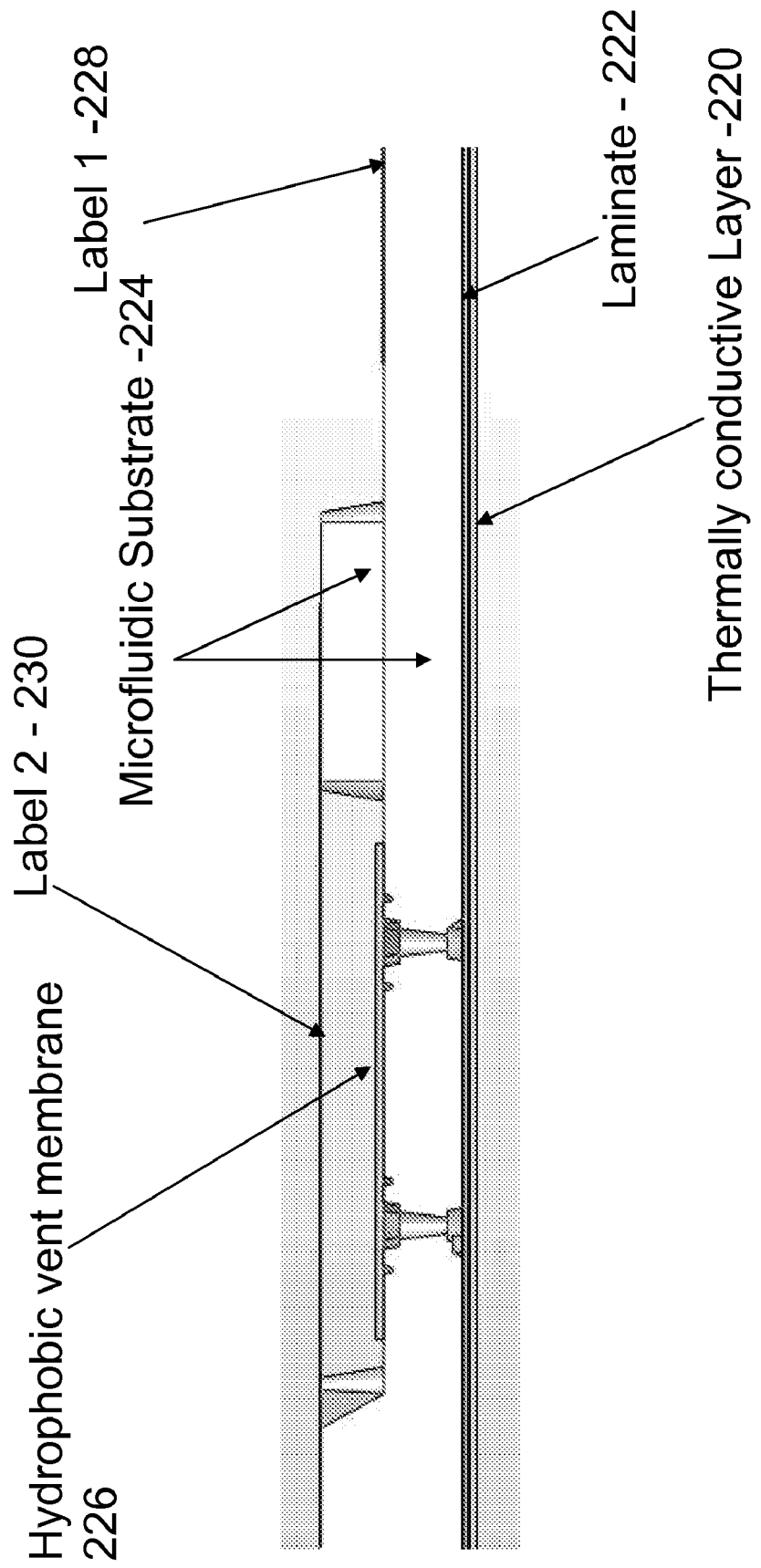

FIGS. 9A-C show various views of an exemplary microfluidic cartridge as further described herein. FIG. 9A shows an exploded view; FIG. 9B shows a perspective view; and FIG. 9C shows a cross-sectional view. Referring to FIGS. 9A-C, an exemplary microfluidic cartridge 200 includes first 220, second 222, third 224, fourth 226, and fifth layers 228, 230 (as shown) that enclose a microfluidic network having various components configured to process multiple samples in parallel that include one or more polynucleotides to be determined.

Microfluidic cartridge 200 can be fabricated as desired, for example, according to methods described in U.S. patent application Ser. No. 11/940,310, entitled "Microfluidic Cartridge and Method of Making Same" and filed on even date herewith. Typically, the microfluidic cartridge layer includes a layer 228,230 of polypropylene or other plastic label with pressure sensitive adhesive (typically between about 50 and 150 microns thick) configured to seal the wax loading holes of the valves, trap air used for valve actuation, and serve as a location for operator markings. In FIG. 29A, this layer is shown in two separate pieces, 228, 230, though it would be understood by one of ordinary skill in the art that a single piece layer would be appropriate.

The cartridge can further include a heat sealable laminate layer 222 (typically between about 100 and about 125 microns thick) attached to the bottom surface of the microfluidic substrate using, for example, heat bonding. The cartridge can further include a thermal interface material layer 220 (typically about 125 microns thick), attached to the bottom of the heat sealable laminate layer using, for example, pressure sensitive adhesive. This layer 220 can be compressible and have a higher thermal conductivity than common plastics, thereby serving to transfer heat across the membrane more efficiently to the components of the microfluidic network.

Application of minimal pressure on the cartridge: a force member on the apparatus can compress the compliant label of the cartridge. This can cause the bottom of the cartridge to be pressed down against the microheater substrate present in the heater unit. Springs, for example, present in the force member can deliver, for example approximately 50 lb of pressure to generate a minimum pressure, for example 2 psi over the entire cartridge bottom.

Thermal interface: the cartridge underside can have a layer of mechanically compliant heat transfer laminate that can enable thermal contact between the microfluidic substrate and the microheater substrate of the heater unit. A minimal pressure of 1 psi can be employed for reliable operation of the thermal valves, gate and pumps present in the microfluidic cartridge.

Table 1 outlines volumes, pumping pressures, and operation times associated with various components of a microfluidic cartridge.

TABLE 1

| Operation | Pumping Pressure | Displacement Volume | Time of Operation |
|---|---|---|---|
| Moving valve wax plugs | ~1-2 psi | <1 μl | 5-15 seconds |
| Operation | Pump Used | Pump Design | Pump Actuation |
| Moving valve wax plugs | Thermopneumatic pump | 1 μl of trapped air | Heat trapped air to ~70-90 C. |

Figure 10A:
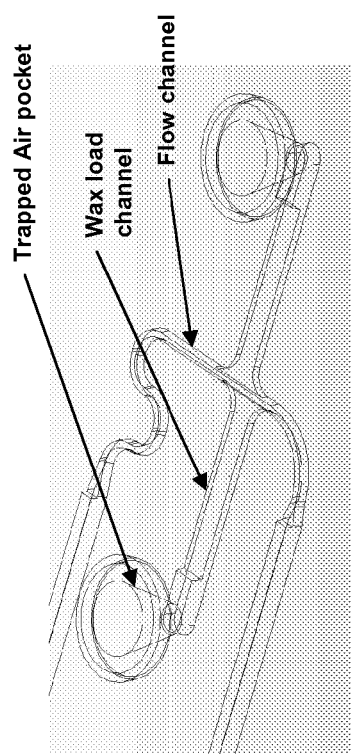
FIGS. 10A-C show exemplary configurations of microfluidic valves.
Figure 10B:
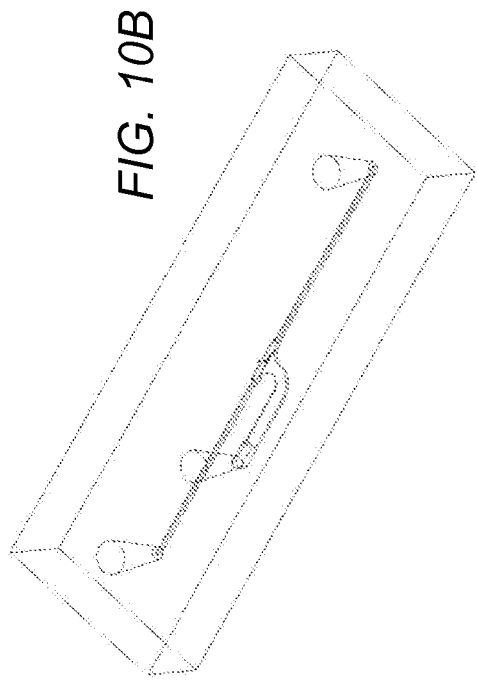
Figure 10C:
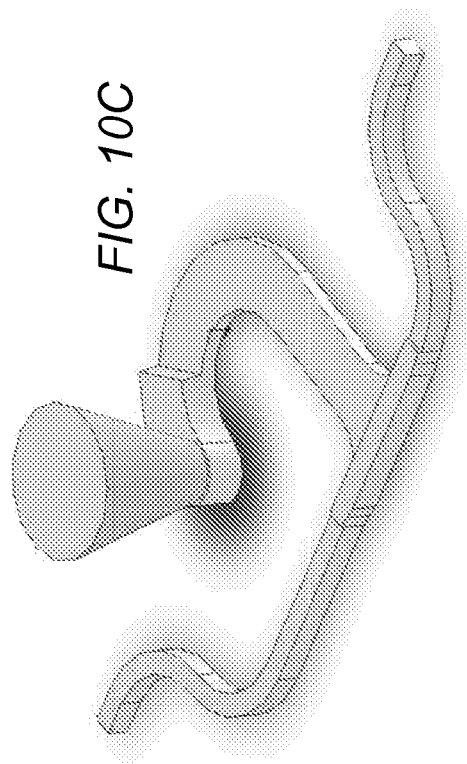

A valve (sometimes referred to herein as a microvalve) is a component in communication with a channel, such that the valve has a normally open state allowing material to pass along a channel from a position on one side of the valve (e.g., upstream of the valve) to a position on the other side of the valve (e.g., downstream of the valve). Upon actuation of the valve, the valve transitions to a closed state that prevents material from passing along the channel from one side of the valve to the other. For example, in one embodiment, a valve can include a mass of a thermally responsive substance (TRS) that is relatively immobile at a first temperature and more mobile at a second temperature. The first and second temperatures are insufficiently high to damage materials, such as polymer layers of a microfluidic cartridge in which the valve is situated. A mass of TRS can be an essentially solid mass or an agglomeration of smaller particles that cooperate to obstruct the passage. Examples of TRS's include a eutectic alloy (e.g., a solder), wax (e.g., an olefin), polymers, plastics, and combinations thereof. Generally, for such a valve, the second temperature is less than about 90° C. and the first temperature is less than the second temperature (e.g., about 70° C. or less). A chamber is in gaseous communication with the mass of TRS. Upon heating gas (e.g., air) in the chamber and heating the mass of TRS to the second temperature, gas pressure within the chamber moves the mass into the channel obstructing material from passing therealong. Various exemplary valves are shown in FIGS. 10A-10C.

Highly Multiplexed Cartridge Embodiments

Embodiments of the microfluidic substrate described herein may be constructed that have high-density microfluidic circuitry on a single substrate that thereby permit processing of multiple samples in parallel, or in sequence, on a single cartridge. Preferred numbers of such multiple samples include 24, 36, 40, 48, 50, 60, 64, 72, 80, 84, 96, and 100, but it would be understood that still other numbers are consistent with the technology herein, where deemed convenient and practical.

Accordingly, different configurations of lanes, sample inlets, and associated heater networks than those explicitly depicted in the FIGs that can facilitate processing such numbers of samples on a single substrate are within the scope of the instant disclosure. Similarly, alternative configurations of detectors and heating elements for use in conjunction with such a highly multiplexed substrate are also within the scope of the description herein.

Accordingly, it is to be understood that the microfluidic substrates and cartridges described herein are not to be limited to rectangular shapes, but can include cartridges having circular, elliptical, triangular, rhombohedral, square, and other shapes. Such shapes may also be adapted to include some irregularity, such as a cut-out, to facilitate exact placement of a cartridge in a complementary apparatus as further described herein.

Figure 11:
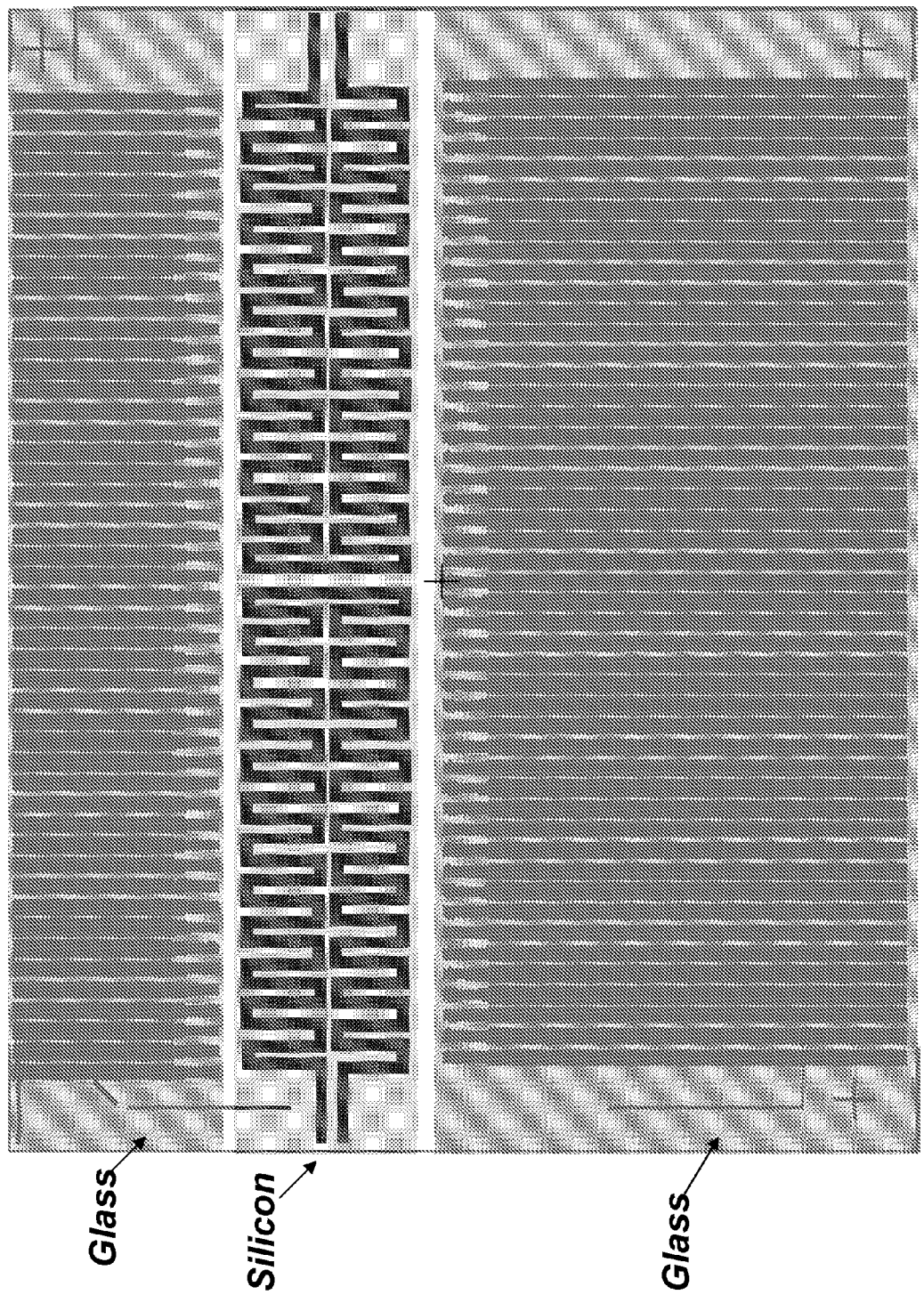
FIG. 11 shows an exemplary highly-multiplexed microfluidic cartridge.

In an exemplary embodiment, a highly multiplexed cartridge has 48 sample lanes, and permits independent control of each valve in each lane by suitably configured heater circuitry, with 2 banks of thermocycling protocols per lane, as shown in FIG. 11. In the embodiment in FIG. 11, the heaters (shown superimposed on the lanes) are arranged in three arrays. The heaters are themselves disposed within one or more substrates. Heater arrays 502, 508 in two separate glass regions only apply heat to valves in the microfluidic networks in each lane. Because of the low thermal conductivity of glass, the individual valves may be heated separately from one another. This permits samples to be loaded into the cartridge at different times, and passed to the PCR reaction chambers independently of one another. The PCR heaters 504, 506 are mounted on a silicon substrate—and are not readily heated individually, but thereby permit batch processing of PCR samples, where multiple samples from different lanes are amplified by the same set of heating/cooling cycles. It is preferable for the PCR heaters to be arranged in 2 banks (the heater arrays on the left 506 and right 508 are not in electrical communication with one another), thereby permitting a separate degree of sample control.

Figure 12:
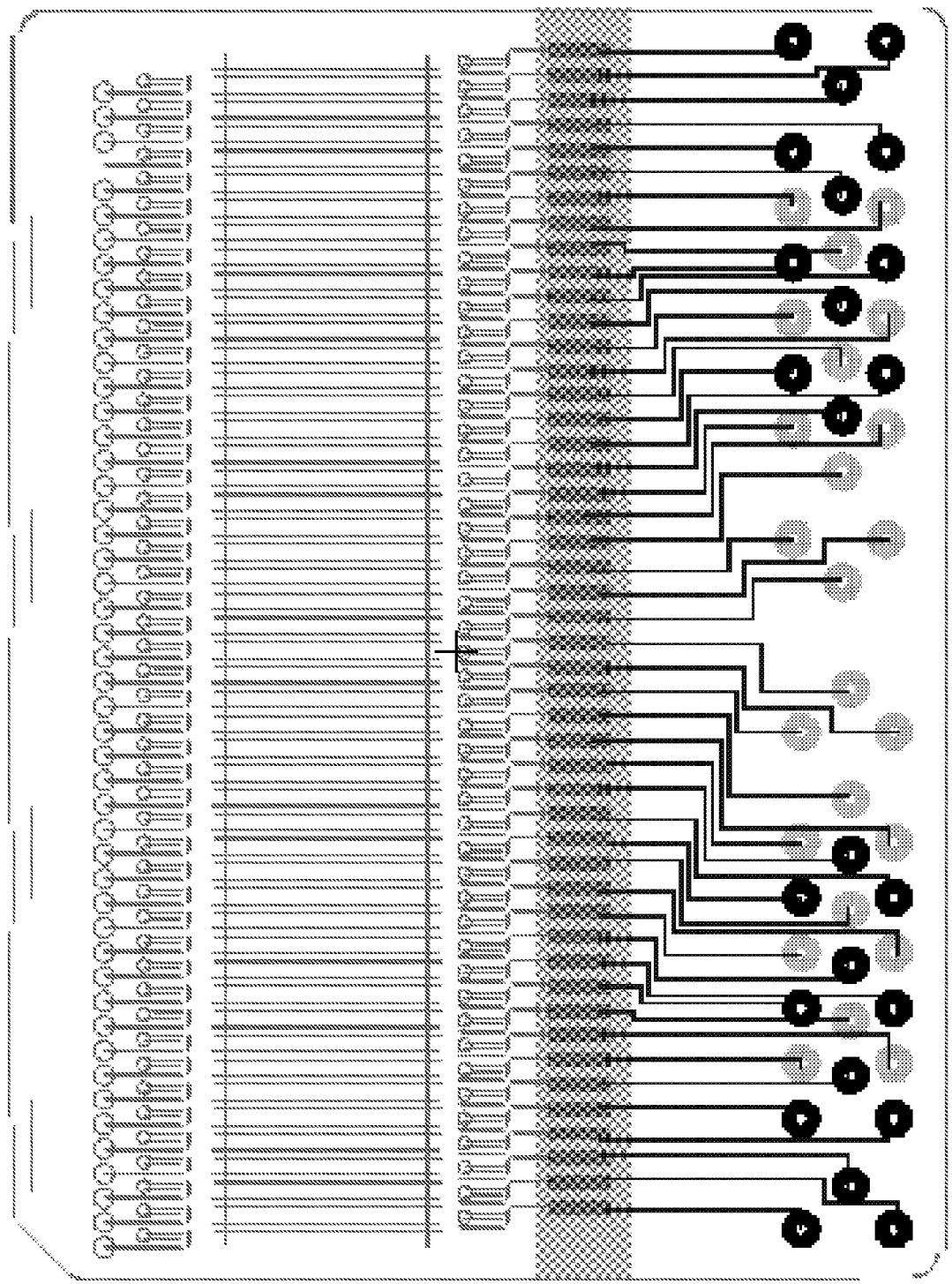
FIGS. 12-15 show various aspects of exemplary highly multiplexed microfluidic cartridges.

FIG. 12 shows a representative 48-sample cartridge compatible with the heater arrays of FIG. 11, and having a configuration of inlets different to that depicted on cartridges herein. The inlet configuration is exemplary and has been designed to maximize efficiency of space usage on the cartridge. The inlet configuration can be compatible with an automatic pipetting machine that has dispensing heads situated at a 9 mm spacing. For example, such a machine having 4 heads can load 4 inlets at once, in 12 discrete steps, for the cartridge of FIG. 12. Other configurations of inlets though not explicitly described or depicted are compatible with the technology described herein.

Figure 13:
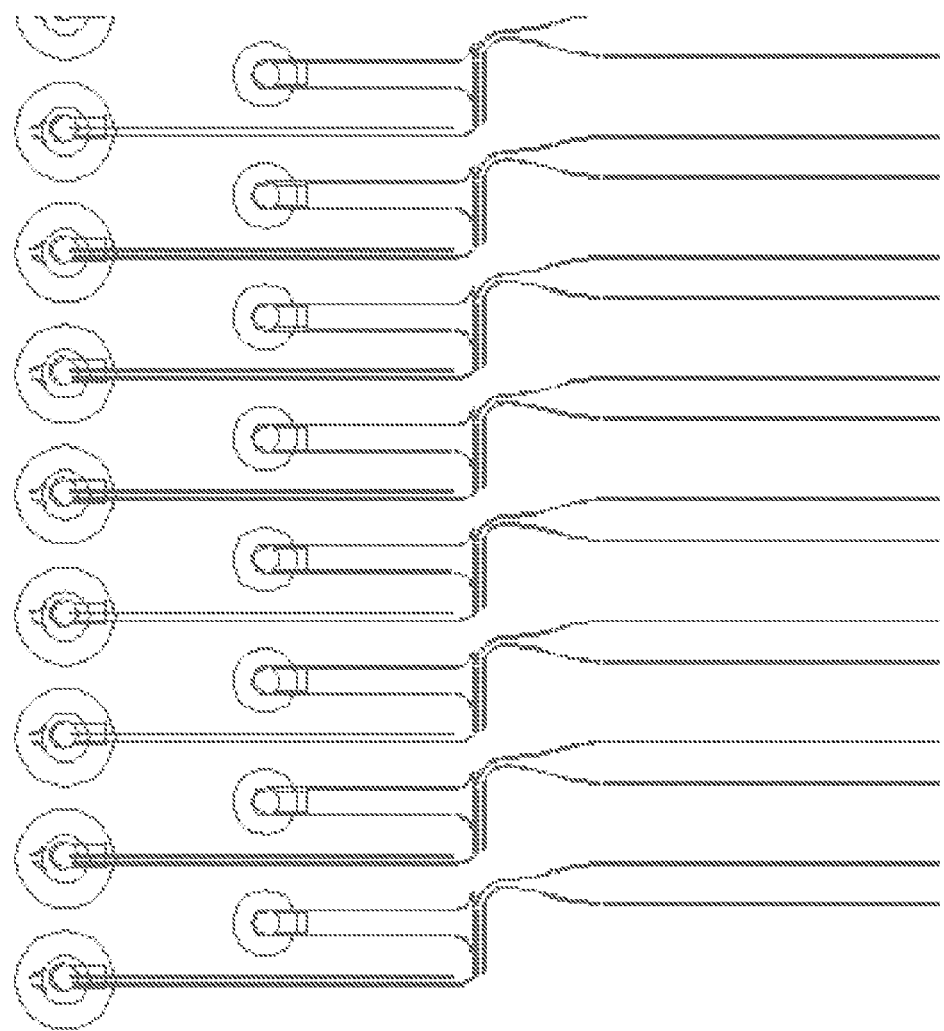

FIG. 13 shows, in close up, an exemplary spacing of valves and channels in adjacent lanes of a multi-sample microfluidic cartridge, for example as shown in FIG. 9.

Figure 14:
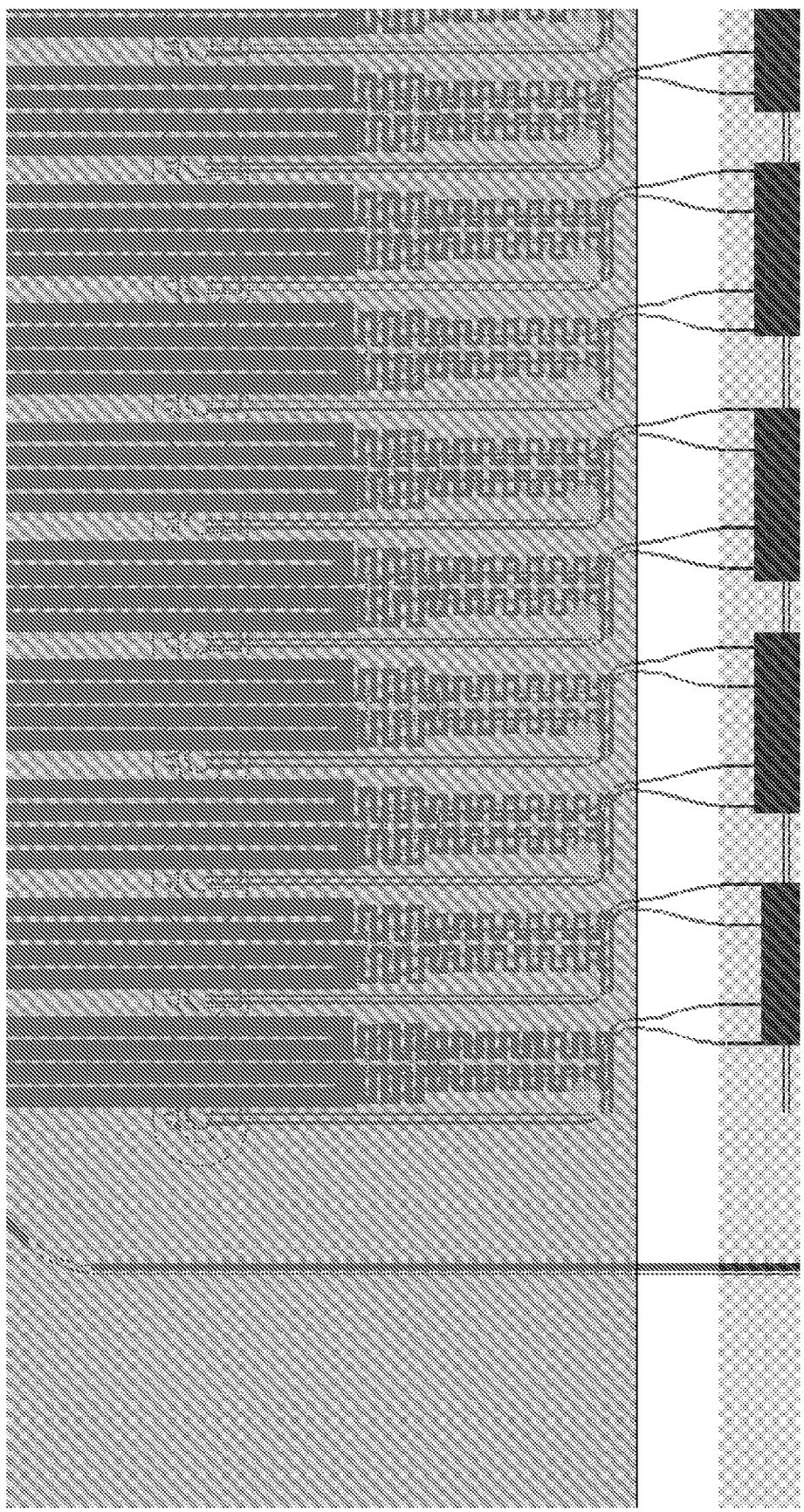
Figure 15:
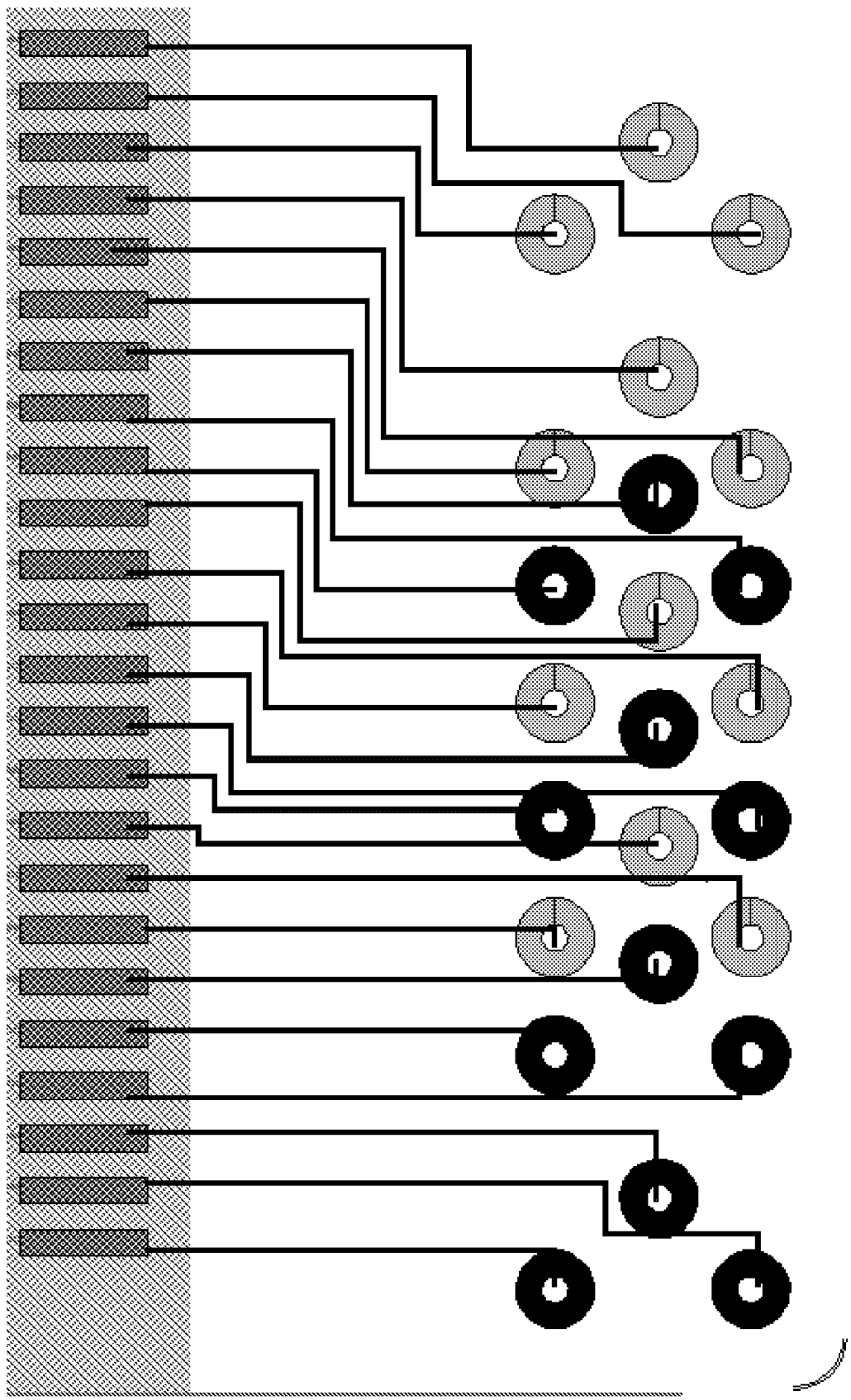

FIGS. 14 and 15 show close-ups of, respectively, heater arrays compatible with, and inlets on the exemplary cartridge shown in FIG. 9.

Figure 16A:
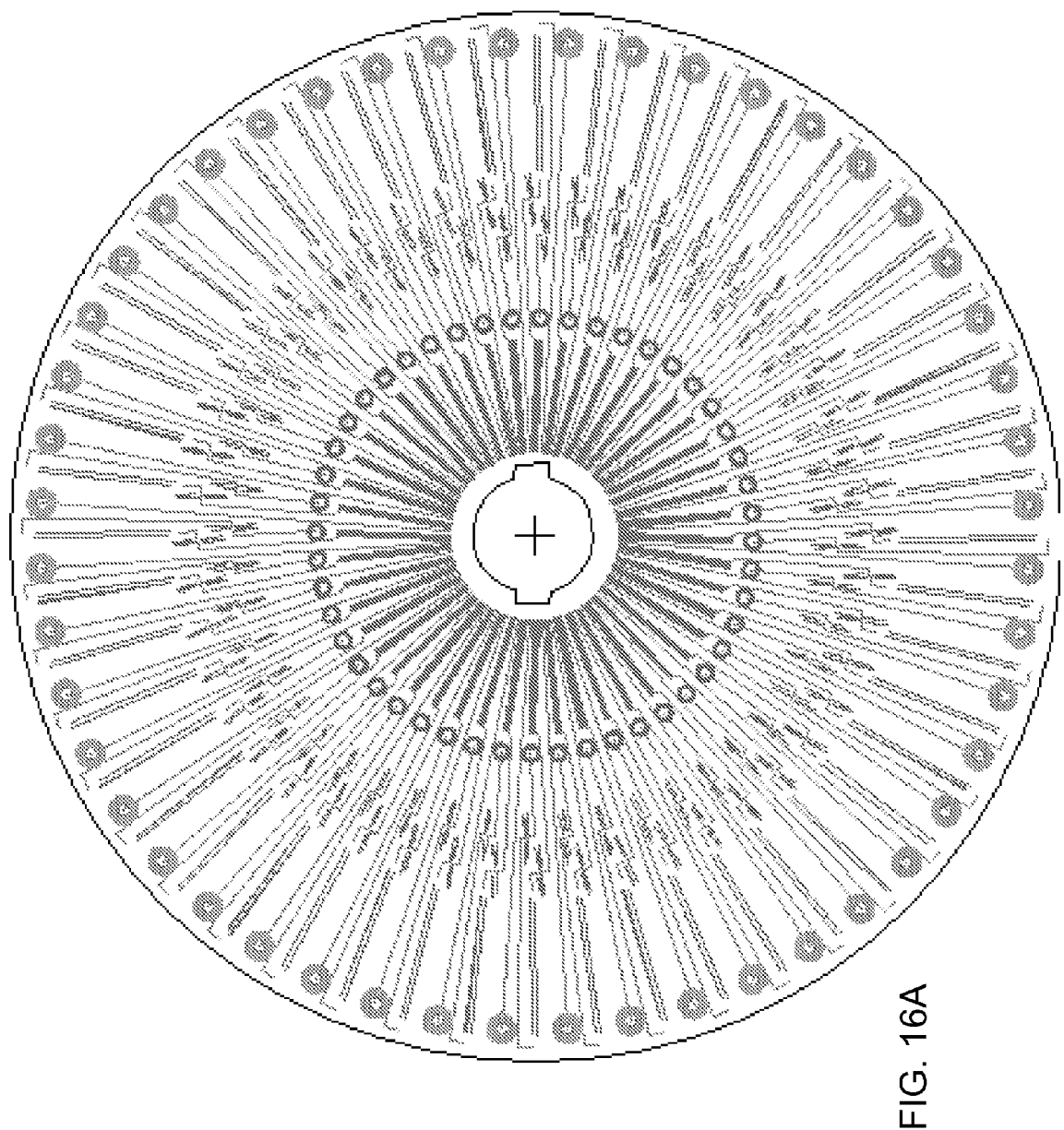
FIGS. 16A-C show various aspects of a radially configured highly multiplexed microfluidic cartridge.
Figure 16B:
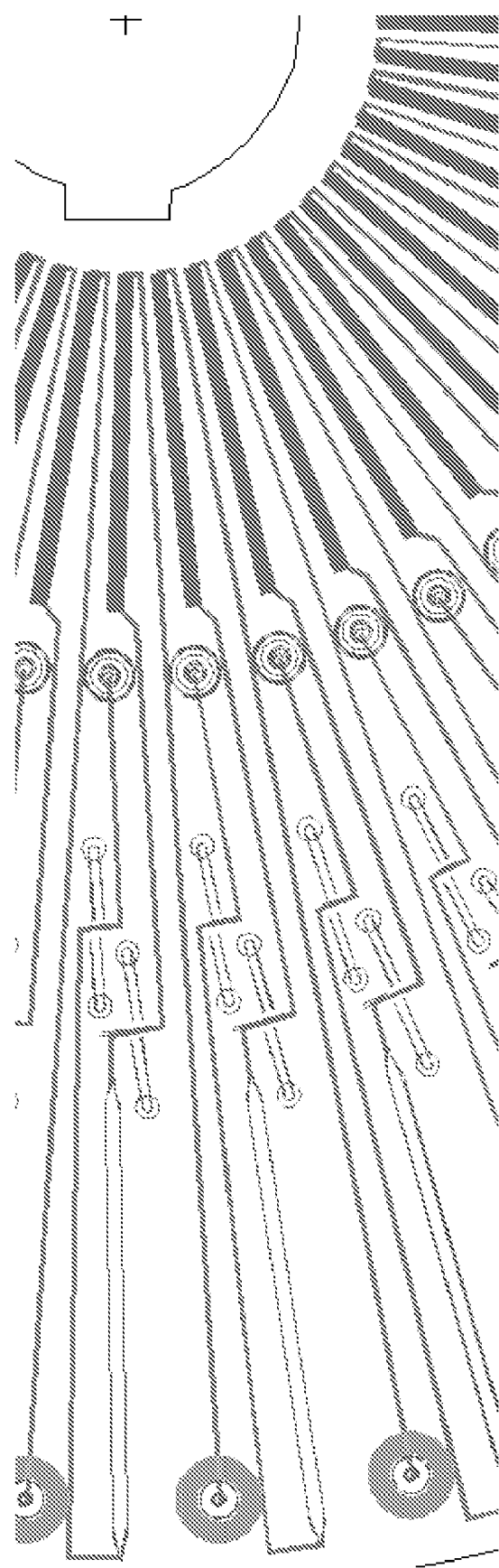
Figure 16C:
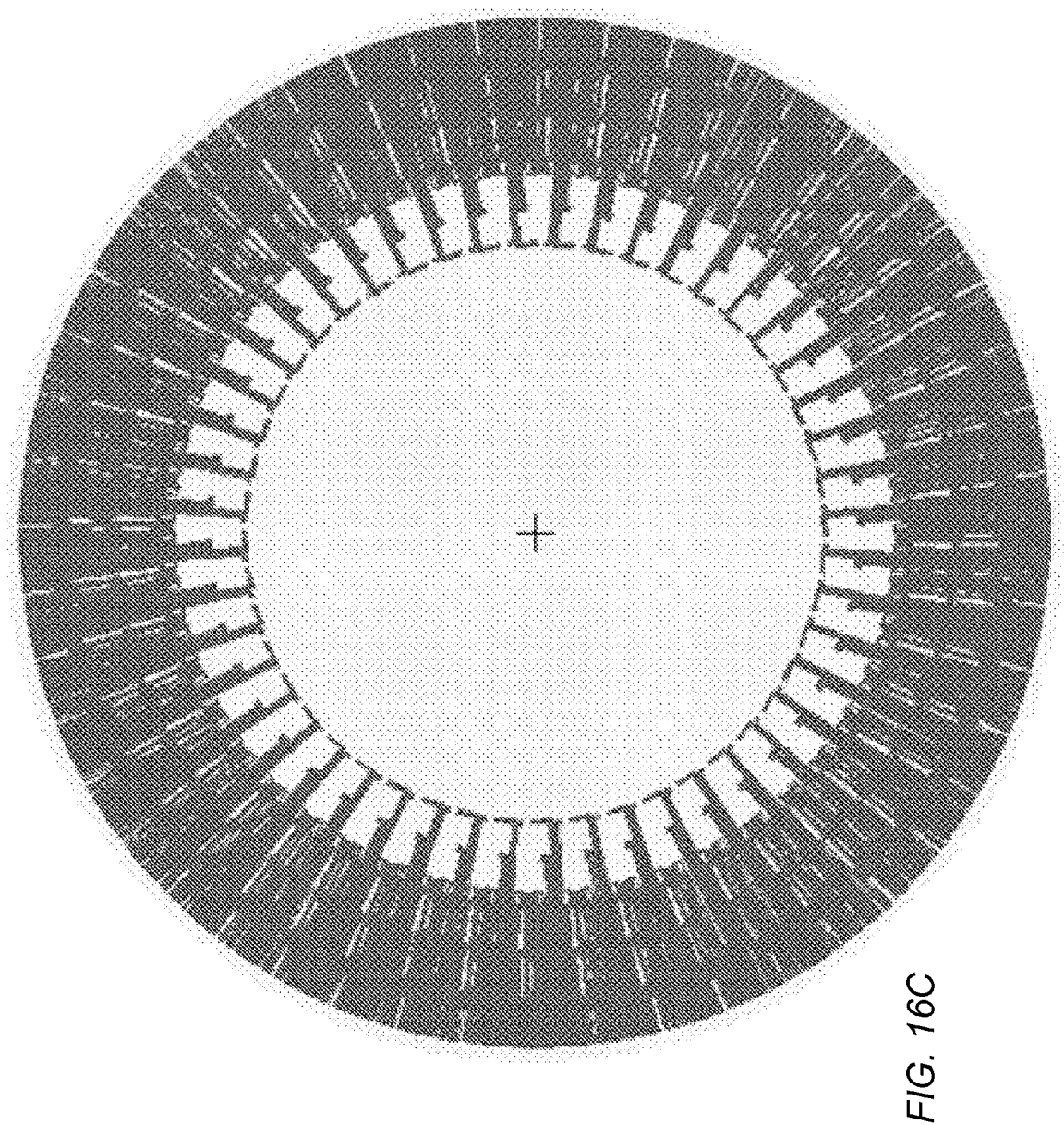

FIGS. 16A and 16B show various views of an embodiment of a radially-configured highly-multiplexed cartridge, having a number of inlets, microfluidic lanes, valves and PCR reaction chambers. FIG. 16C shows an array of heater elements compatible with the cartridge layout of FIG. 16A.

The various embodiments shown in FIGS. 11-16C are compatible with liquid dispensers, receiving bays, and detectors that are configured differently from the other specific examples described herein.

Use of Cutaways in Cartridge and Substrate to Improve Rate of Cooling During PCR Cycling During a PCR amplification of a nucleotide sample, a number of thermal cycles are carried out. For improved efficiency, the cooling between each application of heat is preferably as rapid as possible. Improved rate of cooling can be achieved with various modifications to the heating substrate, as shown in FIGS. 17A-17C.

Figure 17A:
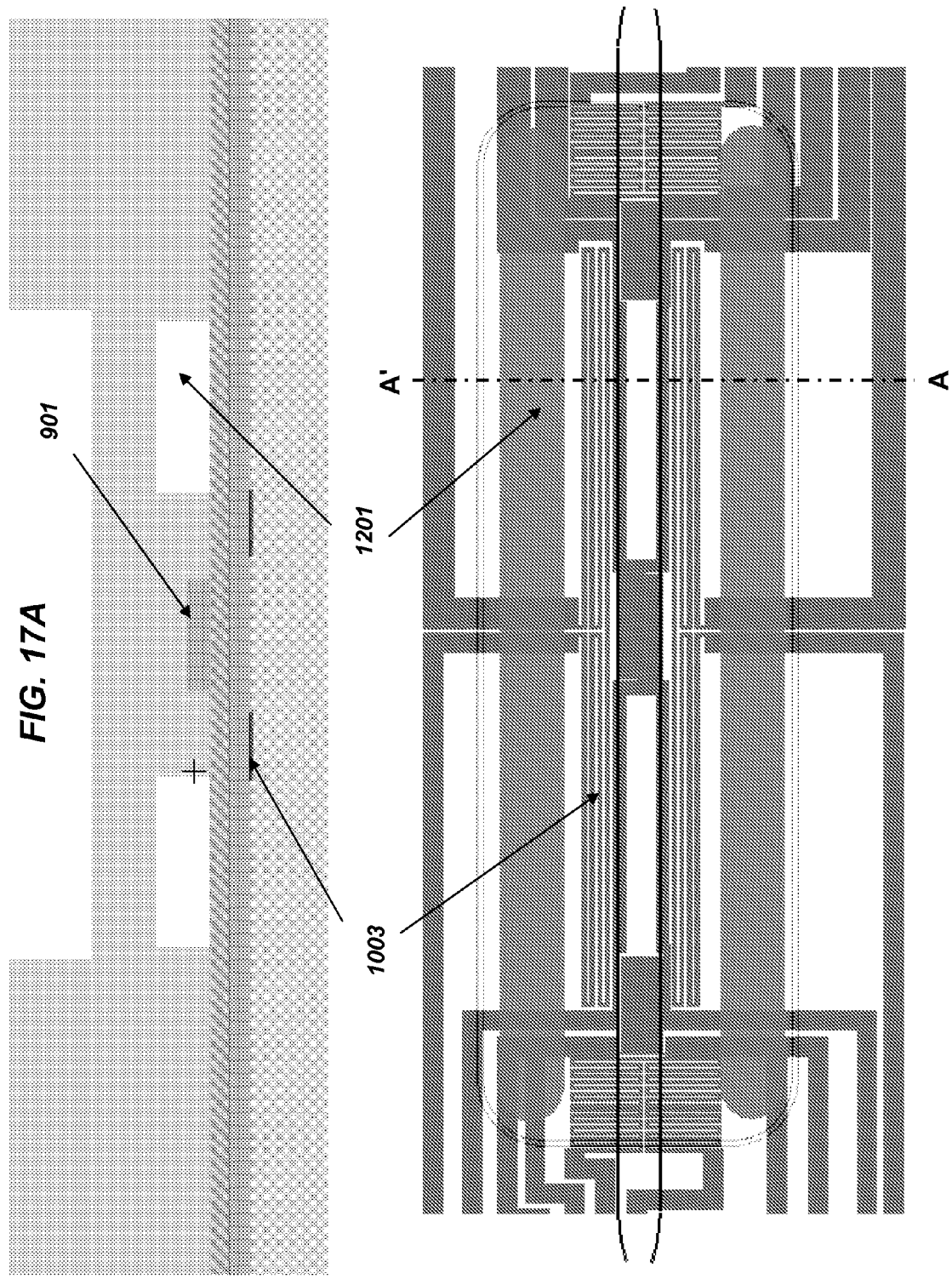
FIGS. 17A-17C shows various cut-away sections that can be used to improve cooling rates during PCR thermal cycling.

One way to achieve rapid cooling is to cutaway portions of the microfluidic cartridge substrate, as shown in FIG. 17A. The upper panel of FIG. 17A is a cross-section of an exemplary microfluidic cartridge taken along the dashed line A-A' as marked on the lower panel of FIG. 17A. PCR reaction chamber 901, and representative heaters 1003 are shown. Also shown are two cutaway portions, one of which labeled 1201, that are situated alongside the heaters that are positioned along the long side of the PCR reaction chamber. Cutaway portions such as 1201 reduce the thermal mass of the cartridge, and also permit air to circulate within the cutaway portions. Both of these aspects permit heat to be conducted away quickly from the immediate vicinity of the PCR reaction chamber. Other configurations of cutouts, such as in shape, position, and number, are consistent with the present technology.

Figure 17B:
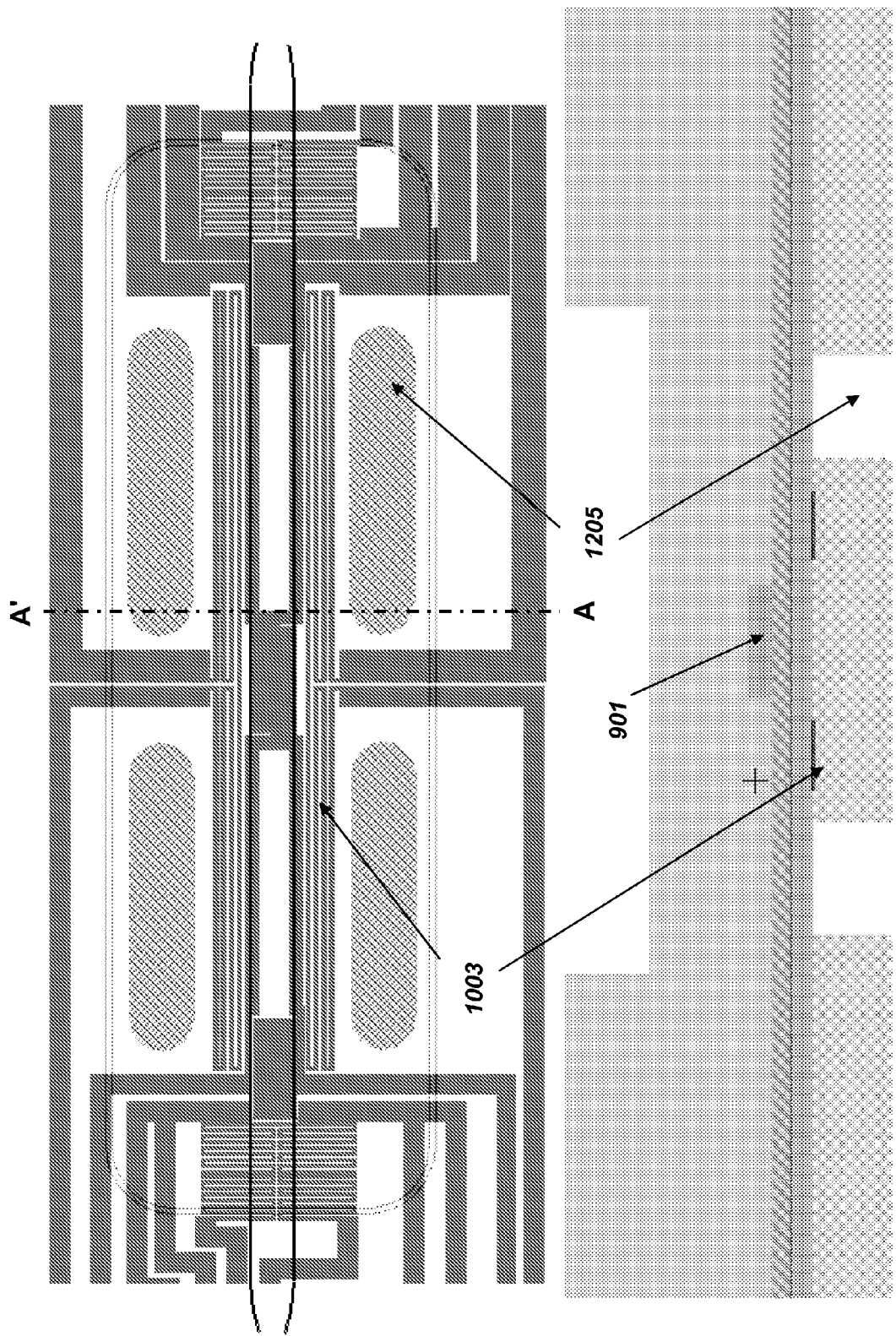

Another way to achieve rapid cooling is to cutaway portions of the heater substrate, as shown in FIG. 17B. The lower panel of FIG. 17B is a cross-section of an exemplary microfluidic cartridge and heater substrate taken along the dashed line A-A' as marked on the upper panel of FIG. 17B. PCR reaction chamber 901, and representative heaters 1003 are shown. Also shown are four cutaway portions, one of which labeled 1205, that are situated alongside the heaters that are situated along the long side of the PCR reaction chamber. Cutaway portions such as 1205 reduce the thermal mass of the heater substrate, and also permit air to circulate within the cutaway portions. Both of these aspects permit heat to be conducted away quickly from the immediate vicinity of the PCR reaction chamber. Four separate cutaway portions are shown in FIG. 17B so that control circuitry to the various heaters is not disrupted. Other configurations of cutouts, such as in shape, position, and number, are consistent with the present technology. These cutouts may be created by a method selected from: selective etching using wet etching processes, deep reactive ion etching, selective etching using $CO_2$ laser or femtosecond laser (to prevent surface cracks or stress near the surface), selective mechanical drilling, selective ultrasonic drilling, or selective abrasive particle blasting. Care has to be taken to maintain mechanically integrity of the heater while reducing as much material as possible.

Figure 17C:
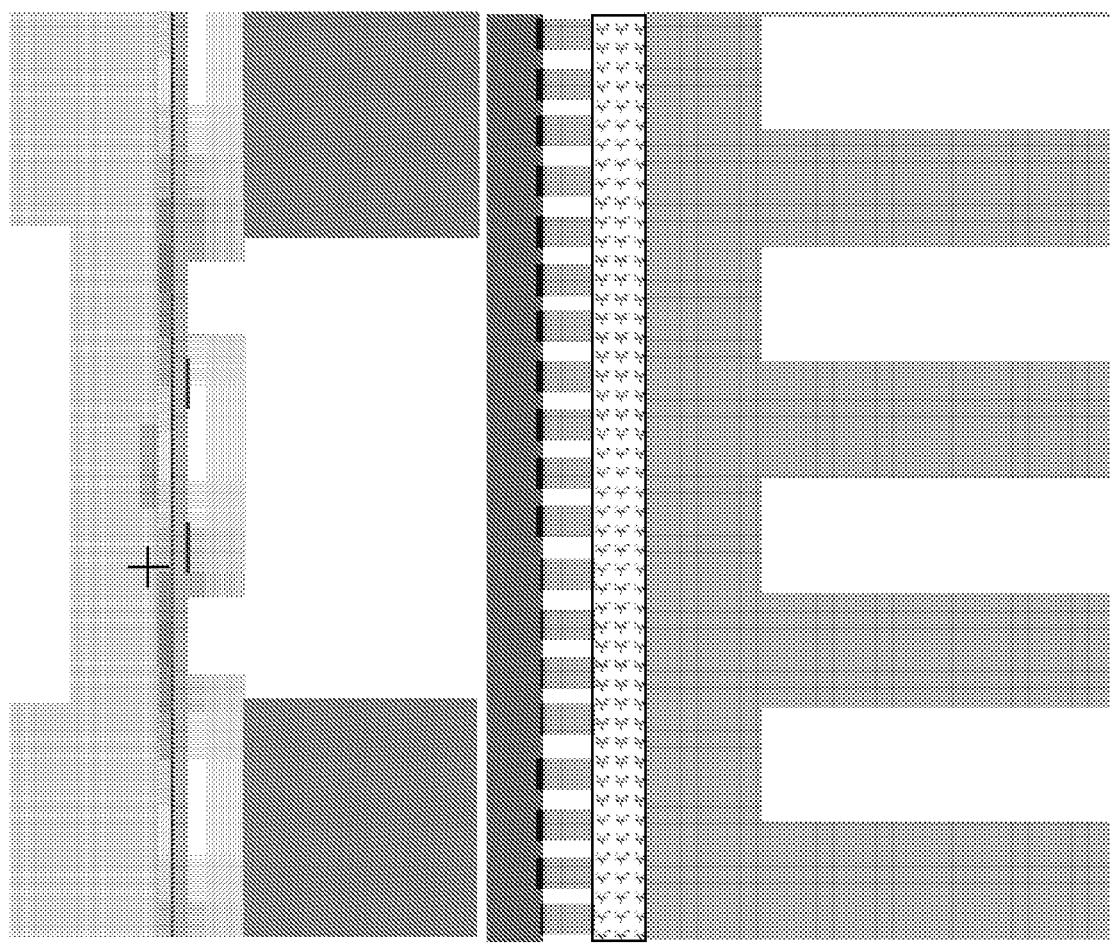

FIG. 17C shows a combination of cutouts and use of ambient air cooling to increase the cooling rate during the cooling stage of thermocycling. A substantial amount of cooling happens by convective loss from the bottom surface of the heater surface to ambient air. The driving force for this convective loss is the differential in temperatures between the glass surface and the air temperature. By decreasing the ambient air temperature by use of, for example, a peltier cooler, the rate of cooling can be increased. The convective heat loss may also be increased by keeping the air at a velocity higher than zero.

Figure 18:
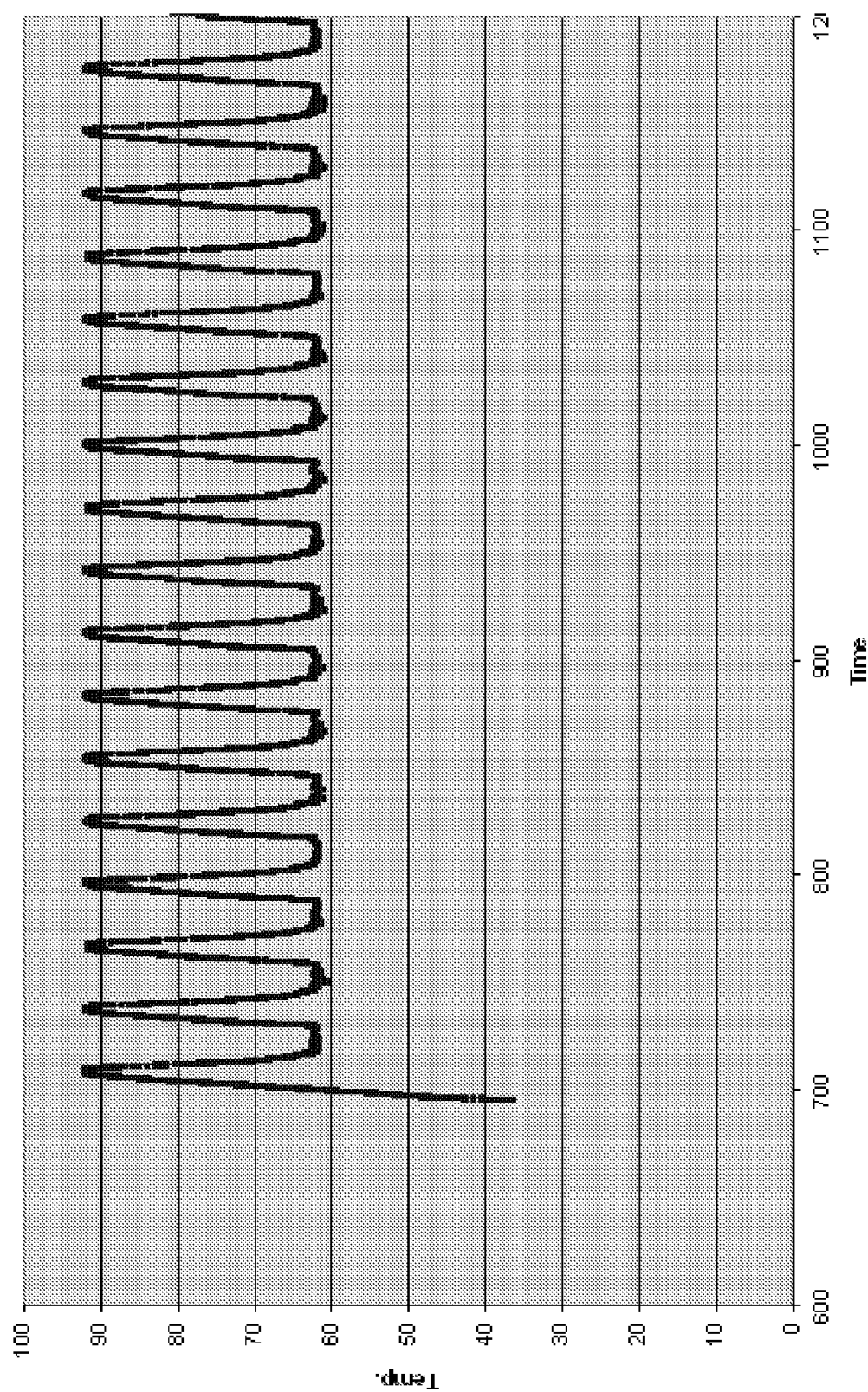
FIG. 18 shows a plot of temperature against time during a PCR process, as performed on a microfluidic cartridge as described herein.
Figure 19:
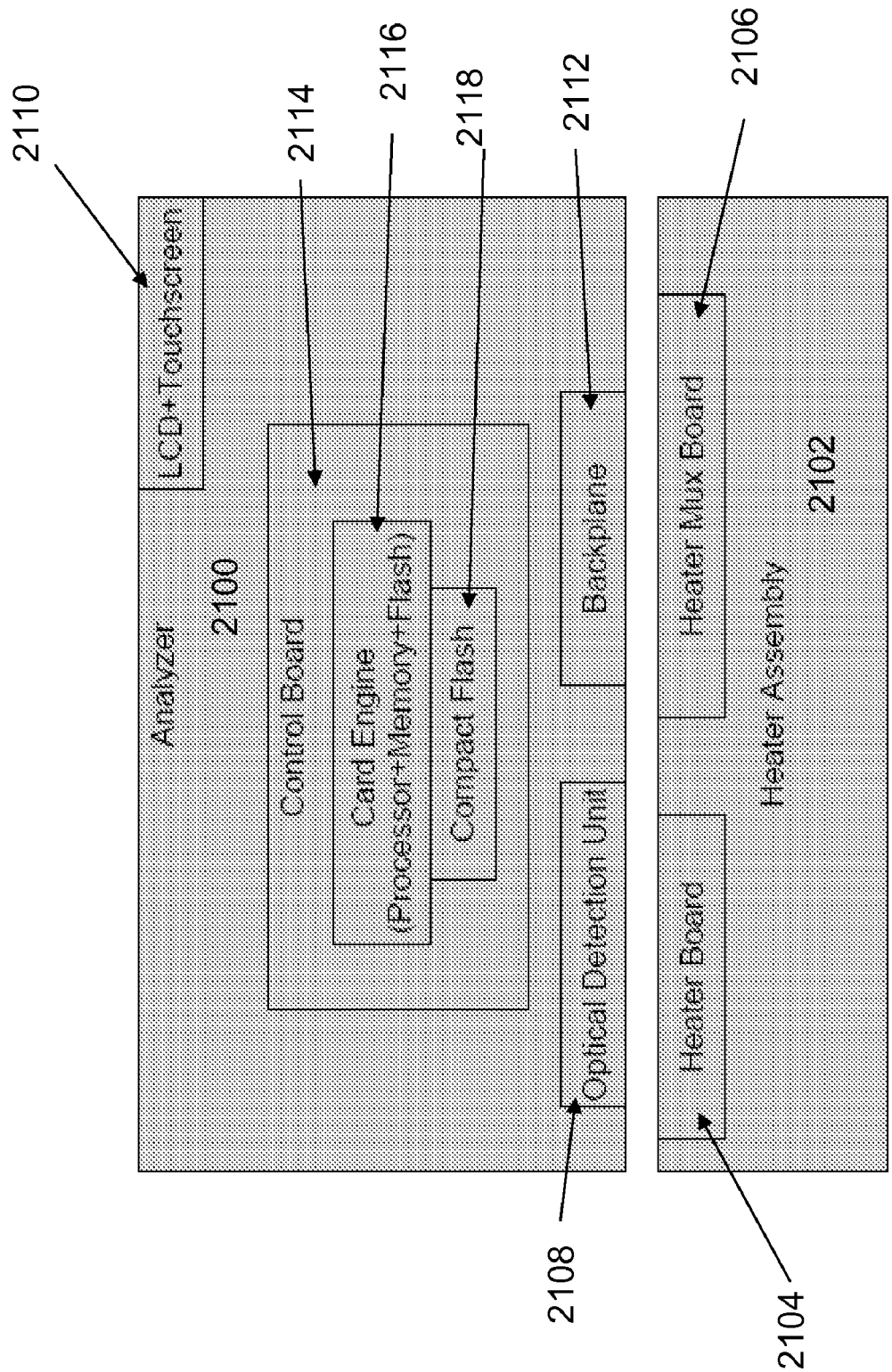
FIG. 19 shows an exemplary layout for electronics and software components, as further described herein.

An example of thermal cycling performance obtained with a configuration as described herein, is shown in FIG. 18 for a protocol that is set to heat up to 92° C., and stay there for 1 second, then cool to 62° C., and stay for 10 seconds. Cycle time is about 29 seconds, with 8 seconds required to heat from 62° C. and stabilize at 92° C., and 10 seconds required to cool from 92° C., and stabilize at 62° C.

Heater Multiplexing Under Software Control

Another aspect of the heater unit described herein, relates to a control of heat within the system and its components. The method leads to a greater energy efficiency of the apparatus described herein, because not all heaters are heating at the same time, and a given heater is receiving current for only part of the time.

Generally, the heating of microfluidic components, such as a PCR reaction chamber, is controlled by passing currents through suitably configured microfabricated heaters. The heating can be further controlled by periodically turning the current on and off with varying pulse width modulation (PWM), wherein pulse width modulation refers to the on-time/off-time ratio for the current. The current can be supplied by connecting a microfabricated heater to a high voltage source (for example, 30 V), which can be gated by the PWM signal. In some embodiments, the device includes 48 PWM signal generators. Operation of a PWM generator includes generating a signal with a chosen, programmable, period (the end count) and a particular granularity. For instance, the signal can be 4000 μs (micro-seconds) with a granularity of 1 μs, in which case the PWM generator can maintain a counter beginning at zero and advancing in increments of 1 μs until it reaches 4000 μs, when it returns to zero. Thus, the amount of heat produced can be adjusted by adjusting the end count. A high end count corresponds to a greater length of time during which the microfabricated heater receives current and therefore a greater amount of heat produced. It would be understood that the granularity and signal width can take values other than those provided here without departing from the principles described herein.

Exemplary Electronics and Software

The heater unit described herein can be controlled by various electronics circuitry, itself operating on receipt of computer-controlled instructions. FIG. 18 illustrates exemplary electronics architecture modules for operating a heater unit and diagnostic apparatus. It would be understood by one of ordinary skill in the art that other configurations of electronics components are consistent with operation of the apparatus as described herein. In the exemplary embodiment, the electronics architecture is distributed across two components of the apparatus: the Analyzer 2100 and a Heater unit 2102. The Analyzer apparatus as further described herein contains, for example, an Optical Detection Unit 2108, a Control Board 2114, a Backplane 2112, and a LCD Touchscreen 2110. The Control Board includes a Card Engine 2116 further described herein, and Compact Flash memory 2118, as well as other components. The Heater Assembly includes a Heater Board 2104 and a Heater Mux Board 2106, both further described herein.

In one embodiment, the Card Engine electronics module 2116 is a commercial, off the shelf "single board computer" containing a processor, memory, and flash memory for operating system storage.

The optional LCD+Touchscreen electronics module 2110 is a user interface, for example, driven through a touchscreen, such as a 640 pixel by 480 pixel 8 inch LCD and 5-wire touchscreen.

The Compact Flash electronics module 2118 is, for example, a 256 megabyte commercial, off the shelf, compact flash module for application and data storage. Other media are alternatively usable, such as USB-drive, smart media card, memory stick, and smart data-card having the same or other storage capacities.

The Backplane electronics module 2112 is a point of connection for the removable heater assembly 2102. Bare PC boards with two connectors are sufficient to provide the necessary level of connectivity.

The Control Board electronics module 2114 supports peripherals to the Card Engine electronics module 2116. In one embodiment, the peripherals include such devices as a USB host+slave or hub, a USB CDROM interface, serial ports, and ethernet ports. The Control Board 2114 can include a power monitor with a dedicated processor. The Control Board may also include a real time clock. The Control Board may further include a speaker. The Control Board 2114 also includes a CPLD to provide SPI access to all other modules and programming access to all other modules. The Control Board includes a programmable high voltage power supply. The Control Board includes a Serial-Deserializer interface to the LCD+Touchscreen electronics module 2110 and to the Optical Detection Unit electronics module 2108. The Control Board also includes module connectors.

In the exemplary embodiment, the optical detection unit electronics module 2108 contains a dedicated processor. The optical detection unit 2108 contains a serializer-deserializer interface. The optical detection unit 2108 contains LED drivers. The optical detection unit also contains high gain-low noise photodiode amplifiers. The optical detection unit can have power monitoring capability. The optical detection unit can also be remotely reprogrammable.

The Heater Board electronics module 2104 is preferably a glass heater board. The Heater Board has PCB with bonding pads for glass heater board and high density connectors.

In one embodiment, the heater mux ('multiplex') board electronics module 2106 has 24 high-speed ADC, 24 precision current sources, and 96 optically isolated current drivers for heating. The heater mux board has the ability to time-multiplex heating/measurement. The heater mux board has multiplexer banks to multiplex inputs to ADC, and to multiplex current source outputs. The heater mux board has a FPGA with a soft processor core and SDRAM. The heater mux board has a Power Monitor with a dedicated processor. The Heater Mux Board can be remotely reprogrammable.

In another embodiment, control electronics can be spread over four different circuit board assemblies. These include the MAIN board: Can serve as the hub of the Analyzer control electronics and manages communication and control of the other various electronic sub-assemblies. The main board can also serve as the electrical and communications interface with the external world. An external power supply (12V DC/10A; UL certified) can be used to power the system. The unit can communicate via 5 USB ports, a serial port and an Ethernet port. Finally, the main board can incorporate several diagnostic/safety features to ensure safe and robust operation of the Analyzer.

MUX Board: Upon instruction from the main board, the MUX board can perform all the functions typically used for accurate temperature control of the heaters and can coordinate the collection of fluorescence data from the detector board.

LCD Board: Can contain the typical control elements to light up the LCD panel and interpret the signals from the touch sensitive screen. The LCD/touch screen combination can serve as a mode of interaction with the user via a Graphical User Interface.

Detector Board: Can house typical control and processing circuitry that can be employed to collect, digitize, filter, and transmit the data from the fluorescence detection modules.

Certain software can be executed in each electronics module. The Control Board Electronics Module executes, for example, Control Board Power Monitor software. The Card Engine electronics module executes an operating system, graphical user interface (GUI) software, an analyzer module, and an application program interface (api). The Optical Detection Unit electronics module executes an optics software module. The Heater Mux Board electronics module executes dedicated Heater Mux software, and Heater Mux Power Monitor software. Each of the separate instances of software can be modular and under a unified control of, for example, driver software.

The exemplary electronics can use Linux, UNIX, Windows, or MacOS, including any version thereof, as the operating system. The operating system is preferably loaded with drivers for USB, Ethernet, LCD, touchscreen, and removable media devices such as compact flash. Miscellaneous programs for configuring the Ethernet interface, managing USB connections, and updating via CD-ROM can also be included.

In the embodiment of FIG. 17, the analyzer module is the driver for specific hardware. The analyzer module provides access to the Heater Mux Module, the Optical Detection Unit, the Control Board Power Monitor, the Real Time Clock, the High Voltage Power Supply, and the LCD backlight. The analyzer module provides firmware programming access to the Control Board power monitor, the Optical Detection Unit, and the Heater Mux Module.

The API provides uniform access to the analyzer module driver. The API is responsible for error trapping, and interrupt handling. The API is typically programmed to be thread safe.

The GUI software can be based on a commercial, off-the-shelf PEG graphics library. The GUI can use the API to coordinate the self-test of optical detection unit and heater assembly. The GUI starts, stops, and monitors test progress. The GUI can also implement an algorithm to arrive on diagnosis from fluorescence data. The GUI provides access control to unit and in some embodiments has an HIS/LIS interface.

The Control Board Power Monitor software monitors power supplies, current and voltage, and signals error in case of a fault.

The Optics Software performs fluorescence detection which is precisely timed to turn on/off of LED with synchronous digitization of the photodetector outputs. The Optics Software can also monitor power supply voltages. The Optics Software can also have self test ability.

The Heater Mux Module software implements a "protocol player" which executes series of defined "steps" where each "step" can turn on sets of heaters to implement a desired microfluidic action. The Heater Mux Module software also has self test ability. The Heater Mux Module software contains a fuzzy logic temperature control algorithm.

The Heater Mux Power Monitor software monitors voltage and current levels. The Heater Mux Power Monitor software can participate in self-test, synchronous, monitoring of the current levels while turning on different heaters.

Overview of Apparatus for Receiving a Microfluidic Cartridge

The present technology relates to a heater unit, cartridge, complementary apparatus, and related methods for amplifying, and carrying out diagnostic analyses on, nucleotides from biological samples. The technology includes a heater unit for heating selective regions of a microfluidic substrate, such as contained in a disposable or reusable microfluidic cartridge containing multiple sample lanes capable of processing samples in parallel as further described herein, and a reusable apparatus that is configured to selectively actuate on-cartridge operations, to detect and analyze the products of the PCR amplification in each of the lanes separately, in all simultaneously, or in groups simultaneously, and, optionally, can display the progression of analyses and results thereof on a graphical user interface. Such a reusable apparatus is further described in U.S. patent application Ser. No. 11/985,577, entitled "Microfluidic System For Amplifying And Detecting Polynucleotides In Parallel" and filed on Nov. 14, 2007, and which is incorporated herein by reference in its entirety.

An Analyzer unit can contain typical hardware/firmware that can be employed to drive and monitor the operations on the cartridges as well as software to interpret, communicate and store the results. Typical components of the Analyzer can include: (a) Control Electronics (DAQ), (b) Heater/Sensor Unit, (c) Fluorescent Detection Module, (d) Mechanical Fixtures, (e) Software and (f) User Interface (LCD/Touch screen) (g) Peripherals (CD-ROM, USB/Serial/Ethernet communication ports, barcode scanner, optional keyboard).

Figure 20:
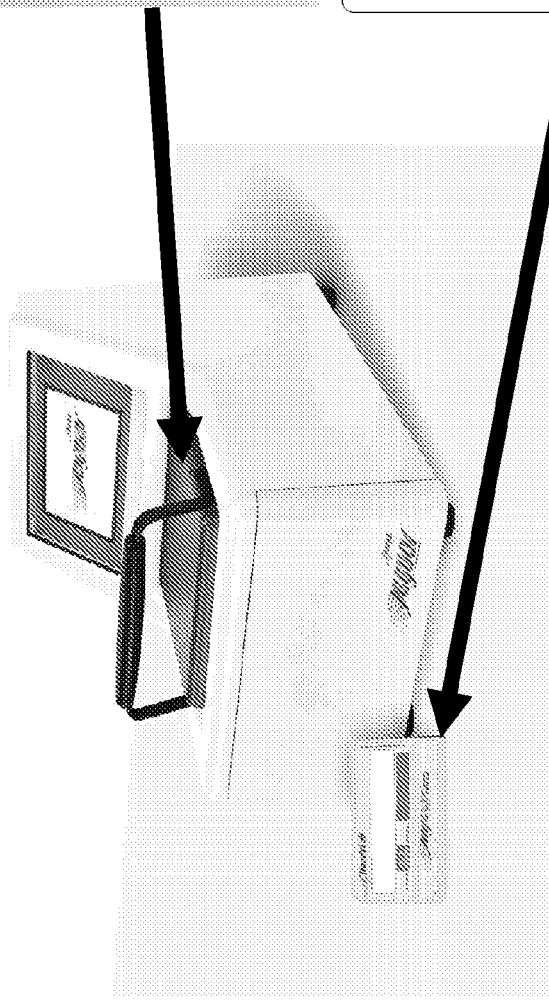
FIG. 20 shows an exemplary apparatus, a microfluidic cartridge, and a read head, as further described herein.
Figure 20:
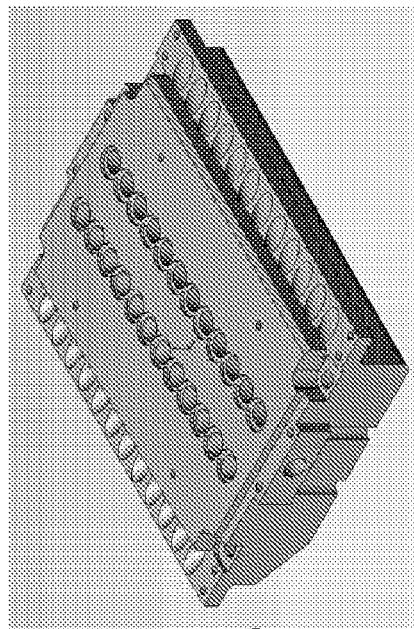
Figure 20:
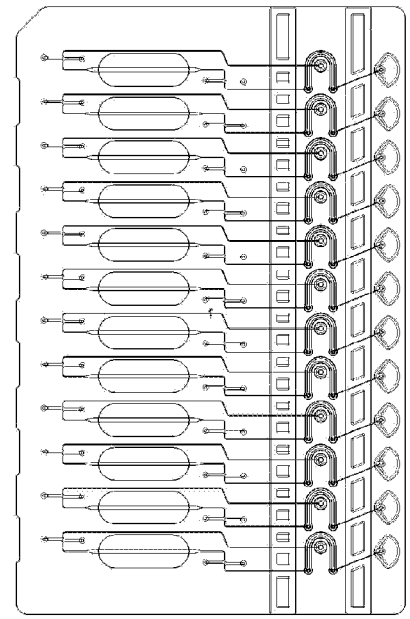

FIG. 20 shows a perspective view of an exemplary apparatus 100 consistent with those described herein, as well as various components thereof, such as exemplary cartridge 200 that contains multiple sample lanes, and exemplary read head 300 that contains detection apparatus for reading signals from cartridge 200. The apparatus 100 of FIG. 20 is able to carry out real-time PCR on a number of samples in cartridge 200 simultaneously. Preferably the number of samples is 12 samples, as illustrated with exemplary cartridge 200, though other numbers of samples such as 4, 8, 10, 16, 20, 24, 25, 30, 32, 36, 40, and 48 are within the scope of the present description. In preferred operation of the apparatus, a PCR-ready solution containing the sample, and, optionally, one or more analyte-specific reagents (ASR's) is prepared, as further described elsewhere (see, e.g., U.S. patent application publication 2006-0166233, incorporated herein by reference), prior to introduction into cartridge 200.

In some embodiments, an apparatus includes: a receiving bay configured to selectively receive a microfluidic cartridge as described herein; at least one heat source thermally coupled to the receiving bay; and a processor coupled to the heat source, wherein the heat source is configured to selectively heat individual regions of individual sample lanes in the cartridge, and the processor is configured to control application of heat to the individual sample lanes, separately, in all simultaneously, or in groups simultaneously; at least one detector configured to detect one or more polynucleotides or a probe thereof in a sample in one or more of the individual sample lanes, separately or simultaneously; and a processor coupled to the detector to control the detector and to receive signals from the detector.

The receiving bay is a portion of the apparatus that is configured to selectively receive the microfluidic cartridge. For example, the receiving bay and the microfluidic cartridge can be complementary in shape so that the microfluidic cartridge is selectively received in, e.g., a single orientation. The microfluidic cartridge can have a registration member that fits into a complementary feature of the receiving bay. The registration member can be, for example, a cut-out on an edge of the cartridge, such as a corner that is cut-off, or one or more notches or grooves that are made on one or more of the sides in a distinctive pattern that prevents a cartridge from being loaded into the bay in more than one distinct orientation. By selectively receiving the cartridge, the receiving bay can help a user to place the cartridge so that the apparatus can properly operate on the cartridge. The cartridge can be designed to be slightly smaller than the dimensions of the receiving bay, e.g., by approximately 200-300 microns, for easy placement and removal of the cartridge.

The receiving bay can also be configured so that various components of the apparatus that operate on the microfluidic cartridge (heat sources, detectors, force members, and the like) are positioned to properly operate thereon. For example, a contact heat source can be positioned in the receiving bay such that it can be thermally coupled to one or more distinct locations on a microfluidic cartridge that is selectively received in the bay. Microheaters in the heater unit are aligned with corresponding heat-requiring microcomponents (such as valves, pumps, gates, reaction chambers, etc). The microheaters can be designed to be slightly bigger than the heat requiring microfluidic components so that even though the cartridge may be off-centered from the heater, the individual components can still function effectively.

As further described herein, the lower surface of the cartridge can have a layer of mechanically compliant heat transfer laminate that can enable thermal contact between the microfluidic substrate and the microheater substrate of the heater unit. A minimal pressure of 1 psi can be employed for reliable operation of the thermal valves, gates and pumps present in the microfluidic cartridge.

The apparatus can further include a sensor coupled to the processor, the sensor configured to sense whether the microfluidic cartridge is selectively received.

The processor can be programmable to operate the detector to detect one or more polynucleotides or a probe thereof in a microfluidic cartridge located in the receiving bay.

The detector can be, for example, an optical detector. For example, the detector can include a light source that selectively emits light in an absorption band of a fluorescent dye, and a light detector that selectively detects light in an emission band of the fluorescent dye, wherein the fluorescent dye corresponds to a fluorescent polynucleotide probe or a fragment thereof. Alternatively, for example, the optical detector can include a bandpass-filtered diode that selectively emits light in the absorption band of the fluorescent dye and a bandpass filtered photodiode that selectively detects light in the emission band of the fluorescent dye; or for example, the optical detector can be configured to independently detect a plurality of fluorescent dyes having different fluorescent emission spectra, wherein each fluorescent dye corresponds to a fluorescent polynucleotide probe or a fragment thereof; or for example, the optical detector can be configured to independently detect a plurality of fluorescent dyes at a plurality of different locations on a microfluidic cartridge, wherein each fluorescent dye corresponds to a fluorescent polynucleotide probe or a fragment thereof in a different sample. The detector can also be configured to detect the presence or absence of sample in a PCR reaction chamber in a given sample lane, and to condition initiation of thermocycling upon affirmative detection of presence of the sample. Further description of suitably configured detectors are described in U.S. patent application Ser. No. 11/940,321, filed on Nov. 14, 2007 and entitled "Fluorescence Detector for Microfluidic Diagnostic System", incorporated herein by reference.

Although the various depictions therein show a heater substrate disposed underneath a microfluidic substrate, and a detector disposed on top of it, it would be understood that an inverted arrangement would work equally as well. In such an embodiment, the heater would be forced down onto the microfluidic substrate, making contact therewith, and the detector would be mounted underneath the substrate, disposed to collect light directed downwards towards it.

In various embodiments, the apparatus can further include an analysis port. The analysis port can be configured to allow an external sample analyzer to analyze a sample in the microfluidic cartridge. For example, the analysis port can be a hole or window in the apparatus which can accept an optical detection probe that can analyze a sample or progress of PCR in situ in the microfluidic cartridge. In some embodiments, the analysis port can be configured to direct a sample from the microfluidic cartridge to an external sample analyzer; for example, the analysis port can include a conduit in fluid communication with the microfluidic cartridge that directs a liquid sample containing an amplified polynucleotide to a chromatography apparatus, an optical spectrometer, a mass spectrometer, or the like.

The heat source can be, for example, a heat source such as a resistive heater or network of resistive heaters. In some embodiments, the at least one heat source can be a contact heat source selected from a resistive heater (or network thereof), a radiator, a fluidic heat exchanger and a Peltier device. The contact heat source can be configured at the receiving bay to be thermally coupled to one or more distinct locations of a microfluidic cartridge received in the receiving bay, whereby the distinct locations are selectively heated.

In various embodiments, the heat source is disposed in a heating unit that is configured to be removable from the apparatus, as further described herein.

In various embodiments, the apparatus can include a compliant layer at the contact heat source configured to thermally couple the contact heat source with at least a portion of a microfluidic cartridge received in the receiving bay. The compliant layer can have a thickness of between about 0.05 and about 2 millimeters and a Shore hardness of between about 25 and about 100.

In various embodiments, the apparatus can further include one or more force members configured to apply force to at least a portion of a microfluidic cartridge received in the receiving bay. The one or more force members are configured to apply force to thermally couple the at least one heat source to at least a portion of the microfluidic cartridge. The application of force is important to ensure consistent thermal contact between the heater wafer and the PCR reactor and microvalves in the microfluidic cartridge.

The apparatus preferably also includes a processor microprocessor circuitry, in communication with, for example, the input device and a display, that accepts a user's instructions and controls analysis of samples.

In various embodiments, the apparatus can further include at least one input device coupled to the processor, the input device being selected from the group consisting of a keyboard, a touch-sensitive surface, a microphone, and a mouse.

In various embodiments, the apparatus can further include at least one sample identifier coupled to the processor, the sample identifier being selected from an optical scanner such as an optical character reader, a bar code reader, or a radio frequency tag reader. For example, the sample identifier can be a handheld bar code reader.

In various embodiments, the apparatus can further include at least one data storage medium coupled to the processor, the medium selected from: a hard disk drive, an optical disk drive, or one or more removable storage media such as a CD-R, CD-RW, USB-drive, or flash memory card.

In various embodiments, the apparatus can further include at least one output coupled to the processor, the output being selected from a display, a printer, and a speaker, the coupling being either directly through a directly dedicated printer cable, or wirelessly, or via a network connection.

The apparatus further optionally comprises a display that communicates information to a user of the system. Such information includes but is not limited to: the current status of the system; progress of PCR thermocycling; and a warning message in case of malfunction of either system or cartridge. The display is preferably used in conjunction with an external input device as elsewhere described herein, through which a user may communicate instructions to apparatus 100. A suitable input device may further comprise a reader of formatted electronic media, such as, but not limited to, a flash memory card, memory stick, USB-stick, CD, or floppy diskette. An input device may further comprise a security feature such as a fingerprint reader, retinal scanner, magnetic strip reader, or bar-code reader, for ensuring that a user of the system is in fact authorized to do so, according to pre-loaded identifying characteristics of authorized users. An input device may additionally—and simultaneously—function as an output device for writing data in connection with sample analysis. For example, if an input device is a reader of formatted electronic media, it may also be a writer of such media. Data that may be written to such media by such a device includes, but is not limited to, environmental information, such as temperature or humidity, pertaining to an analysis, as well as a diagnostic result, and identifying data for the sample in question.

The apparatus may further include a computer network connection that permits extraction of data to a remote location, such as a personal computer, personal digital assistant, or network storage device such as computer server or disk farm. The network connection can be a communications interface selected from the group consisting of: a serial connection, a parallel connection, a wireless network connection, and a wired network connection such as an ethernet or cable connection, wherein the communications interface is in communication with at least the processor. The computer network connection may utilize, e.g., ethernet, firewire, or USB connectivity. The apparatus may further be configured to permit a user to e-mail results of an analysis directly to some other party, such as a healthcare provider, or a diagnostic facility, or a patient.

In various embodiments, there is an associated computer program product that includes computer readable instructions thereon for operating the apparatus and for accepting instructions from a user.

Apparatus 100 may optionally comprise one or more stabilizing feet that cause the body of the device to be elevated above a surface on which system 100 is disposed, thereby permitting ventilation underneath system 100, and also providing a user with an improved ability to lift system 100.

In some embodiments, the heat sources are operated by an operating system, which operates the device during use. The operating system includes a processor (e.g., a computer) configured to actuate the heat sources according to a desired protocol. Processors configured to operate microfluidic devices are described in, e.g., U.S. application Ser. No. 09/819,105, filed Mar. 28, 2001, which application is incorporated herein by reference.

In various embodiments, a processor executes instructions from a computer program product that includes computer readable instructions thereon for operating the apparatus.

In various embodiments, the computer program product can include one or more instructions to cause the system to: output an indicator of the placement of the microfluidic cartridge in the receiving bay; read a sample label or a microfluidic cartridge label; output directions for a user to input a sample identifier; output directions for a user to load a sample transfer member with the PCR-ready sample; output directions for a user to introduce the PCR-ready sample into the microfluidic cartridge; output directions for a user to place the microfluidic cartridge in the receiving bay; output directions for a user to close the lid to operate the force member; output directions for a user to pressurize the PCR-ready sample in the microfluidic cartridge by injecting the PCR-ready sample with a volume of air between about 0.5 mL and about 5 mL; and output status information for sample progress from one or more lanes of the cartridge.

In various embodiments, the computer program product can include one or more instructions to cause the system to: heat the PCR ready-sample under thermal cycling conditions suitable for creating PCR amplicons from the neutralized polynucleotide; contact the neutralized polynucleotide sample or a PCR amplicon thereof with at least one probe that is selective for a polynucleotide sequence; independently contact each of the neutralized polynucleotide sample and a negative control polynucleotide with the PCR reagent mixture under thermal cycling conditions suitable for independently creating PCR amplicons of the neutralized polynucleotide sample and PCR amplicons of the negative control polynucleotide; contact the neutralized polynucleotide sample or a PCR amplicon thereof and the negative control polynucleotide or a PCR amplicon thereof with at least one probe that is selective for a polynucleotide sequence; output a determination of the presence of a polynucleotide sequence in the biological sample, the polynucleotide sequence corresponding to the probe, if the probe is detected in the neutralized polynucleotide sample or a PCR amplicon thereof; and/or output a determination of a contaminated result if the probe is detected in the negative control polynucleotide or a PCR amplicon thereof.

In various embodiments, the computer program product can include one or more instructions to cause the system to automatically conduct one or more of the steps of the method.

EXAMPLES

Example 1

Analyzer Apparatus

This non-limiting example describes pictorially, various embodiments of an apparatus, showing incorporation of a heater unit and a microfluidic cartridge operated on by the heater unit.

Figure 22:
FIGS. 21-23 show positioning of a cartridge in an exemplary apparatus.
Figure 21:
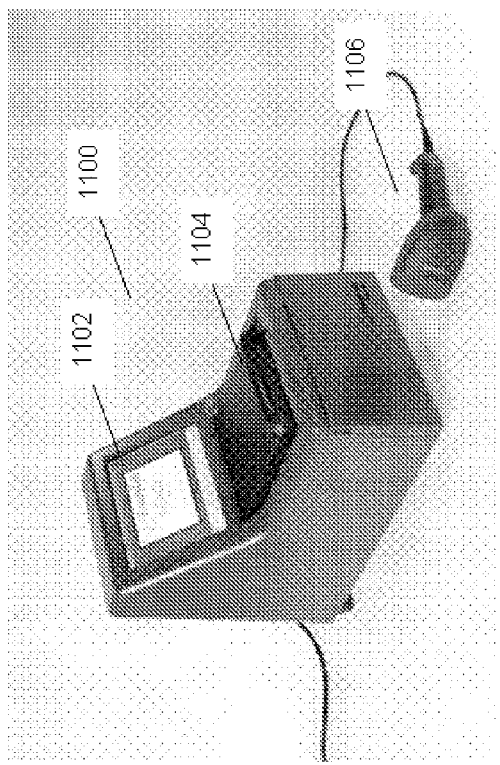
Figure 23:
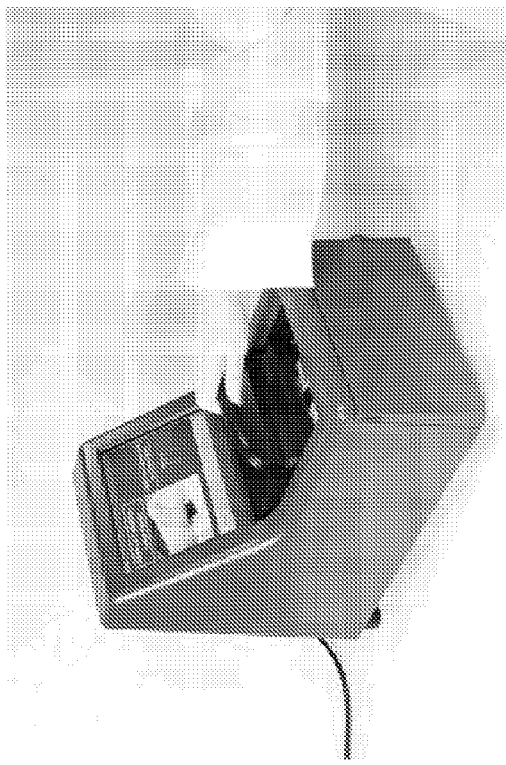

FIG. 21 shows an apparatus 1100 that includes a housing having a display output 1102, an openable lid 1104, and a bar code reader 1106. The cartridge is positioned in a single orientation in a receiving bay under the lid, FIG. 22. The lid of the apparatus can be closed to apply pressure to the cartridge, as shown in FIG. 23. The unit currently weighs about 20 lbs. and is approximately 10" wide by 16" deep by 13" high.

Figure 25:
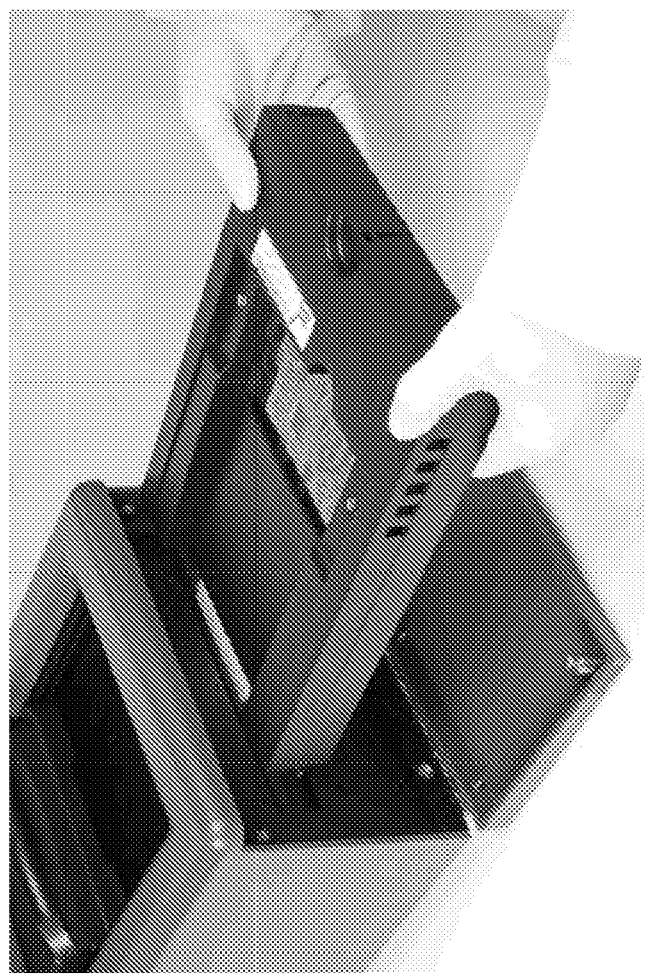
FIGS. 24 and 25 show removal of a heater unit from an exemplary apparatus.
Figure 24:
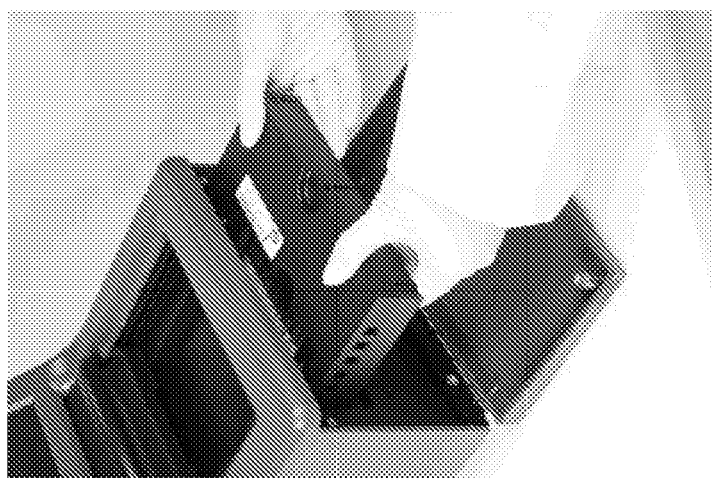

FIGS. 24 and 25: The heating stage of the apparatus can be removable for cleaning, maintenance, or to replace a custom heating stage for a particular microfluidic cartridge. FIGS. 24 and 25 also show how a heater unit is insertable and removable from a front access door to an analyzer apparatus.

Example 2

Assembly of an Exemplary Heater Unit

FIG. 26A shows an exploded view of an exemplary heater unit. The unit has a top cover and a bottom cover that together enclose a Mux board (control board), a pressure support layer, and insulator film, and a microthermal circuit on a PCB. The last of these is the heat source that selectively heats regions of a microfluidic substrate placed in contact therewith through the top cover.

An exemplary heater substrate, FIG. 26B, consists of a photo-lithographically processed glass wafer bonded to a standard 0.100" standard FR4 printed circuit board. The glass wafer is 0.5 mm thick and is cut into a rectangle the size of 3.5×4.25 inches. The glass substrate has numerous metal heaters and resistive temperature sensors photo-lithographically etched on the surface of the glass wafer. The substrate is aligned and bonded to the PCBoard using a compliant epoxy, ensuring flatness to within 2-3 mils over the surface of the wafer. The cured epoxy should withstand up to 120° C. for two hours minimum. Approximately 300-400 bond pads of the size of approximately 1 mm×0.25 mm, with exposed gold surfaces, are located along the two long edges of the wafer. These pads are wirebonded (ball-bonding) to corresponding pads on the PCB using 1.5 mil gold wires. Wire bonding is a threading process, standard in semiconductor FAB. Alternatively, a flip-chip method may be used, though such methods are more complicated and may warp the wafer because of thermal mismatch. Wire bonds should have good integrity and pass defined pull strength. The substrate is baked at 120° C. for two hours and then the wire bonds are encapsulated by a compliant epoxy that will protect the wirebonds but not damage the bonds even at 120° C. Encapsulant should not spill over pre-defined area around the wirebonds and should not be taller than a defined height. For example, instead of laying epoxy all over the substrate, lines (e.g., a hash pattern) of it are made so that epoxy cures and air escapes through side. Alternatively, a laminate fill (adhesive on both sides) can be used. Standard connectors are soldered to the PCB and then the unit is tested using a test set-up to ensure all heaters and sensors read the right resistance values.

Figure 27:
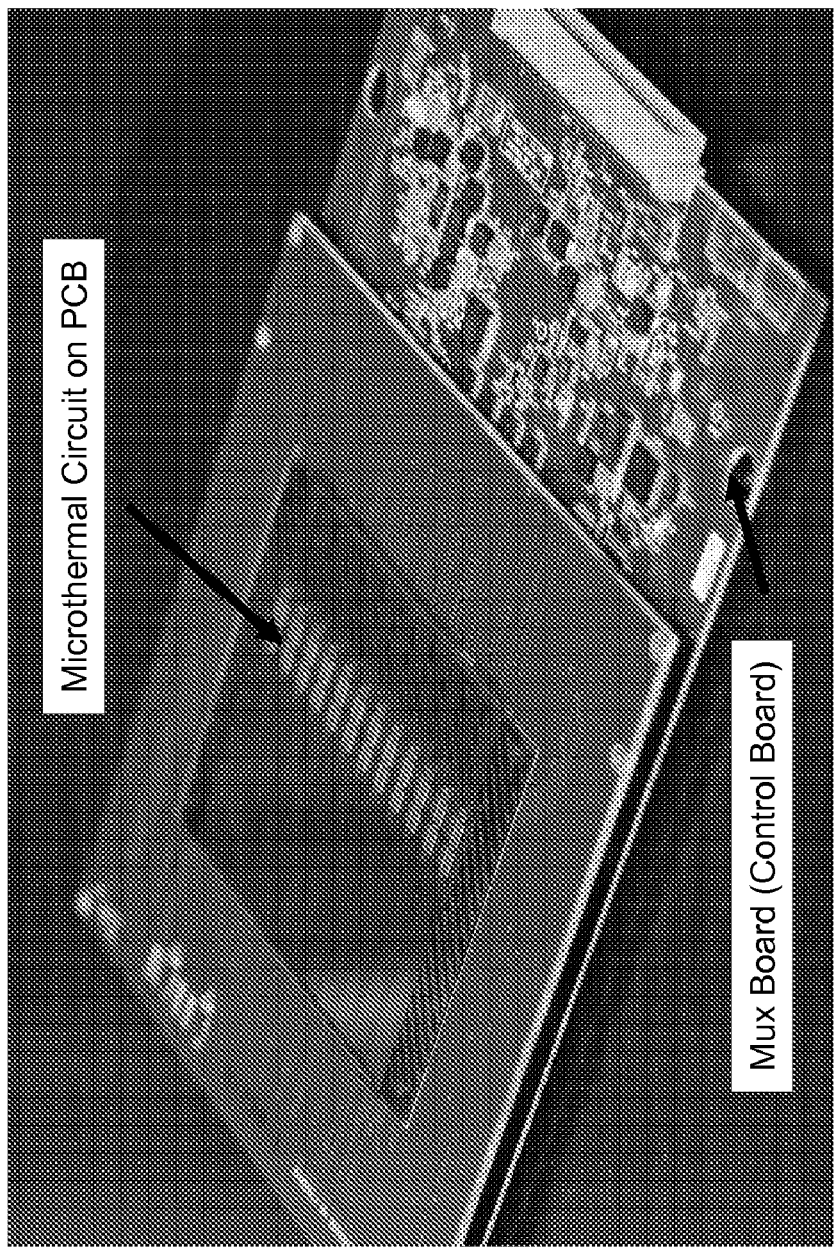
FIGS. 27-29 show an exemplary heater substrate and heater unit.
Figure 28:
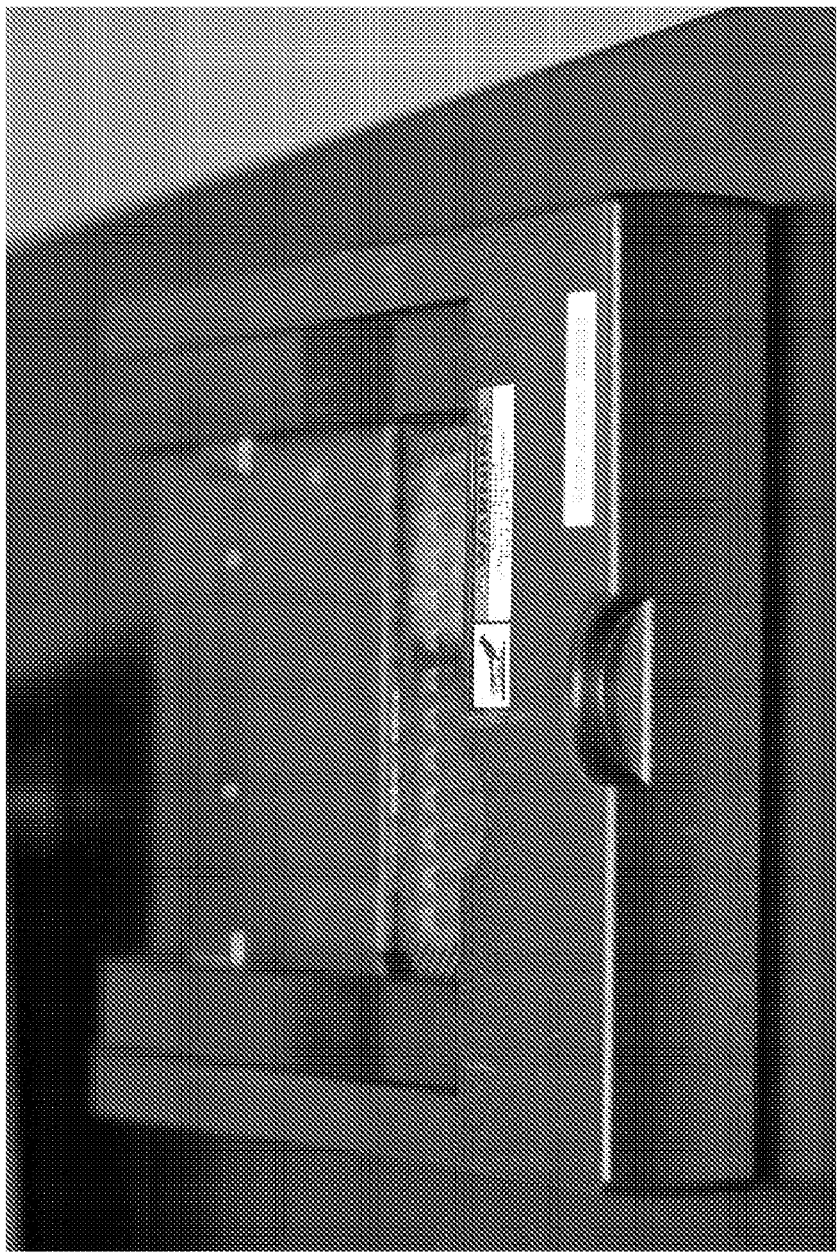
Figure 29:
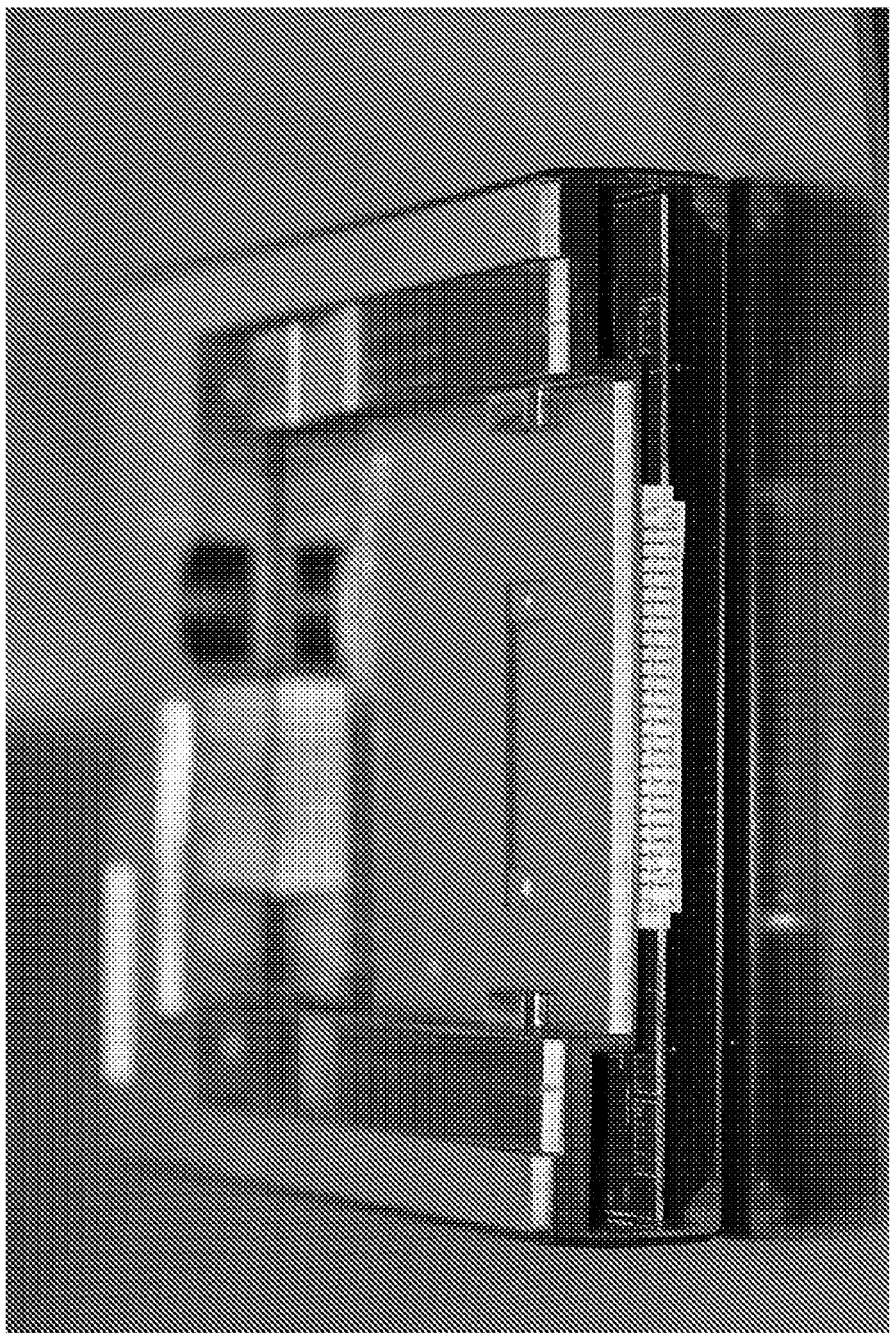

Pictures of an exemplary Mux board and assembled heater unit are shown in FIGS. 27-29.

Example 3

Pulse Width Modulation

In various embodiments, the operation of a PWM generator can also include a programmable start count in addition to the aforementioned end count and granularity. In such embodiments, multiple PWM generators can produce signals that can be selectively non-overlapping (e.g., by multiplexing the on-time of the various heaters) such that the current capacity of the high voltage power is not exceeded. Multiple heaters can be controlled by different PWM signal generators with varying start and end counts. The heaters can be divided into banks, whereby a bank defines a group of heaters of the same start count. For example, 36 PWM generators can be grouped into six different banks, each corresponding to a certain portion of the PWM cycle (500 ms for example). The end count for each PWM generator can be selectively programmed such that not more than six heaters, for example, will be on at any given time. Other numbers are consistent with operation herein. A portion of a PWM cycle can be selected as dead time (count 3000 to 4000 for example) during which no heating takes place and sensitive temperature sensing circuits can use this time to sense the temperature. The table below represents a PWM cycle for the foregoing example:

|                  | Start Count | End Count | Max End count |
|------------------|-------------|-----------|---------------|
| Bank 1           |             |           |               |
| PWM generator #1 | 0           | 150       | 500           |
| PWM generator #2 | 0           | 220       | 500           |
| ...              | ...         | ...       | ...           |
| PWM generator #6 | 0           | 376       | 500           |
| Bank 2           |             |           |               |
| PWM generator #7 | 500         | 704       | 1000          |
| PWM generator #8 | 500         | 676       | 1000          |
| ...              | ...         | ...       | ...           |
| PWM generator #12| 500         | 780       | 1000          |
| Bank 3           |             |           |               |
| PWM generator #13| 1000        | 1240      | 1500          |
| PWM generator #14| 1000        | 1101      | 1500          |
| ...              | ...         | ...       | ...           |
| PWM generator #18| 1000        | 1409      | 1500          |
| Bank 4           |             |           |               |
| PWM generator #19| 1500        | 1679      | 2000          |
| PWM generator #20| 1500        | 1989      | 2000          |
| ...              | ...         | ...       | ...           |
| PWM generator #24| 1500        | 1502      | 2000          |
| Bank 5           |             |           |               |
| PWM generator #25| 2000        | 2090      | 2500          |
| PWM generator #26| 2000        | 2499      | 2500          |
| ...              | ...         | ...       | ...           |
| PWM generator #30| 2000        | 2301      | 2500          |

-continued

|  | Start Count | End Count | Max End count |
|---|---|---|---|
| Bank 6 | | | |
| PWM generator #31 | 2500 | 2569 | 3000 |
| PWM generator #32 | 2500 | 2790 | 3000 |
| ... | ... | ... | ... |
| PWM generator #36 | 2500 | 2678 | 3000 |

Example 4

Heater Unit

An exemplary design for a heater unit is found in U.S. design patent application Ser. No. 29/257,029 filed Mar. 27, 2006, the description of which is incorporated herein by reference in its entirety.

Example 5

Heater Circuitry Design

Figure 30A:
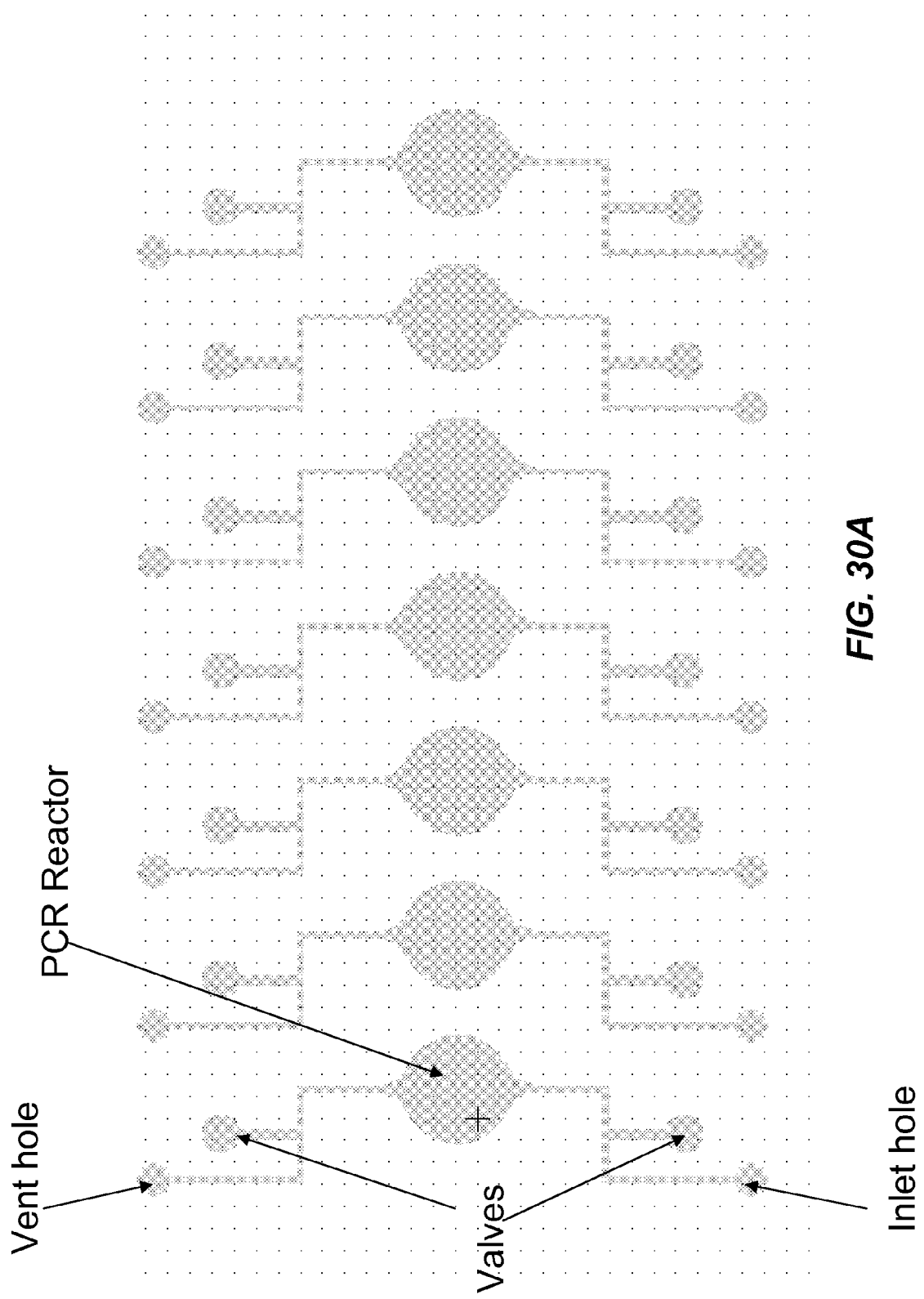
FIGS. 30A-30C show an exemplary heater configuration to heat a PCR chamber.
Figure 30B:
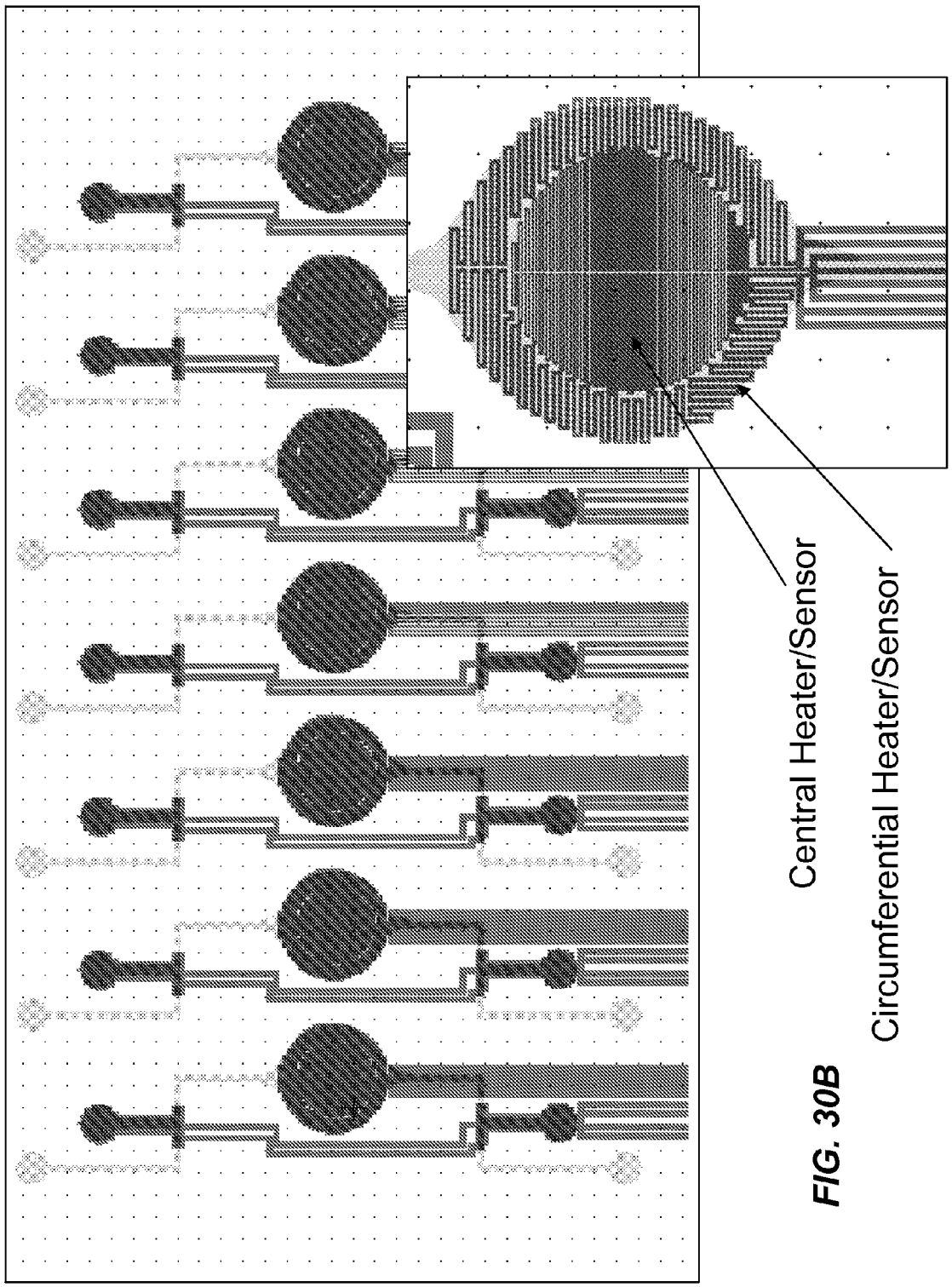
Figure 30C:
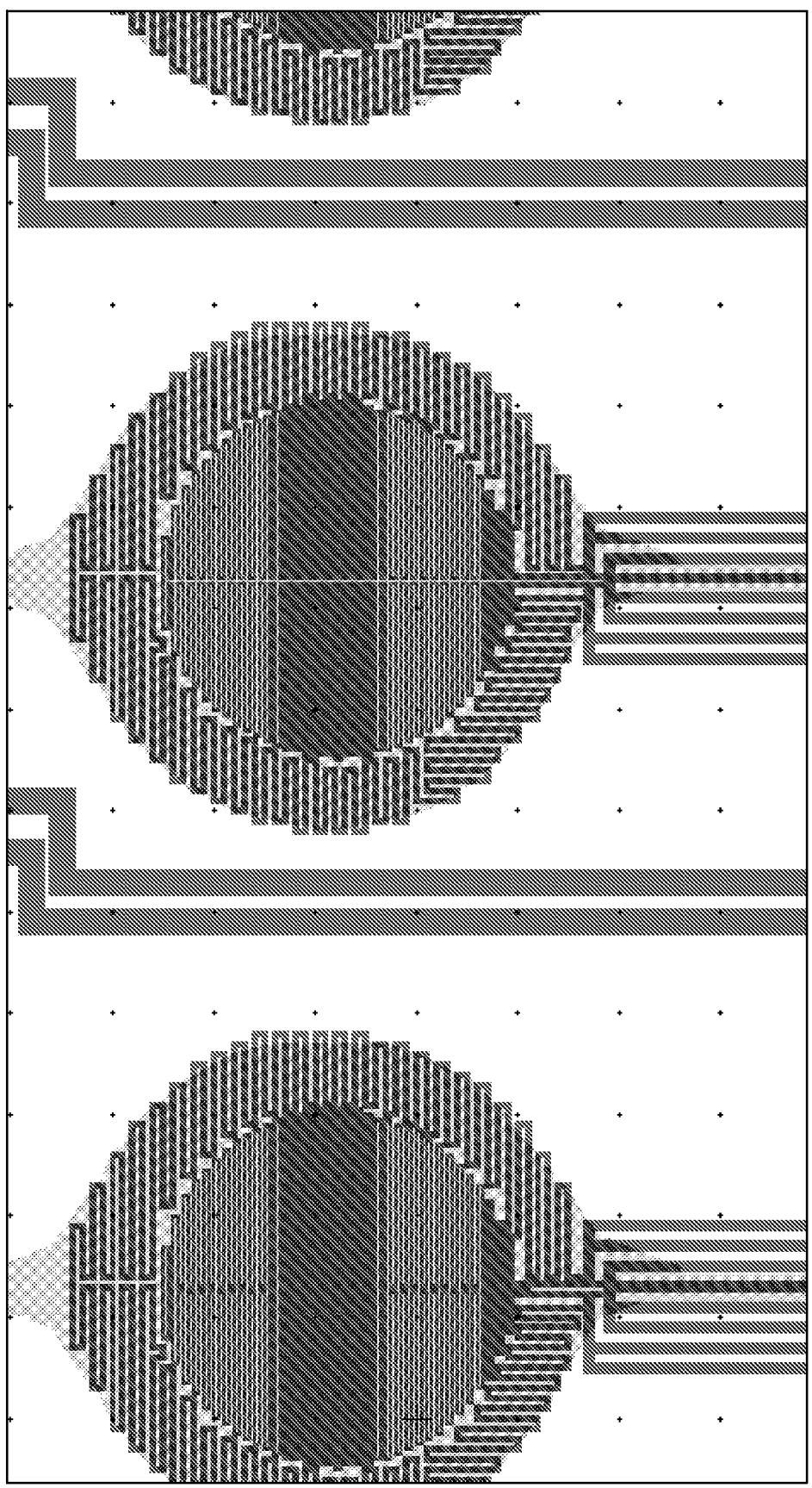

FIGS. 30A-30C show an alternative heater circuit for heating a PCR chamber. FIG. 30A shows 7 lanes in a microfluidic substrate that have a PCR chamber that is bulbous in shape. An inlet, valves, and a vent hole are disposed on either side of the chamber.

FIG. 30B shows layout of heater circuitry that can activate the valves as well as heat the PCR chamber. The inset shows a representative heater element for a PCR chamber. It is rounded in shape and has both a central and a circumferential heater/sensor element.

FIG. 30C shows fine structure of the heating elements of both the central and the circumferential heater/sensors. The overall arrangement promotes rapid and uniform heating of the PCR reaction chamber. The narrower wires in the central heater/sensor ensures that the center of the chamber receives most heat.

Example 6

Heater circuit Fine Structure

Figure 31A:
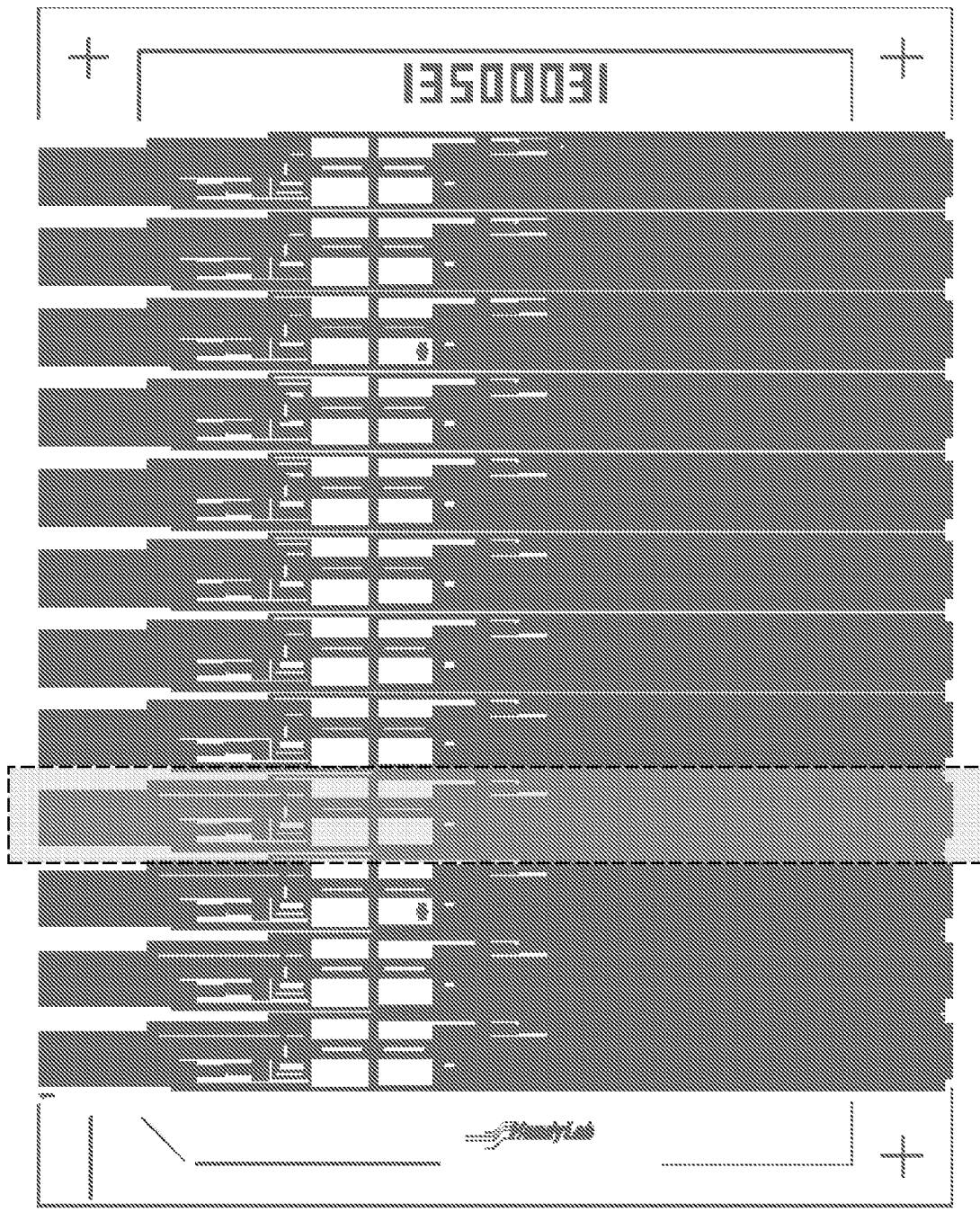
FIGS. 31A-31F show aspects of heater element fine structure.
Figure 31B:
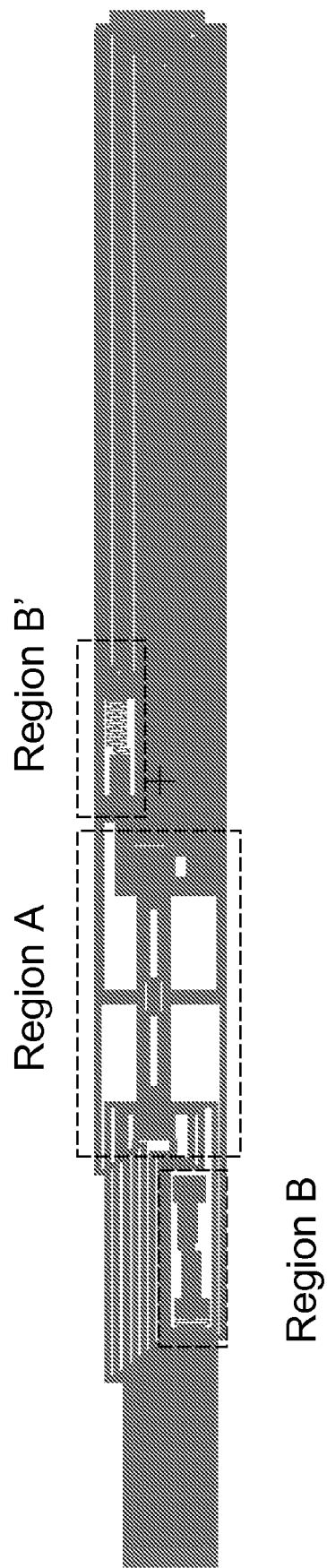

FIGS. 31A and 31B show, respectively, a set of heater arrays on a substrate, and a blown-up view of one representative array. In FIG. 31B, various regions of the heater array are identified as A, B, and B'.

Figure 31C:
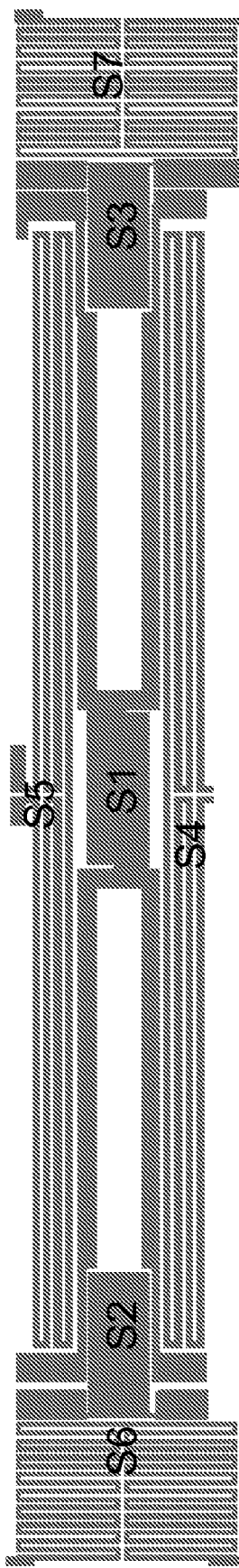
Figure 31D:
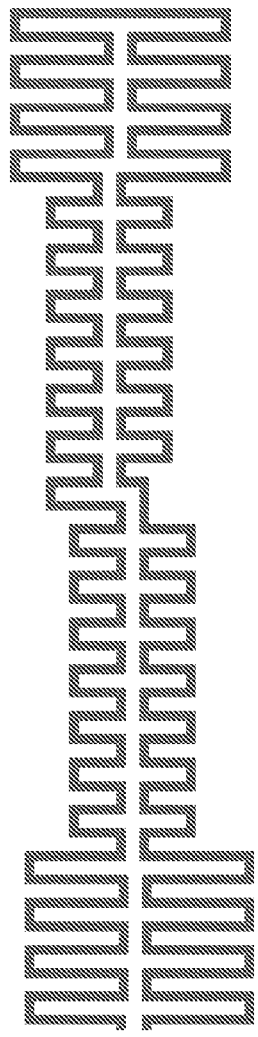
Figure 31E:
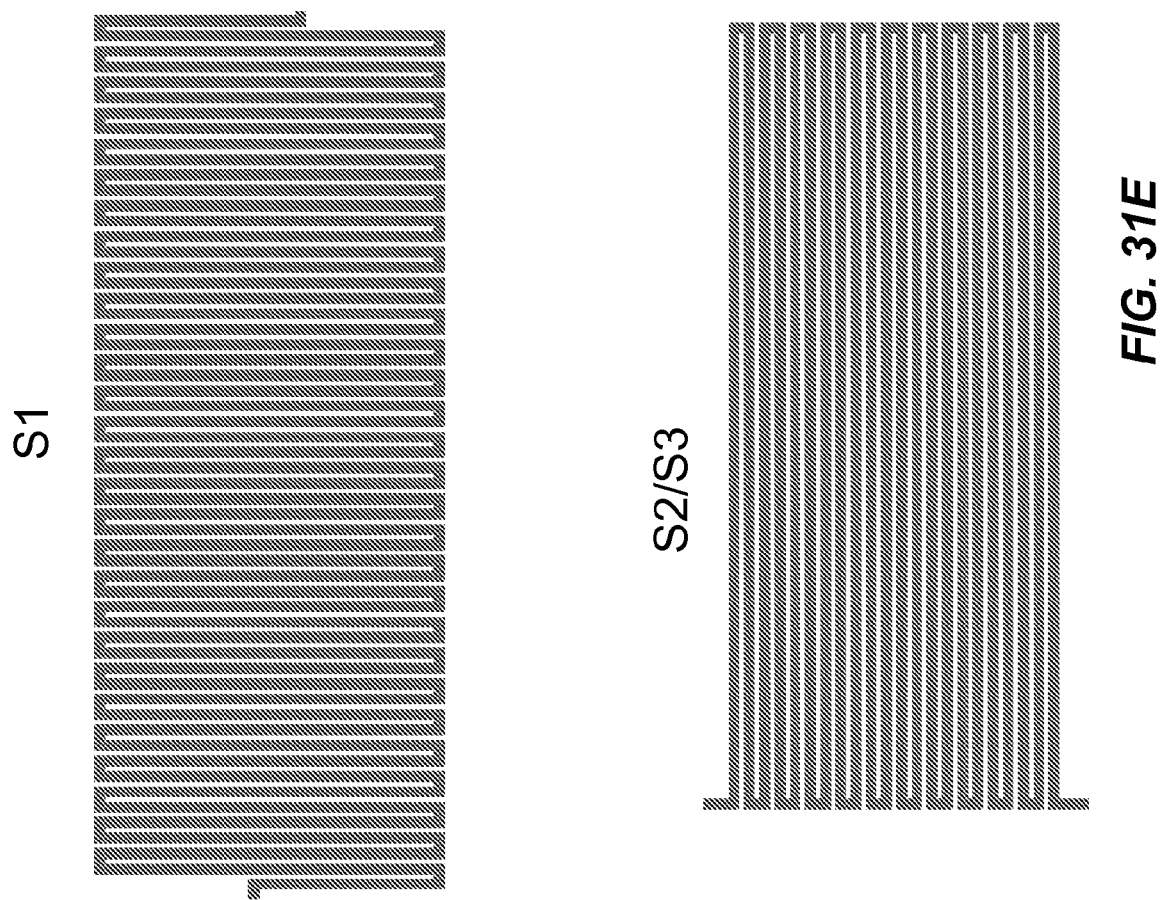
Figure 31F:
Figure 31F:
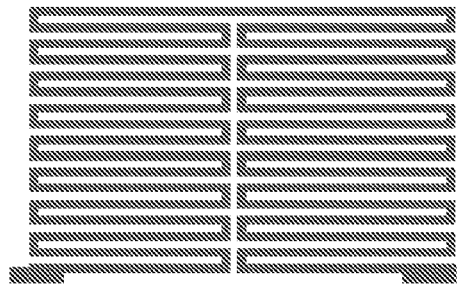

FIGS. 31C and 31D show, respectively, detailed views of regions A and B. Region A is identified with sub-regions, S1-S7. FIGS. 31E and 31F show detailed views of sub-regions S1-S7. Attributes of the various sub-regions are as follows.

S1, S2 and S3 are temperature sensors (S2 and S3 have similar design to one another); S4 & S5 are heaters, carry high currents during operation and have similar design to one another; S6 & S7 are heaters, carry high currents during operation and have similar design to one another. Since all the sensors and heaters are operated at the same time, there should be no shorting between metals of these sensors/heaters.

For S1, S2, and S3, the nominal width of metal in the heater elements is ~20 µm, and the nominal gap between adjacent portions of metal is ~10 µm. It has been found that sensor lines should optimally sense in at least 95% of the defined sensing area. The resistance of the sensors has to be within a defined range: lower values cause loss of sensitivity, resistors higher than certain values are not able to be read by some control circuitry. Pits no larger than half the width of the sensor line should be present on the oxide surface (10 µm). As the surface of the heater is mechanically pressed against by for example, a plastic microfluidic cartridge repeatedly, pits cause the metal to wear out over time.

For S4, and S5, the nominal width of metal in the heater elements is ~60 µm, and the nominal gap between adjacent portions of metal is ~60 µm. For this region, the heaters should cover almost 100% of the heating area to provide pre-defined heating pattern. Since heaters carry high currents, pits will cause hot spots in the heater and will cause the heater to fail over repeated operation. Pits no larger than half the width of the heater line should be present on the oxide surface. As the surface of the heater is mechanically pressed against by for example, a plastic microfluidic cartridge repeatedly, pits cause the metal to wear out over time. The resistance of heater should be within a controlled range in order to carry desired current.

For S6, S7: the nominal width of metal in the heater elements is ~45 µm; the nominal gap is ~45 µm. The heater should cover almost 100% of the heating area to provide pre-defined heating pattern. Since heaters carry high currents, pits will cause hot spots in the heater and will cause the heater to fail over repeated operation. Pits no larger than half the width of the heater line (~25 µm) should be present on the oxide surface. As the surface of the heater is mechanically pressed against by for example, a plastic microfluidic cartridge repeatedly, pits cause the metal to wear out over time. The resistance of heater should be within a controlled range in order to carry desired current.

For region B, the nominal width of metal in the heater elements is ~75 µm, and the nominal gap is ~125 µm. These sensors are also used as a heater and carry high currents during operation. The heater should cover almost 100% of the heating area to provide pre-defined heating pattern. The resistance of the sensors has to be within a defined range: lower values cause loss of sensitivity, resistors higher than certain values are not able to be read by some control circuitry. Pits no larger than half the width of the heater line (~40 µm) should be present on the oxide surface. Since heaters carry high currents, pits in the metal will cause hot spots in the heater and will cause the heater to fail over repeated operation. As the surface of the heater is mechanically pressed against by for example, a plastic microfluidic cartridge repeatedly, pits cause the metal to wear out over time. The resistance of heater should be within a controlled range in order to carry desired current.

The foregoing description is intended to illustrate various aspects of the present technology. It is not intended that the examples presented herein limit the scope of the present technology. The technology now being fully described, it will be apparent to one of ordinary skill in the art that many changes and modifications can be made thereto without departing from the spirit or scope of the appended claims.

What is claimed:
1. A heater substrate, comprising:
   a plurality of groups of resistive heaters, and at least one temperature sensor per group of heaters, wherein a portion of the substrate is removed from around the resistive heaters to reduce the effective thermal mass adjacent to the heater group; and
   control circuitry for supplying electric current to the plurality of groups of resistive heaters at selected intervals, wherein the substrate has a surface configured to make thermal contact with a microfluidic cartridge having a plurality of PCR reaction chambers, and to deliver heat from the plurality of groups of resistive heaters to regions of the cartridge, such that each of the groups of resistive heaters delivers heat to a select PCR reaction chamber to perform a reaction, wherein the heat delivery from each group of resistive heaters is controlled by sensing temperature using the at least one temperature sensor of the group.

2. The heater substrate of claim 1, wherein a group of resistive heaters is shaped similar to a reaction chamber and the resistive heaters in the group are arranged to provide uniform heating in an area enclosed by the group.

3. The heater substrate of claim 2, wherein the area is between 1 mm$^2$ and 100 mm$^2$.

4. The heater substrate of claim 1, wherein at least one of the resistive heaters in a group of resistive heaters is also a temperature sensor.

5. The heater substrate of claim 1, wherein two adjacent heater groups are spaced apart by a distance to permit independent operation of their respective adjacent reaction chambers in the microfluidic cartridge.

6. The heater substrate of claim 1, wherein the reaction performed is thermocycling for PCR.

7. The heater substrate of claim 6, wherein one PCR heat cycle is performed in less than about 25 seconds.

8. The heater substrate of claim 1, further comprising heaters to actuate other microfluidic components in the microfluidic cartridge, including valves, pumps, or gates.

9. The heater substrate of claim 1, further comprising a processor, wherein the processor is programmable to operate the control circuitry.

10. The heater substrate of claim 1, further comprising a compliant layer at the surface, configured to thermally couple the heater groups with at least a portion of a microfluidic cartridge in contact with the surface.

11. A diagnostic apparatus configured to carry out PCR on a number of samples in parallel, wherein the apparatus utilizes a heater substrate of claim 1 to apply thermal cycling to each of the samples.

12. The heater substrate of claim 1, wherein the substrate comprises one or more materials selected from the group consisting of: glass, fused silica, and quartz.

13. The heater substrate of claim 1, wherein the plurality of groups of resistive heaters are arranged into lanes, such that each lane corresponds to a PCR reaction chamber in the microfluidic substrate.

14. The heater substrate of claim 13, wherein there are 12, 24, 48, or 96 lanes.

15. The heater substrate of claim 1, wherein a group consists of two long heaters and two short heaters.

16. The heater substrate of claim 1, wherein the PCR heat cycle time is further reduced by forced cooling during the cooling part of the PCR cycle.

17. The heater substrate of claim 1, wherein the substrate comprises a heater chip and a printed circuit board.

18. The heater substrate of claim 17, wherein the portion of the substrate removed from around the resistive heaters comprises at least a portion of the printed circuit board.

19. The heater substrate of claim 17, wherein the portion of the substrate removed from around the resistive heaters comprises at least a portion of the heater chip.

* * * * *

UNITED STATES PATENT AND TRADEMARK OFFICE
CERTIFICATE OF CORRECTION

PATENT NO. : 8,088,616 B2  
APPLICATION NO. : 11/940315  
DATED : January 3, 2012  
INVENTOR(S) : Handique Page 1 of 2

It is certified that error appears in the above-identified patent and that said Letters Patent is hereby corrected as shown below:

Title Page:

Page 1 (item 56, Other Publications) at column 2, line 13, change "Microfuidic" to --Microfluidic--.

Page 1 (item 57, Abstract) at column 2, line 34, change "of" to --or--.

Page 5 (item 56, Other Publications) at column 2, line 20, change ""Microflidic" to --"Microfluidic--.

Page 5 (item 56, Other Publications) at column 2, line 27, change "Micochannel"" to --MicroChannel"--.

Page 5 (item 56, Other Publications) at column 2, line 31, change "Microfludic" to --Microfluidic--.

Page 5 (item 56, Other Publications) at column 2, line 38, change "Concentraction" to --Concentration--.

Page 5 (item 56, Other Publications) at column 2, line 43, change "Microfludic" to --Microfluidic--.

Page 5 (item 56, Other Publications) at column 2, line 64, change "Fragnients" to --Fragments--.

Page 6 (item 56, Other Publications) at column 2, line 4, change "fro" to --from--.

Page 6 (item 56, Other Publications) at column 2, line 5, change "Polyamidomine" to --Polyamidoamine--.

In the Drawings:

Sheet 27 of 43 (FIG. 18) at line 13 (approx.), change " 12l " to --1200--.

In the Specification:

In column 4 at lines 41-42, change "micro fluidic" to --microfluidic--.  
In column 5 at line 34, change "micro fluidic" to --microfluidic--.  
In column 5 at line 37, change "micro fluidic" to --microfluidic--.

Signed and Sealed this  
Third Day of December, 2013

Margaret A. Focarino  
*Commissioner for Patents of the United States Patent and Trademark Office*

CERTIFICATE OF CORRECTION (continued)
U.S. Pat. No. 8,088,616 B2

In column 8 at line 67, change "g/m" to --µm--.

In column 12 at line 28, change "228,230" to --228, 230--.

In column 12 at line 32 (approx.), change "FIG. 29A," to --FIG. 9A,--.

In column 12 at line 63, change "gate" to --gates--.

In column 16 at line 61, change "Serial-Deserializer" to --Serializer-Deserializer--.

In column 23 at line 47, change "3.5×4.25" to --~3.5×4.25--.